(12) United States Patent
Taylor et al.

(10) Patent No.: US 7,960,152 B2
(45) Date of Patent: Jun. 14, 2011

(54) METHODS FOR PRODUCTION OF XYLITOL IN MICROORGANISMS

(75) Inventors: Paul Taylor, Arlington Heights, IL (US); Ian Fotheringham, Schaumburg, IL (US); Nathan Wymer, Peoria, IL (US); Badal Saha, Peoria, IL (US); David Demirjian, Hinsdale, IL (US); Yoshikiyo Sakaibara, Peoria, IL (US); Francis Michael Racine, Peoria, IL (US)

(73) Assignee: Biotechnology Research Development Corporation, Peoria, IL (US)

( * ) Notice: Subject to any disclaimer, the term of this patent is extended or adjusted under 35 U.S.C. 154(b) by 0 days.

(21) Appl. No.: 11/133,045

(22) Filed: May 19, 2005

(65) Prior Publication Data

US 2006/0110809 A1    May 25, 2006

Related U.S. Application Data

(60) Provisional application No. 60/572,588, filed on May 19, 2004, provisional application No. 60/620,173, filed on Oct. 18, 2004, provisional application No. 60/572,438, filed on May 19, 2004.

(51) Int. Cl.
    *C12P 7/60*          (2006.01)
    *C12N 1/21*         (2006.01)

(52) U.S. Cl. .................. 435/138; 435/252.33; 435/252.3

(58) Field of Classification Search .......................... None
See application file for complete search history.

(56) References Cited

U.S. PATENT DOCUMENTS

| | | |
|---|---|---|
| 3,586,537 A | 6/1971 | Steiner et al. |
| 3,784,408 A | 1/1974 | Jaffe et al. |
| 4,008,285 A | 2/1977 | Melaja et al. |
| 4,066,711 A | 1/1978 | Melaja et al. |
| 4,075,406 A | 2/1978 | Melaja et al. |
| 5,081,026 A | 1/1992 | Heikkila et al. |
| 5,631,150 A | 5/1997 | Harkki et al. |
| 5,686,277 A | 11/1997 | Kim et al. |
| 5,789,210 A | 8/1998 | Ho et al. |
| 5,866,382 A | 2/1999 | Halibom et al. |
| 5,998,181 A | 12/1999 | Kim et al. |
| 5,998,607 A | 12/1999 | Heikkila et al. |
| 6,221,634 B1 | 4/2001 | Takeuchi et al. |
| 6,242,228 B1 | 6/2001 | Sugiyama et al. |
| 6,271,007 B1 | 8/2001 | Apajalahti et al. |
| 6,303,353 B1 | 10/2001 | Sugiyama et al. |
| 6,335,177 B1 | 1/2002 | Mihara et al. |
| 6,340,582 B1 | 1/2002 | Suzuki et al. |
| 6,458,570 B1 | 10/2002 | Elseviers et al. |
| 6,723,540 B1 | 4/2004 | Harkki et al. |
| 2001/0034049 A1 | 10/2001 | Sugiyama et al. |
| 2002/0061561 A1 | 5/2002 | Mihara et al. |
| 2002/0076772 A1 | 6/2002 | Elseviers |
| 2003/0041352 A1* | 2/2003 | Parrott et al. .................. 800/288 |
| 2003/0068791 A1 | 4/2003 | Miasnikov et al. |
| 2003/0097029 A1 | 5/2003 | Heikkila et al. |
| 2003/0125588 A1 | 7/2003 | Heikkila et al. |
| 2003/0148482 A1 | 8/2003 | Takenaka et al. |
| 2003/0186402 A1 | 10/2003 | Londesborough et al. |
| 2003/0235881 A1 | 12/2003 | Heikkila et al. |
| 2004/0014185 A1* | 1/2004 | Ojamo et al. .................. 435/158 |
| 2005/0158836 A1* | 7/2005 | Ingram et al. .................. 435/161 |

FOREIGN PATENT DOCUMENTS

| | | | |
|---|---|---|---|
| EP | 1022341 A1 | | 7/2000 |
| WO | 9533063 | | 5/1995 |
| WO | WO02/066616 | * | 8/2002 |
| WO | 02066616 | | 12/2002 |
| WO | 03097848 | | 11/2003 |
| WO | 2005026339 | | 3/2005 |

OTHER PUBLICATIONS

Heuel et al. Journal of Bacteriology. 1997;179 (19): 6014-6019.*
Han et al. Sheng Wu Gong Cheng Xue Bao (Chinese Journal of Biotechnology). Jan. 2004;20(1):16-20 (abstract only—in English).*
Verduyn et al. (Biochem. J. (1985) 226, 669-677).*
Saha (J Ind Microbiol Biotechnol. 2003; 30: 279-291).*
Invitation to Pay Additional Fee for corresponding PCT case PCT/US2005/017550 dated Feb. 17, 2006.
Feldman, et al., "Pentose metabolism in *Zymomonas mobilis* wild-type and recombinant strains", Appl. Microb8iol. Biotechnol. (1992) 38, 354-361.
Toivari, et al., "Conversion of Xyloose to Ethanol by Recombinant *Saccharomyces cerevisiae*: Importance of Xylulokinase (XKS1) and Oxygen Availablility", Metabolic Engineering 3, 236-249 (2001).
Ibañez, et al., "Role of the yiaR and yiaS Genes of *Escherichia coli* in Metabolism of Endogenously Formed L-Xylulose", *Journal of Bacteriology*, p. 4625-4627, vol. 182, No. 16, 2000.
Reiner "Genes for Ribitol and D-Arabitol Catabolism in *Escherichia coli*: Their Loci in C Strains and Absence in K-12 and B Strains", *Journal of Bacteriology*, vol. 123, No. 2, p. 530-536, 1975.
Richard, et al., "Cloning and Expression of a Fungal L-Arabinitol 4-Dehydrogenase Gene", *The Journal of Biological Chemistry*, vol. 276, No. 44, p. 40631-40637, 2001.
Scangos, et al., "Acquisition of Ability to Utilize Xylitol: Disadvantages of a Constitutive Catabolic Pathway in *Escherichia coli*", *Journal of Bacteriology*, vol. 134, No. 2, p. 501-505, 1978.
Yew, et al., "Utilization of L-Ascorbate by *Escherichia coli* K-122: Assignments of Functions to Products in the yif-sga and yia-sgb Operons", *Journal of Bacteriology*, vol. 184, No. 1, p. 302-306, 2002.
Badia, et al., "L-Lyxose Metabolism Employs the L-Rhamnose Pathway in Mutant Cells of *Escherichia coli* Adapted to Grow on L-Lyxose", *Journal of Bacteriology*, vol. 173, No. 16, p. 5144-5150, 1991.
Doten, et al., "Inducible Xylitol Dehydrogenases in Enteric Bacteria", *Journal of Bacteriology*, vol. 162, No. 2, p. 845-848, 1985.
Doten, et al., "Directed Evolution of a Second Xylitol Catabolic Pathway in *Klebsiella pneumoniae*", *Journal of Bacteriology*, vol. 159, No. 2, p. 730-735, 1984.

(Continued)

*Primary Examiner* — Scott Long
(74) *Attorney, Agent, or Firm* — McDonnell Boehnen Hulbert & Berghoff LLP

(57) ABSTRACT

The invention provides biosynthetic routes to xylitol production that do not require pure D-xylose for synthesis and that can utilize inexpensive substrates such as hemicellulose hydrolysates.

35 Claims, 28 Drawing Sheets

OTHER PUBLICATIONS

Doten, et al., "Characterization of Xylitol-Utilizing Mutants of *Erwinia uredovora*", *Journal of Bacteriology*, vol. 161, No. 2, p. 529-533, 1985.

Richard, et al., "Production of ethanol from L-arabinose by *Saccharomyces cerevisiae* containing a fungal L-arabinose pathway", *FEMS Yeast Research*, 3 (2003) 185-189.

Saha, et al., "Production of Xylitol by *Candida peltata*", *Journal of Industrial Microbiology & Biotechnology*, (1999) 22, 633-636.

Saha, et al., "Microbial Production of Xylitol", *Fuels and Chemicals from Biomass*, p. 307-319, 1997.

Jeffries, et al., "Strain selection, taxonomy, and genetics of xylose-fermenting yeasts", *Enzyme Microb. Technol.*, vol. 16, p. 922-932, 1994.

Hahn-Hägerdal, et al., "Biochemistry and physiology of xylose fermentation by yeasts", *Enzyme Microb. Technol.*, vol. 16, p. 933-943, 1994.

Neuhauser, et al., "A pH-Controlled Fed-Batch Process Can Overcome Inhibition by Formate in NADH-Dependent Enzymatic Reductions Using Formate Dehydrogenase-Catalyzed Coenzyme Regeneration", *Biotechnology and Bioengineering*, vol. 60, No. 3, p. 277-282, 1998.

Kern, et al., "Induction of aldose reductase and xylitol dehydrogenase activities in *Candida tenuis* CBS 4435", *FEMS Microbiology Letters*, 149 (1997) 31-37.

Kim, et al., "Optimization of fed-batch fermentation for xylitol production by *Candida tropicalis*", *Journal of Industrial Microbiology & Biotechnology*, (2002) 29, 16-19.

Lee, et al., "Substrate Specificity and Kinetic Mechanism of *Escherichia coli* Ribulokinase", *Archives of Biochemistry and Biophysics*, vol. 396, No. 2, p. 219-224, 2001.

Richard, et al., "The Missing Link in the fungal L-Arabinose Catabolic Pathway, Identification of the L-Xylulose Reductase Gene", *Biochemistry*, vol. 41, No. 20, p. 6432-6437, 2002.

Genbank Accession No. AF045244, Jul. 16, 1998.
Genbank Accession No. M25606, Apr. 26, 1993.
Genbank Accession No. AJ583159, Apr. 15, 2005.
Genbank Accession No. AF428150, Oct. 15, 2003.
Genbank Accession No. AF375616, Jul. 23, 2002.
Genbank Accession No. AF355628, Oct. 30, 2001.
Genbank Accession No. AF074484, Mar. 15, 2002.
Genbank Accession No. AE00129, Dec. 1, 2000.
Genbank Accession No. X59465, Apr. 18, 2005.
Genbank Accession No. X04691, Apr. 18, 2005.
Genbank Accession No. K01996, Apr. 26, 1993.
Genbank Accession No. X68025, Feb. 17, 1997.

Datsenko, et al., "One-step inactivation of chromosomal genes in *Escherichia coli* K-12 using PCR products", *PNAS*, vol. 97, No. 12, p. 6640-6645, 2000.

Kimata, et al., "cAMP receptor protein-cAMP plays a crucial role in glucose-lactose diauxie by activating the major glucose transporter gene in *Escherichia coli*", *Proc. Natl. Acad. Sci. USA*, vol. 94, p. 12914-12919, 1997.

Keiler, et al., "Sequence Determinants of C-terminal Substrate Recognition by the Tsp Protease", *The Journal of Biological Chemistry*, vol. 271, No. 5, p. 2589-2593, 1996.

Andersen, et al., "New Unstable Variants of Green Fluorescent Protein for Studies of Transient Gene Expression in Bacteria", *Applied and Environmental Microbiology*, vol. 64, No. 6, p. 2240-2246, 1998.

Scangos, et al., "A Unique Pattern of Toxic Synthesis in Pentitol Catabolism: Implications for Evolution", *Journal of Molecular Evolution*, 12, 189-195, 1979.

Izumori, et al., "Production of Xylitol from D-Xylulose by *Mycobacterium smegmatis*", *J. Ferment. Technol.*, vol. 66, No. 1, 33-36, 1988.

Walthers, et al., "Model of Compound Studies", *Applied Biochemistry and Biotechnology*, vol. 91-93, p. 423-435, 2001.

Calos, "DNA sequence for a low-level promoter of the lac repressor gene and an "up" promoter mutation", *Nature*, vol. 274, 24, 762-765, 1978.

Stark, "Multicopy expression vectors carrying the lac repressor for regulated high-level expression of genes in *Escherichia coli*", *Gene*, 51 (1987) 255-267.

Keiler, et al., "Role of Peptide Tagging System in Degradation of Proteins Synthesized from Damaged Messenger RNA", *Science*, vol. 271, p. 990-993, 1996.

Nichols, et al., "use of catabolite repression mutants for fermentation of sugar mixtures to ethanol", *Appl. Microbiol. Biotechnol.*, (2001) 56:120-125.

Verho, et al., "A Novel NADH-linked L-Xylulose Reductase in the L-Arabinose Catabolic Pathway of Yeast", *The Journal of Biological Chemistry*, vol. 279, No. 15, p. 14746-14751, 2004.

Winelhausen, et al., "Microbial Conversion of D-Xylose to Xylitol", *Journal of Fermentation and Bioengineering*, vol. 86, No. 1, 1-14, 1998.

Nidetzky, et al., "Continuous Enzymatic Production of Xylitol with Simultaneous Coenzyme Regeneration in a Charged Membrane Reactor", *Biotechnology and Bioengineering*, vol. 52, p. 387-396, 1996.

Häcker, et al., "Xylose Utilisation: Cloning and Characterisation of the Xylose Reductase from *Candida tenuis*", *Biol. Chem.*, vol. 380, p. 1395-1403. 1999.

Richard, et al., "Cloning and Expression of a Fungal L-Arabinitol 4-Dehydrogenase Gene", *The Journal of Biological Chemistry*, vol. 276, No. 41, p. 40631-40637, 2001.

Klimacek, et al., "Altering dimmer contacts in xylose reductase from *Candida tenuis* by site-directed mutagenesis: structural and functional properties of R180A mutant", *Chemico-Biological Interactions*, 143-144 (2003) 523-532.

* cited by examiner

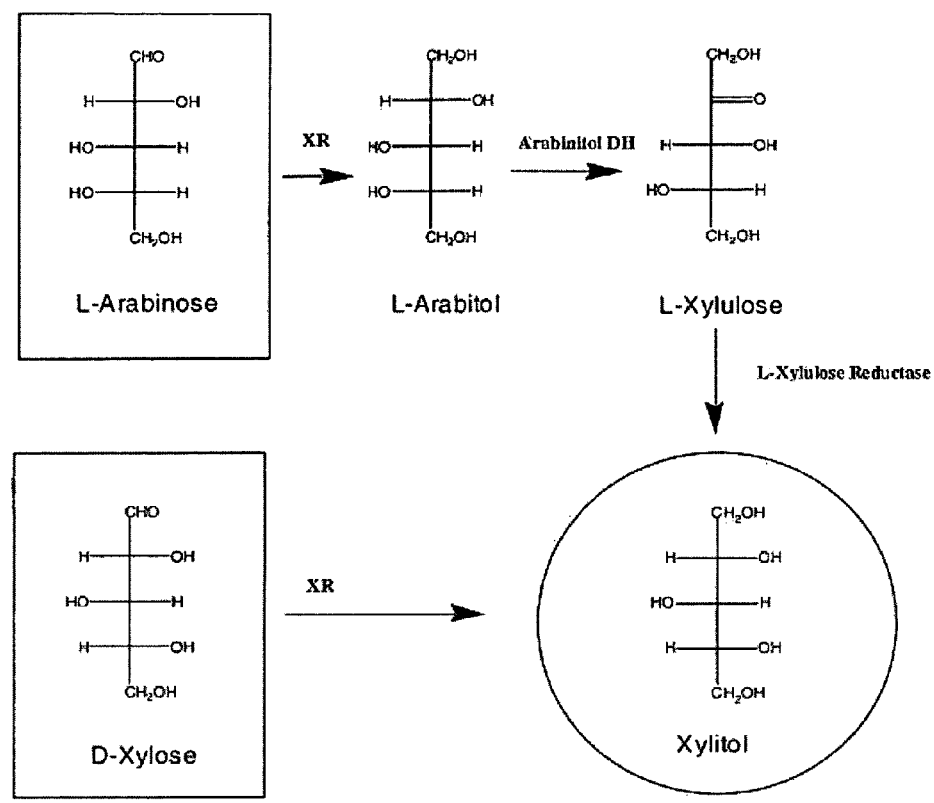
Figure 1. Xylitol synthesis from hemicellulose.

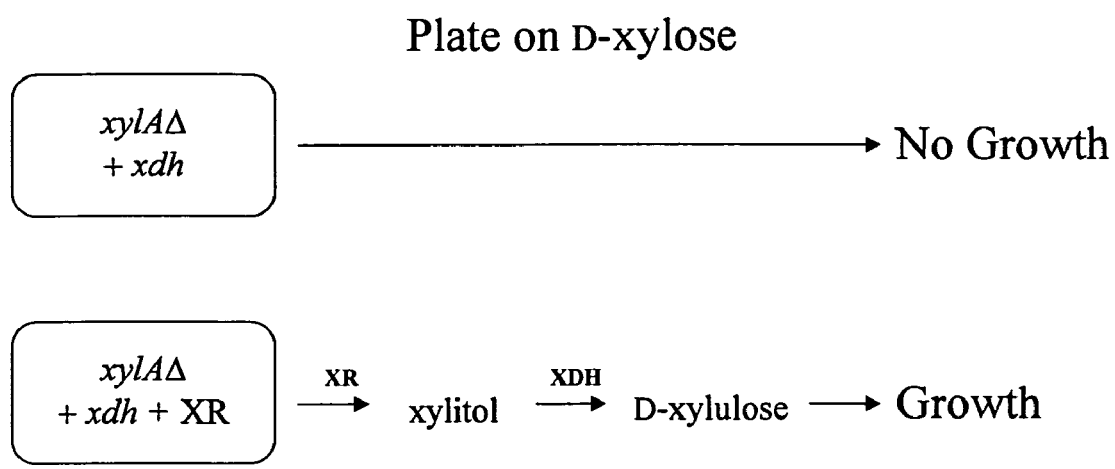
Figure 2. Xylose reductase screening strain

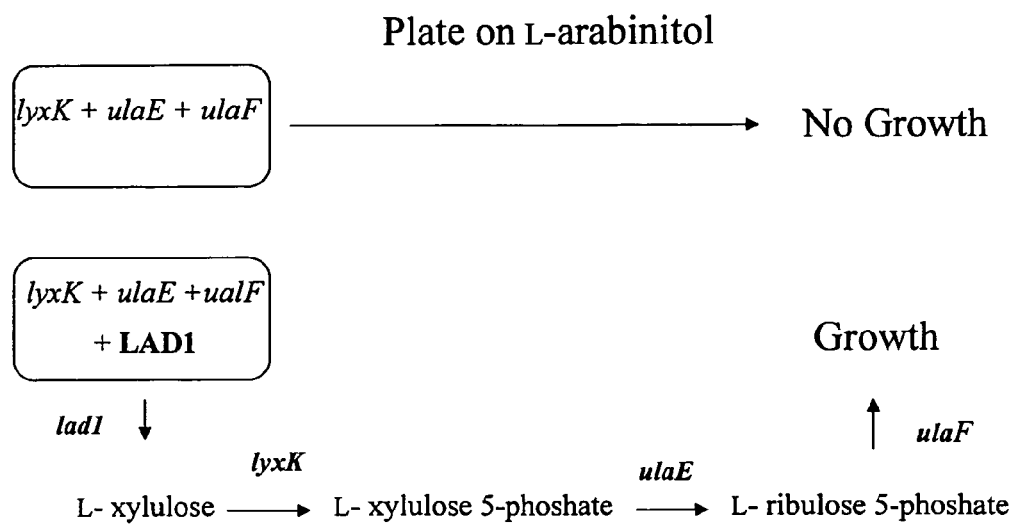
Figure 3. L-Arabitol 4-dehydrogenase screening strain.

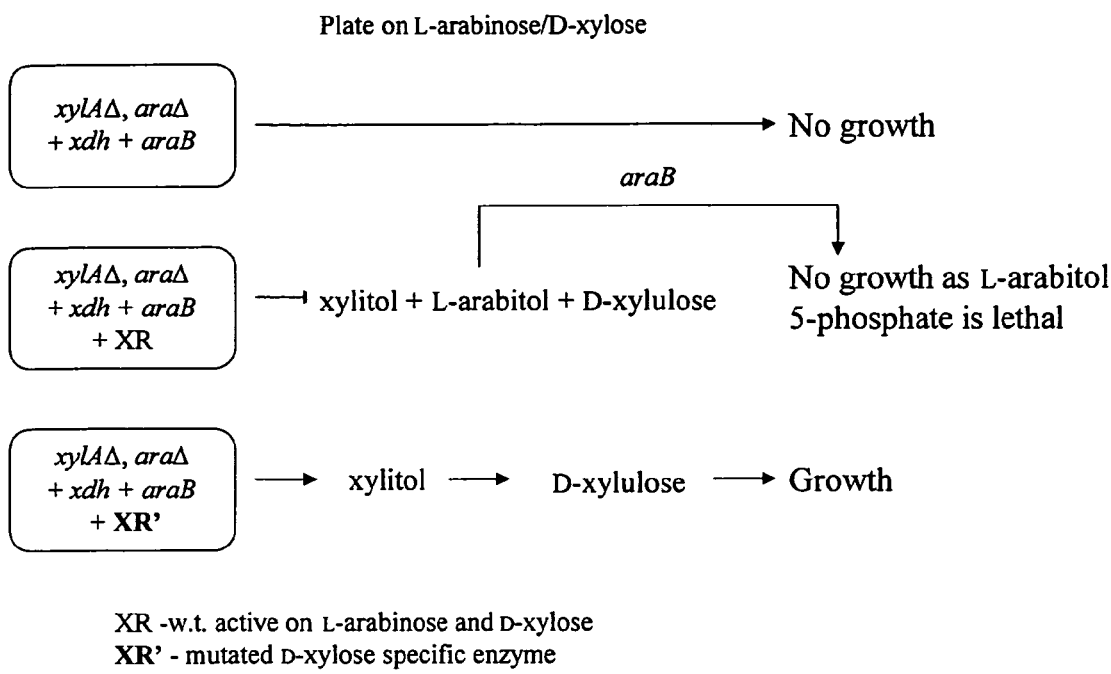
Figure 4. D-xylose specific screening strain.

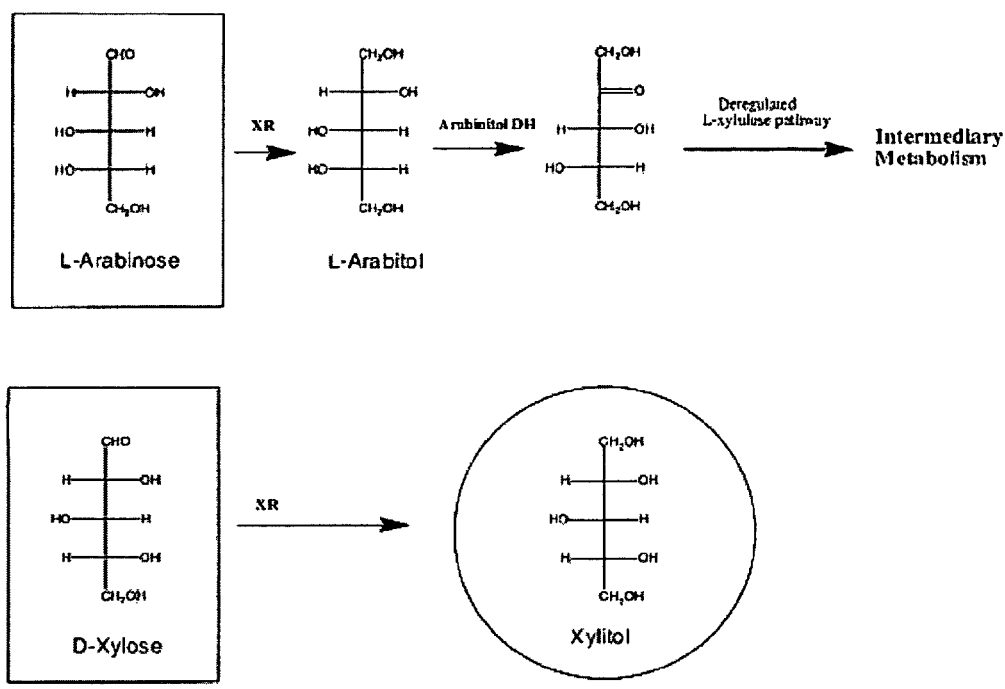
Figure 5. Route to pure xylitol using hemicellulose substrate.

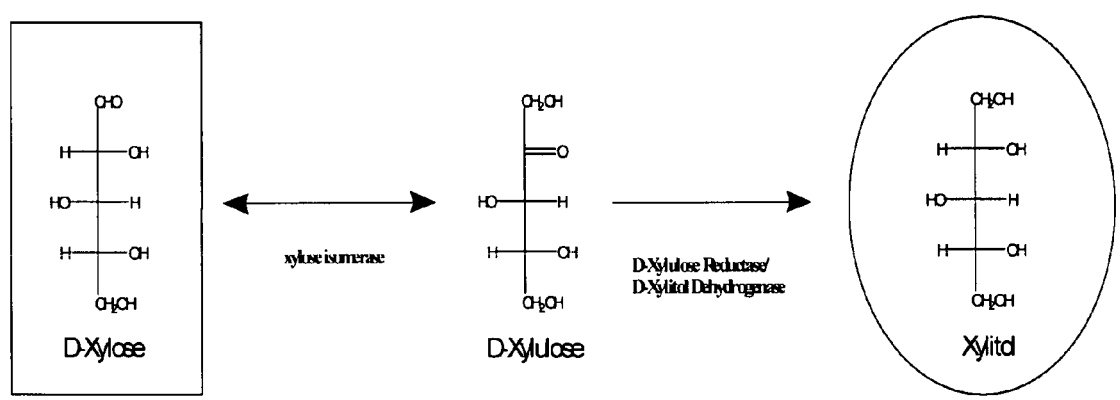
Figure 6. Alternative route to xylitol from D-xylose.

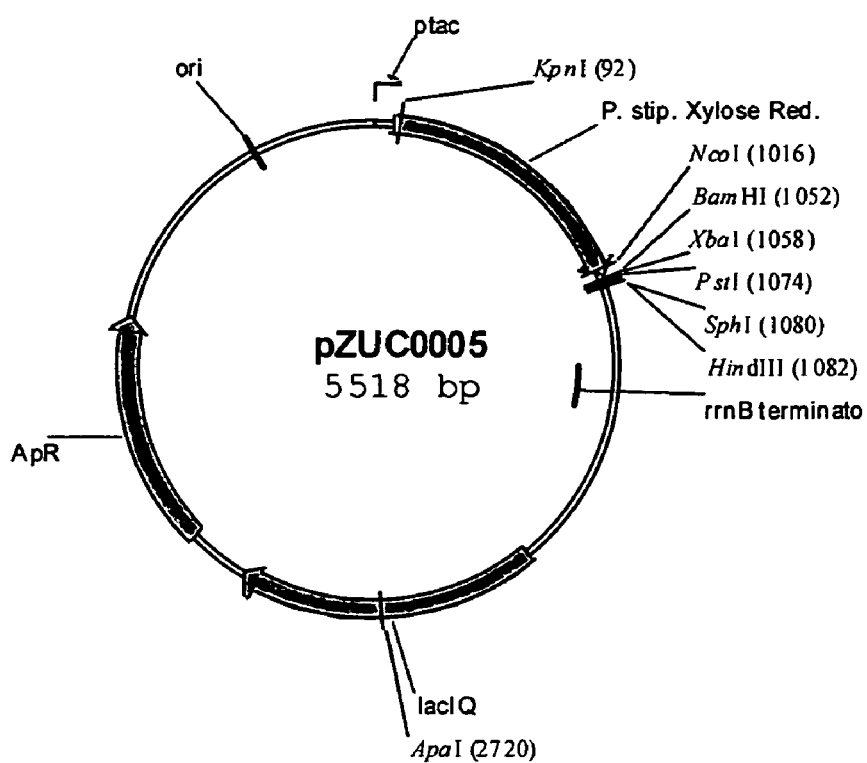
Figure 7. *P. stipitis* xylose reductase cloned into vector pTTQ18.

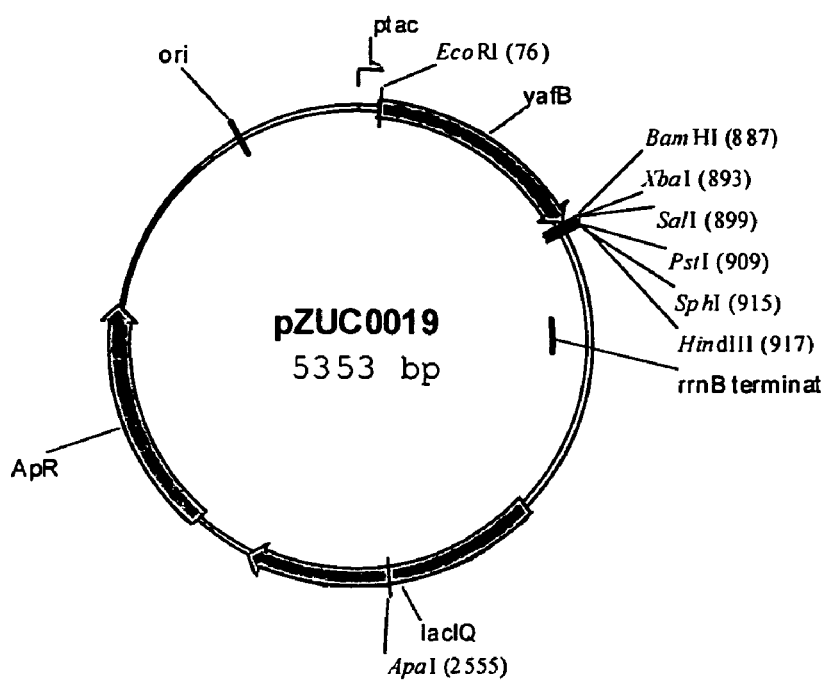
Figure 8. *E. coli yafB* (xylose reductase) cloned into vector pTTQ18.

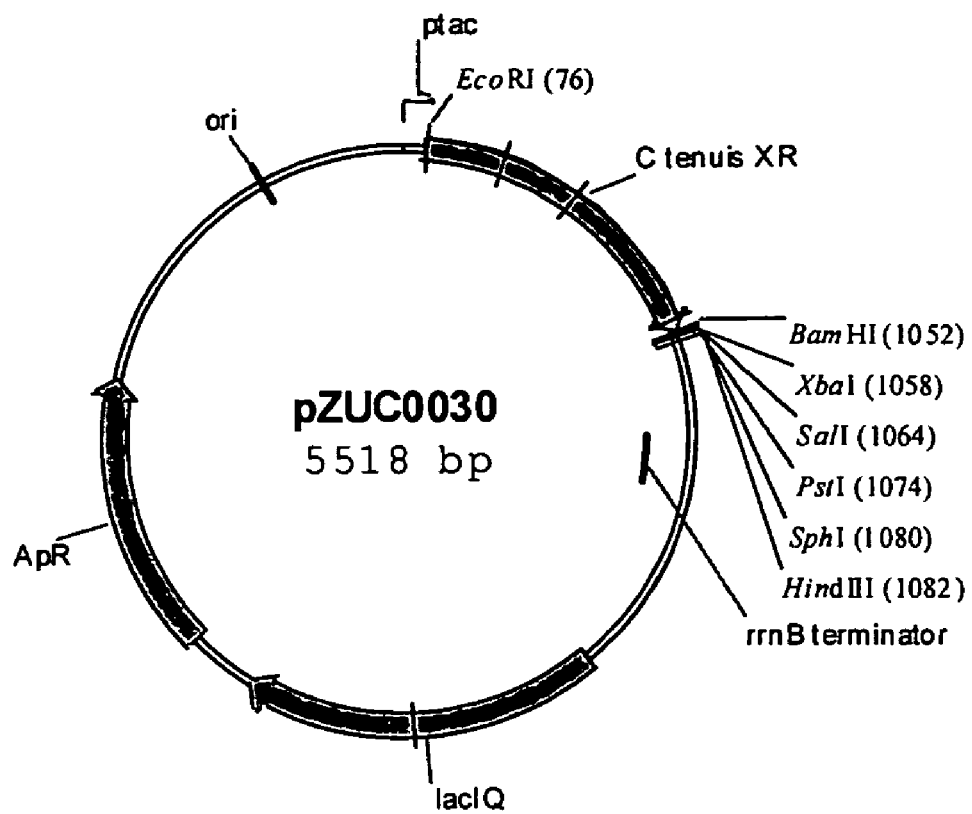
Figure 9. *Candida tenuis XR* gene cloned into pTTQ18.

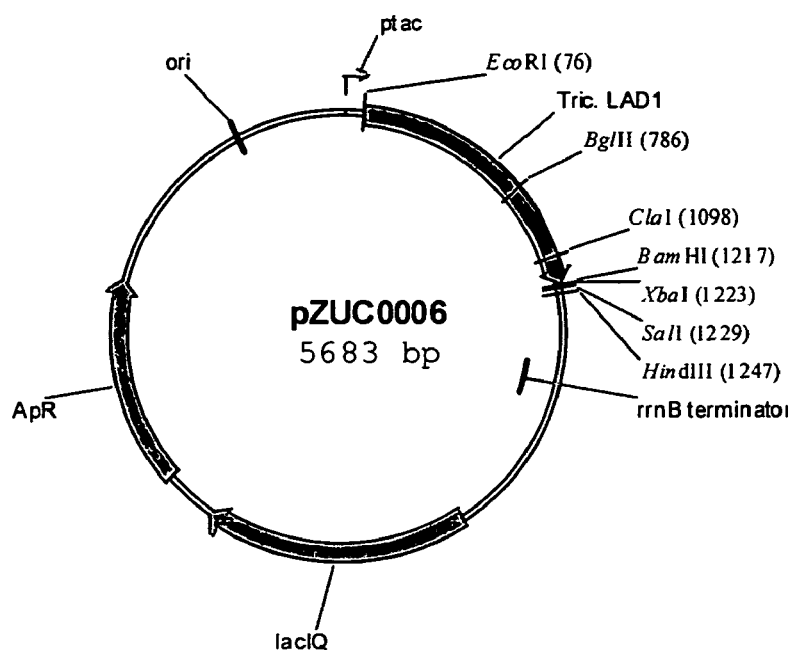
Figure 10. *Trichoderma reesei* L-arabitol 4-dehydrogenase gene cloned into pTTQ18.

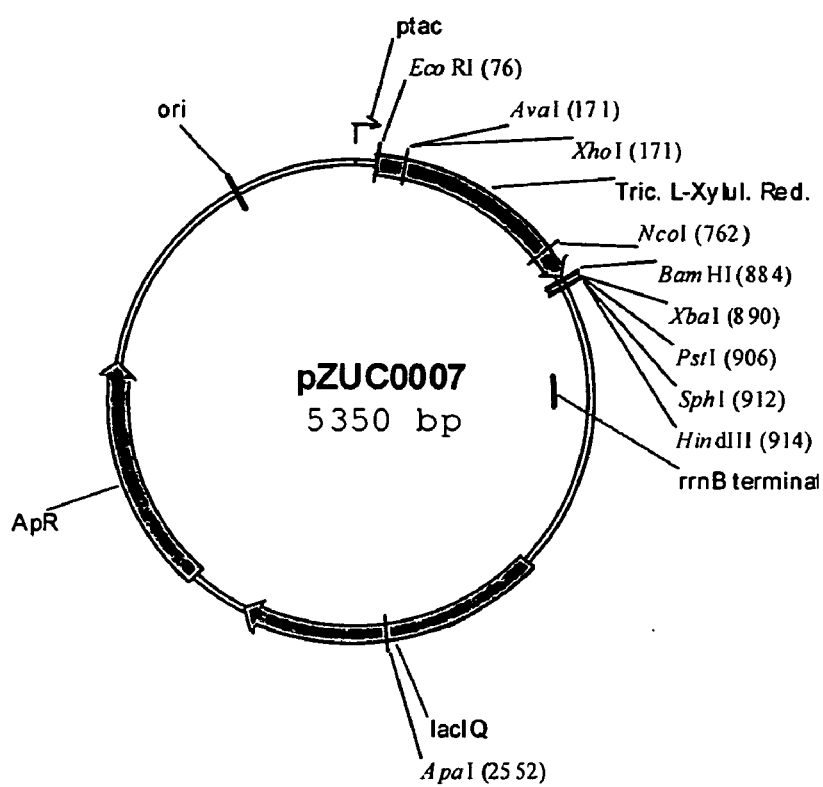
Figure 11. *Trichoderma reesei* L-xylulose reductase gene cloned into pTTQ18

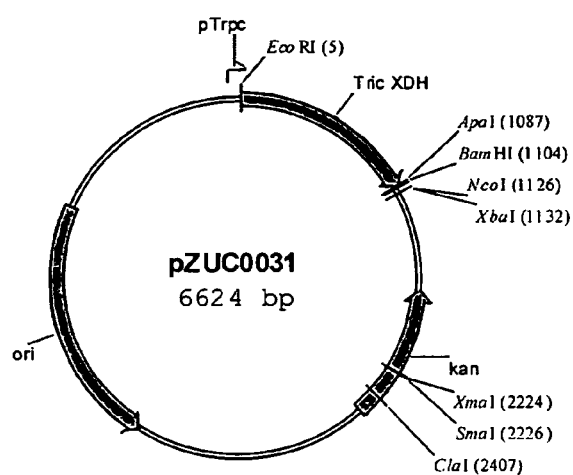
Figure 12. *Trichoderma reesei* xylitol dehydrogenase gene cloned into pTTQ18.

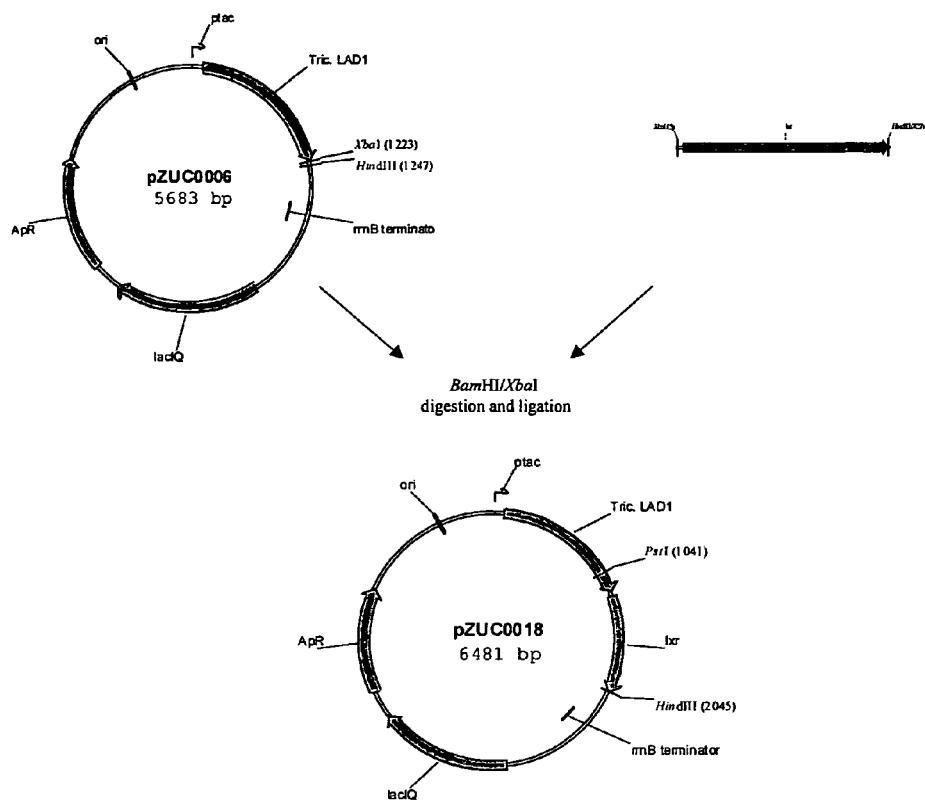
Figure 13. Construction of the L-arabitol 4-dehydrogenase/L-xylulose reductase operon.

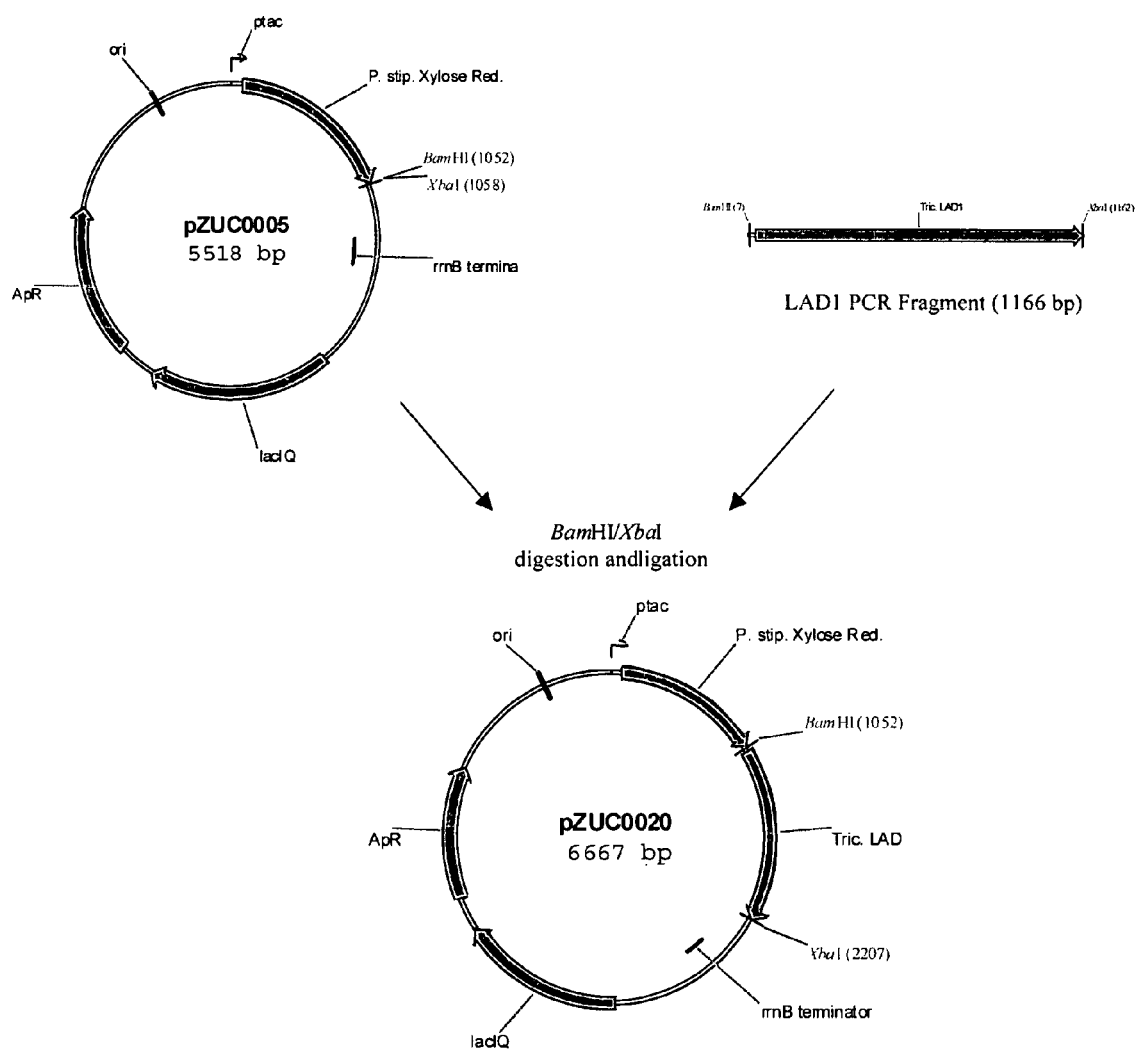
Figure 14. Construction of the XR/LAD1 operon.

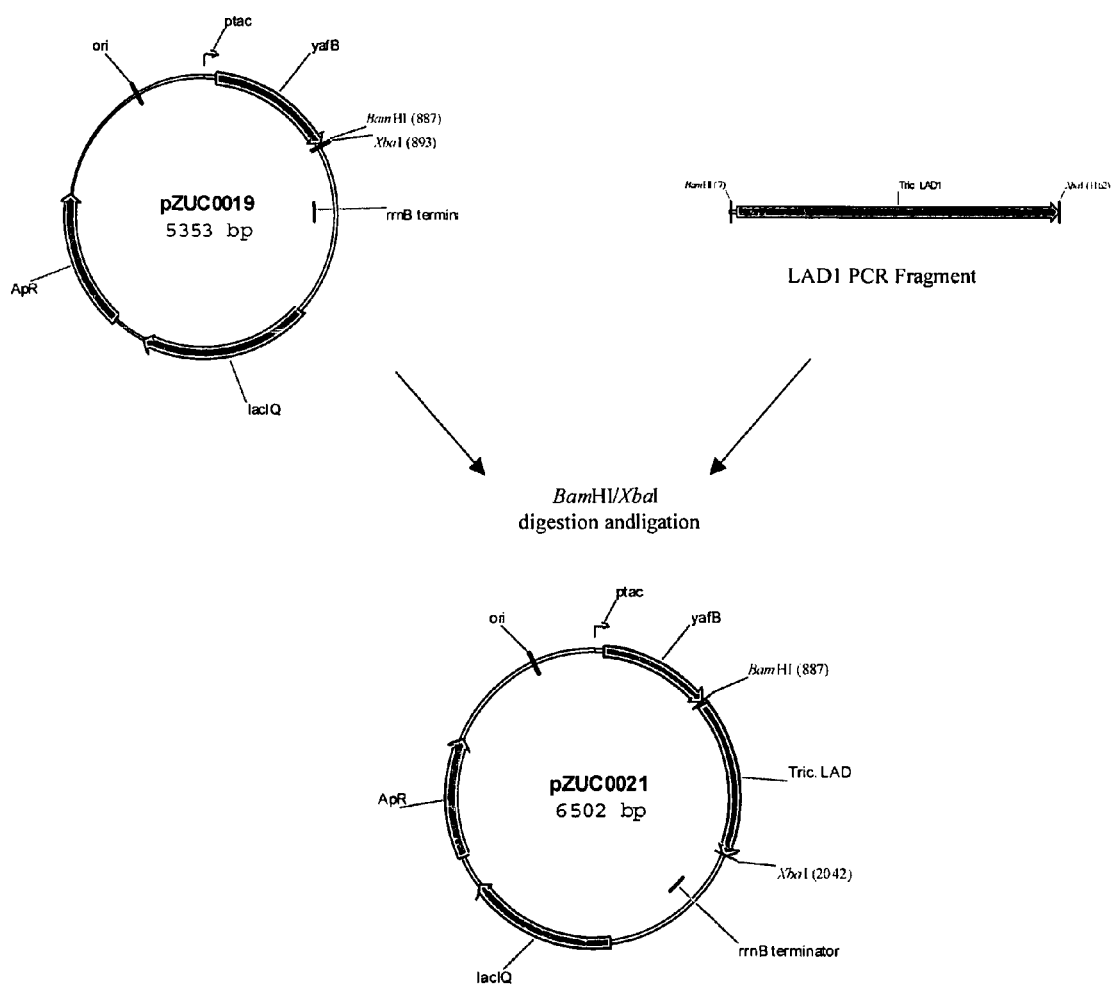
Figure 15. Construction of the yafB/LAD1 operon.

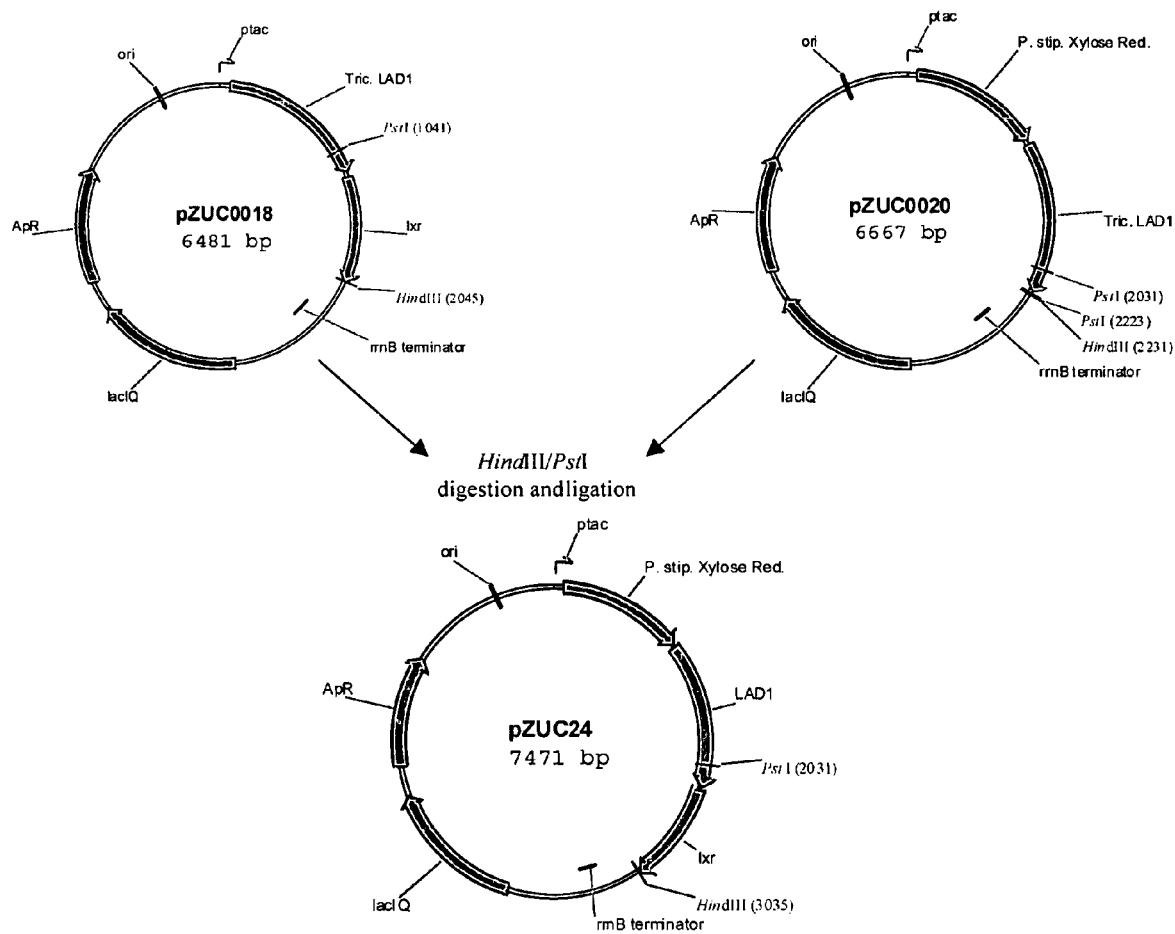
Figure 16. Construction of an XR/LAD1/LXR operon.

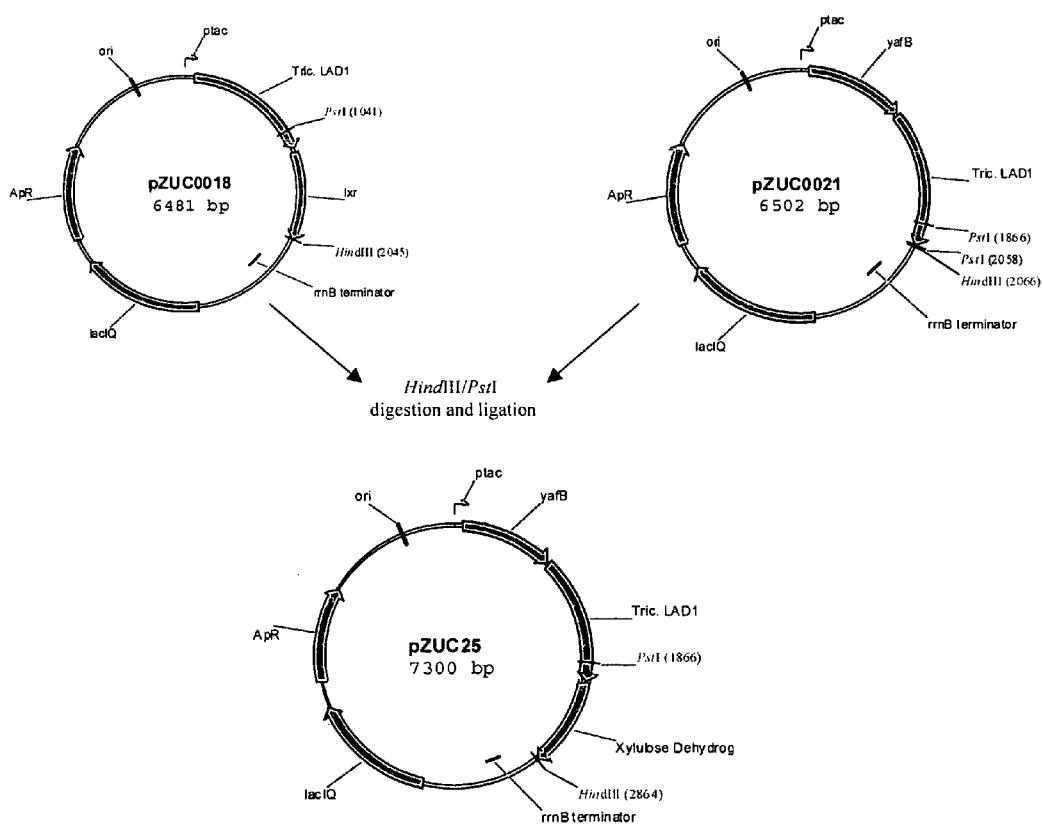
Figure 17. Construction of the yafB/LAD1/LXR operon.

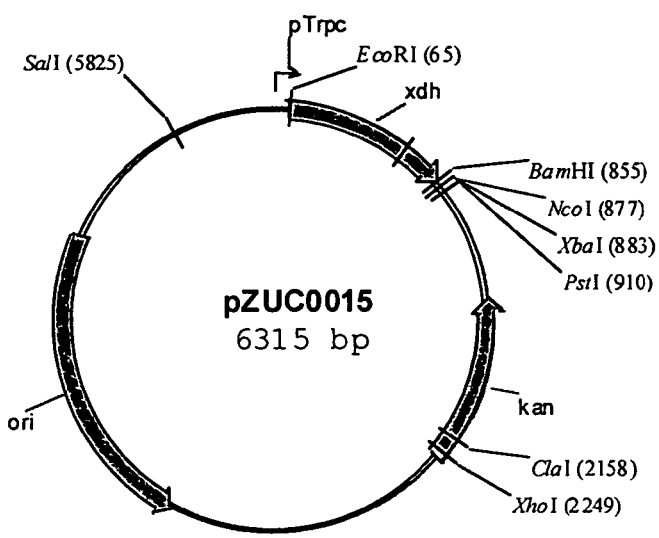
Figure 18. *Gluconobacter oxydans* xylitol dehydrogenase (*xdh*) gene cloned into pTTQ18.

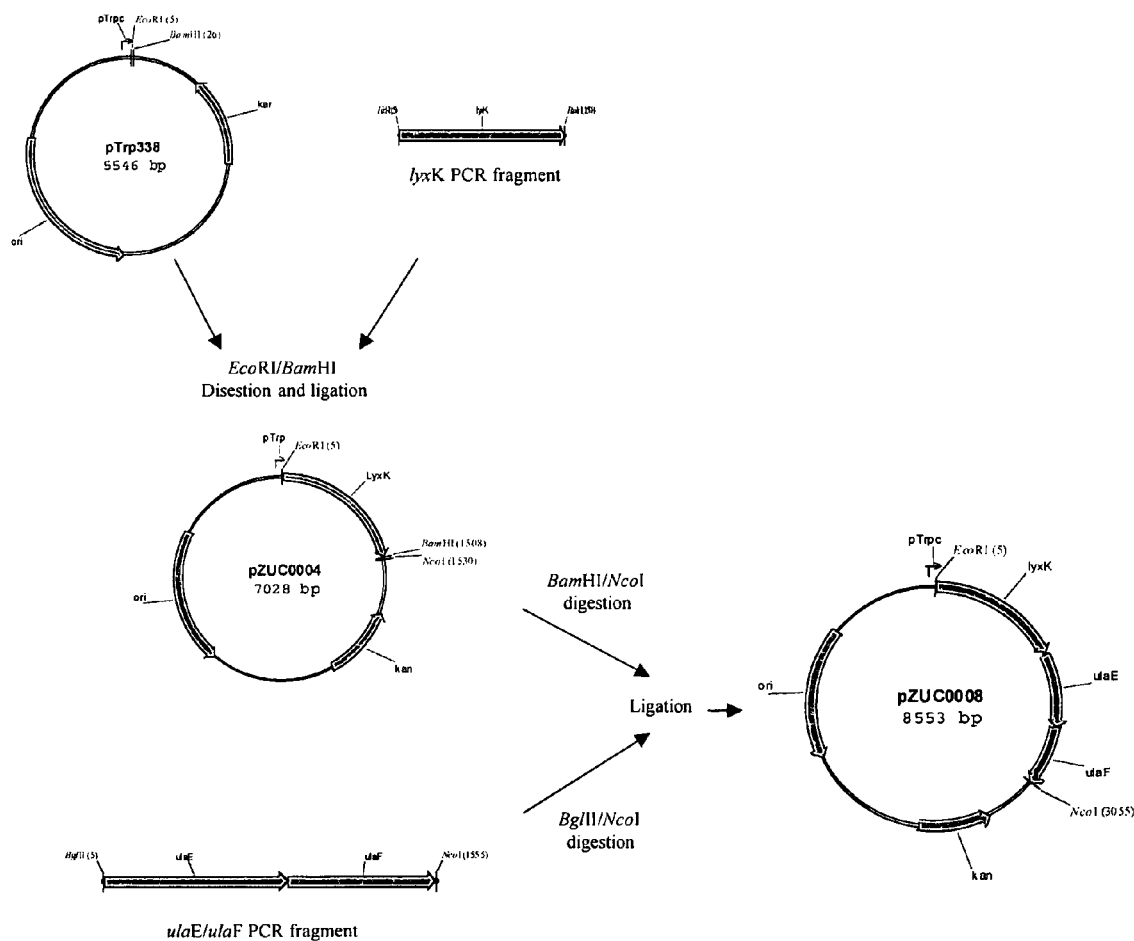
Figure 19. Construction of a constitutive L-xylulose degradation pathway in expression vector pTrp338.

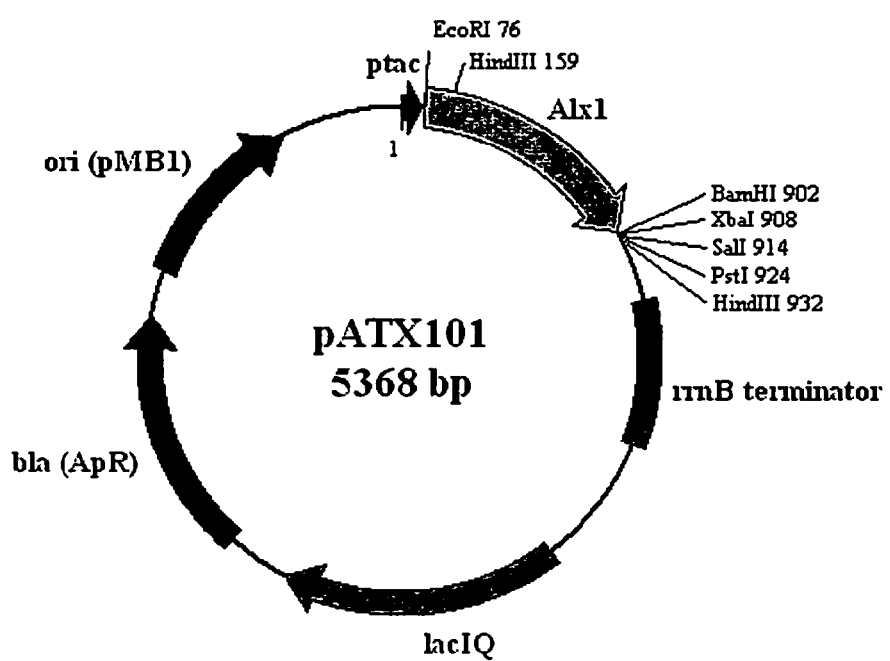
Figure 20. *A. monospora* L-xylulose reductase cloned into vector pTTQ18.

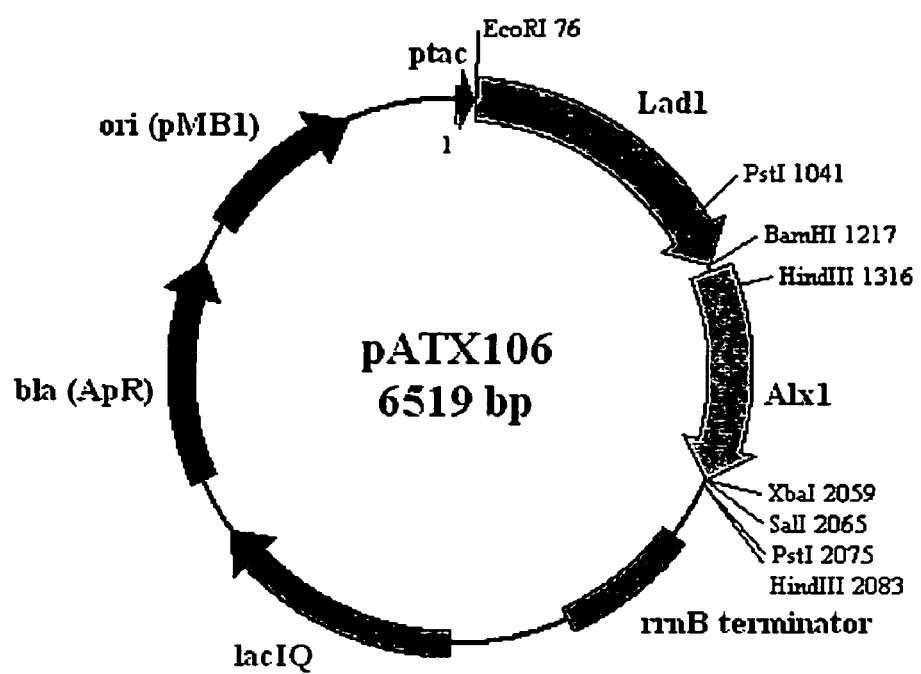
Figure 21. Lad1/Alx1 operon cloned into vector pTTQ18.

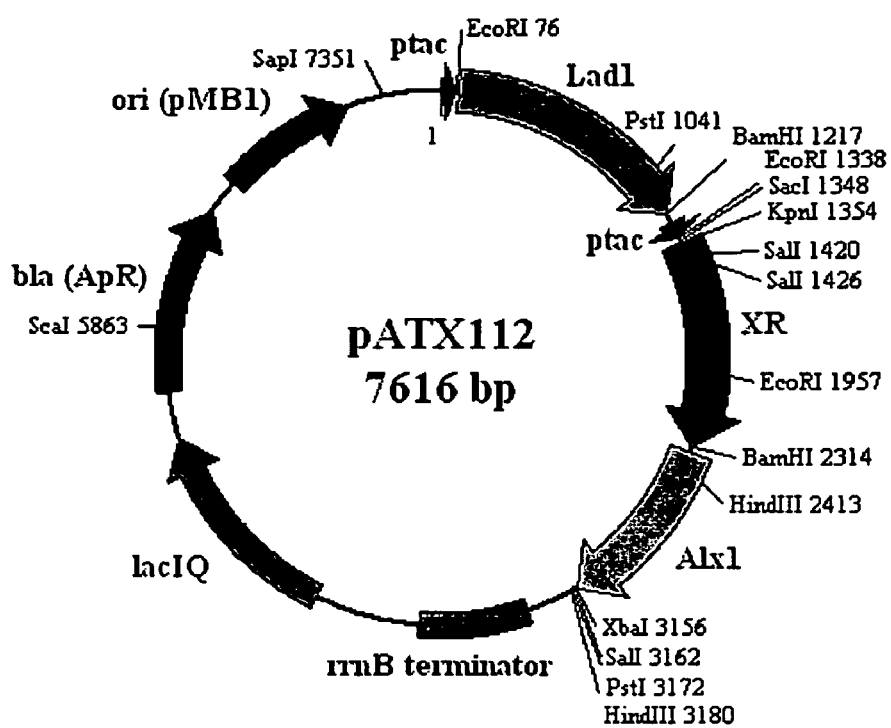
Figure 22. XR/Lad1/Alx1 operon cloned into vector pTTQ18.

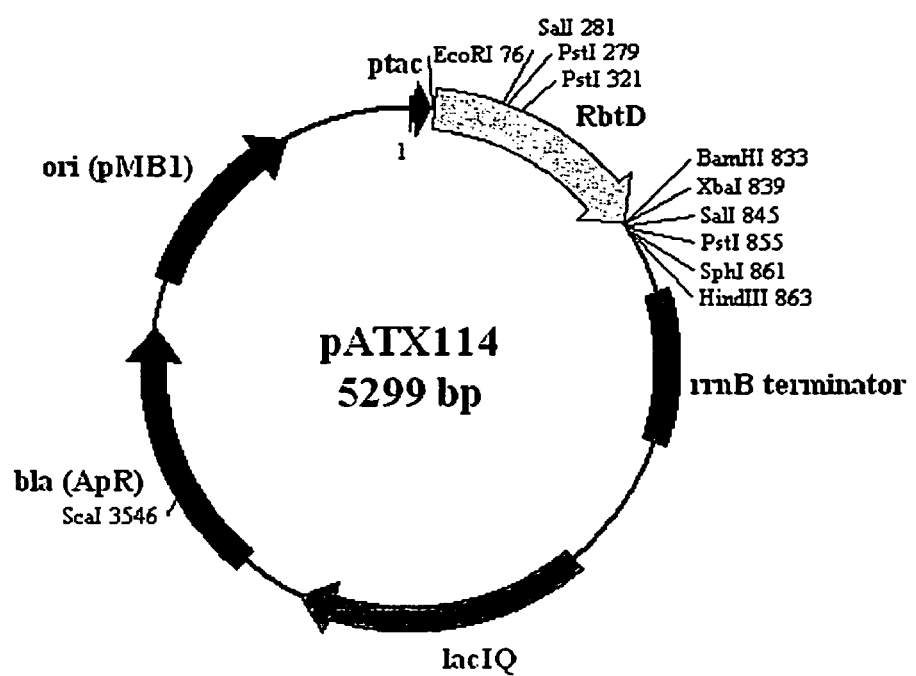
Figure 23. *K. pneumoniae* ribitol dehydrogenase cloned into vector pTTQ18.

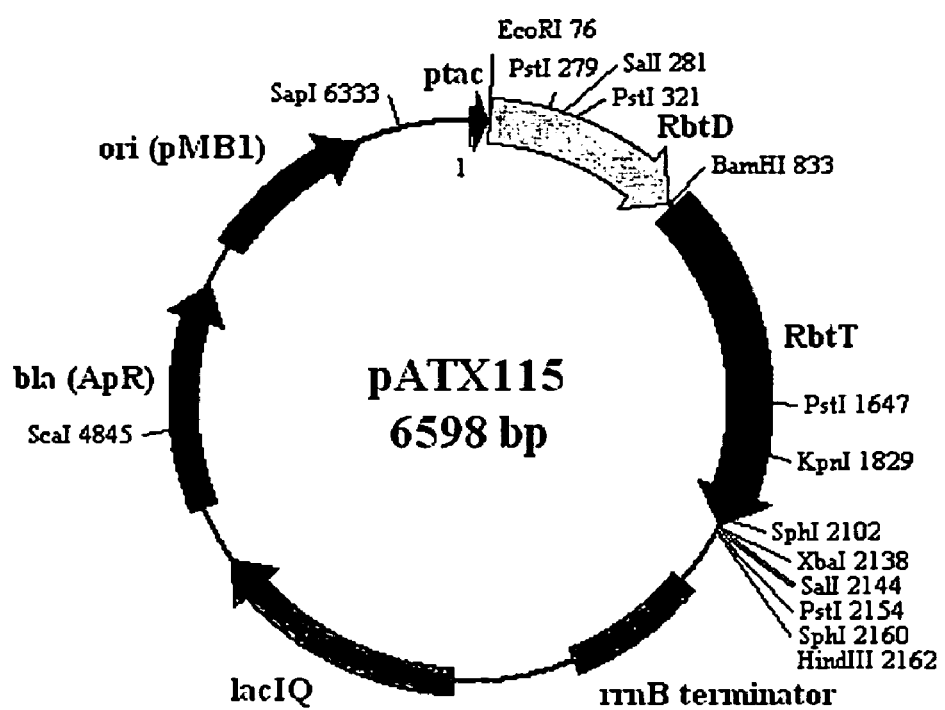
Figure 24. RbtD/RbtT operon cloned into vector pTTQ18.

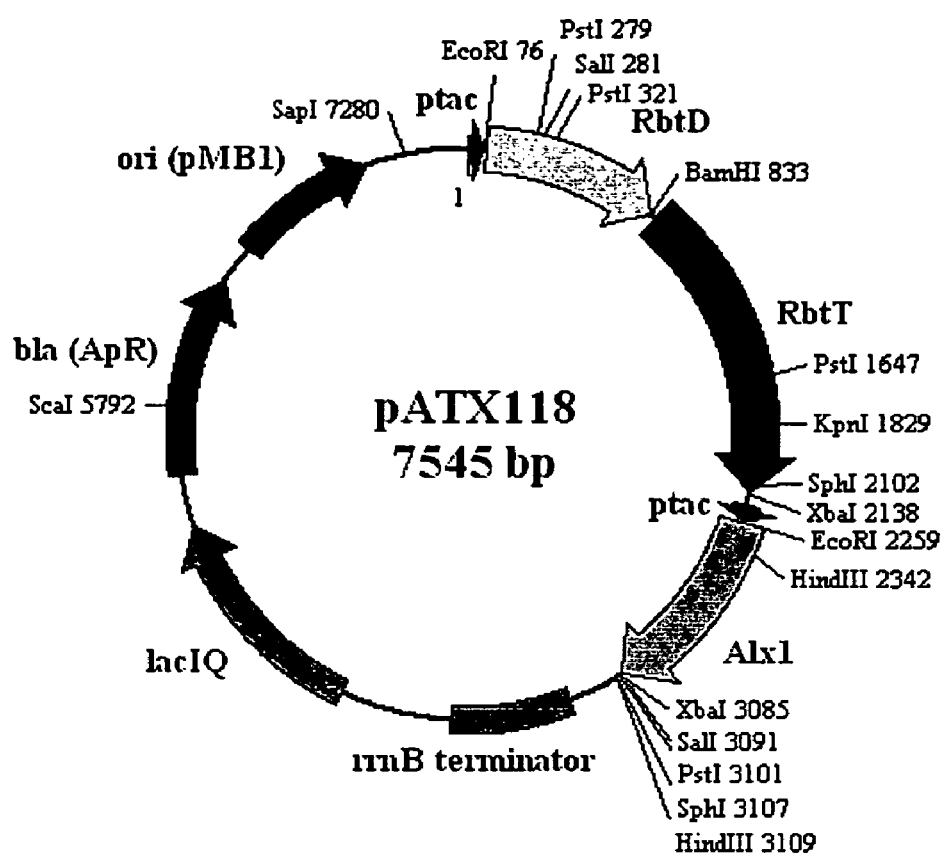
Figure 25. RbtD/RbtT/Alx1 operon cloned into vector pTTQ18.

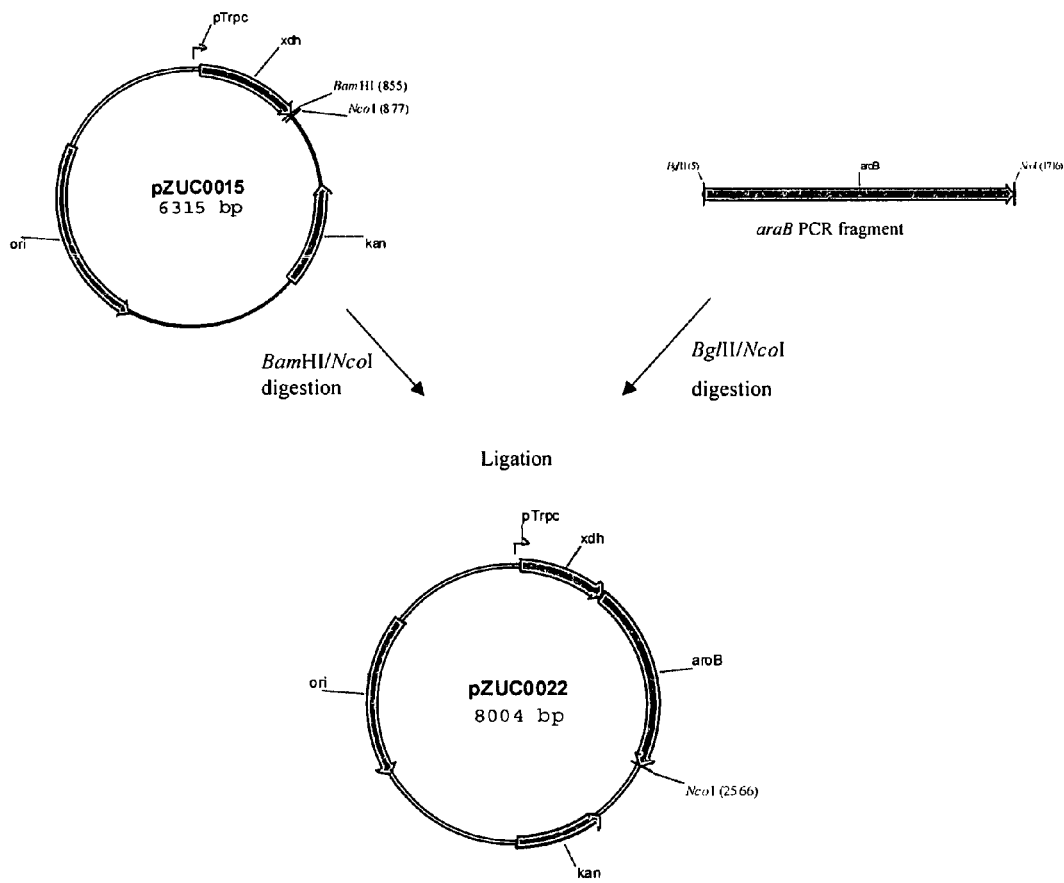
Figure 26. Construction of the xylitol dehydrogenase/L-ribulokinase (*xdh/araB*) operon.

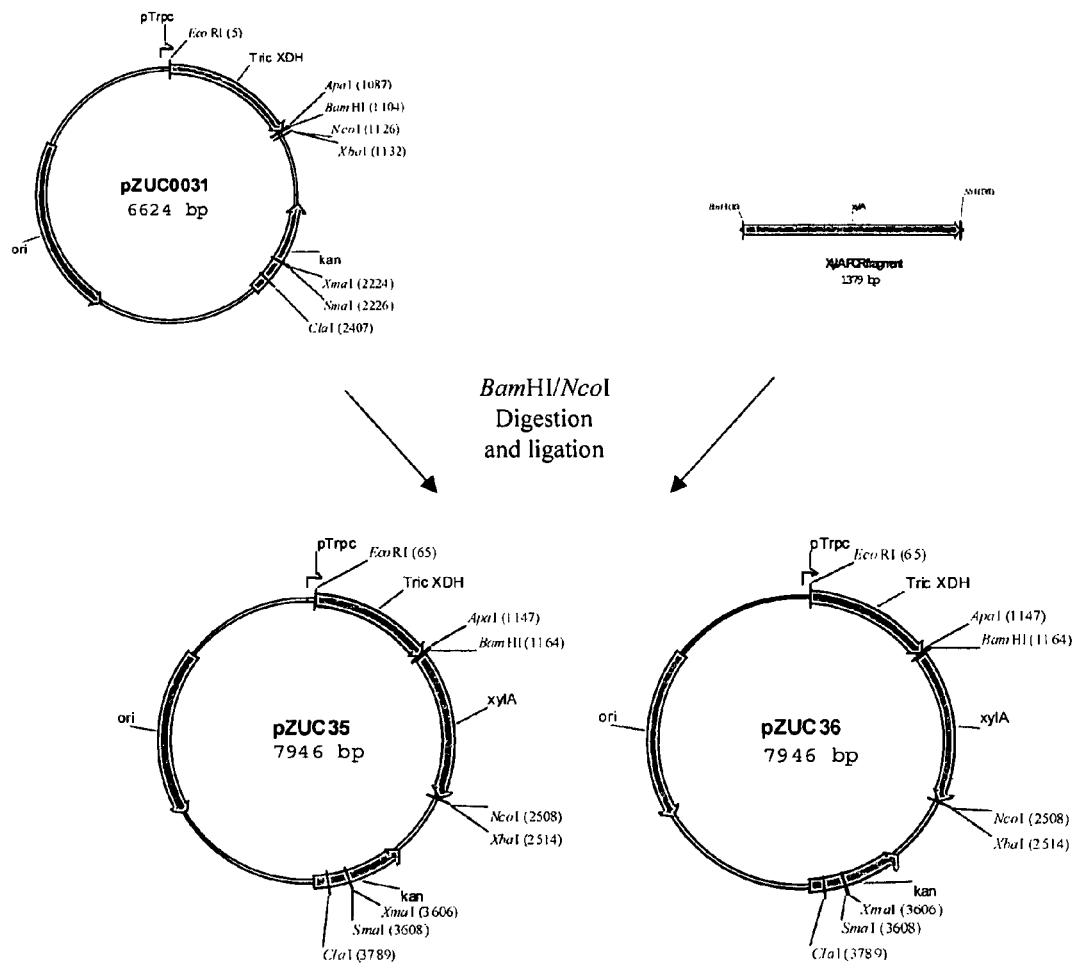
Figure 27. Construction of xylitol dehydrogenase/xylose isomerase (*xdh/xylA*) operon plasmids pZUC35 and pZUC36.

MPSIKLNSGYDMPAVGFGCW
KVDVDTCSEQIYRAIKTGYR
LFDGAEDYANEKLVGAGVKK
AIDEGIVKREDLFLTSKLWN
NYHHPDNVEKALNRTLSDLQ
VDYVDLFLIHFPVTFKFVPL
EEKYPPGFYCGKGDNFDYED
VPILETWKALEKLVKAGKIR
SIGVSNFPGALLLDLLRGAT
IKPSVLQVEHHPYLQQPRLI
EFAQSRGIAVTAYSSFGPQS
FVELNQGRALNTPPLFENET
IKAIAAKHGKSPAQVLLRWS
SQRGIAIIPKSNTVPRLLEN
KDVNSLDLDEQDFADIAKLD
INLRFNDPWDWDKIPIFV

Figure 28. SEQ ID NO:43

MSASIPDIKLSSGHLMPSIG
FGCWKLANATASEQVYQAIK
AGYRLFDGAEDYGNEKEVGD
GVKRAIDEGLVKREEIFLTS
KLWNNYHDPKNVETALNKTL
ADLKVDYVDLFLIHFPIAFK
FVPIEEKYPPGFYCGDGDNF
VYEDVPILETWKALEKLVAA
GKIKSIGVSNFPGALLLDLL
RGATIKPAVLQVEHHPYLQQ
PKLIEFAQKAGVTITAYSSF
GPQSFVEMNQGRALNTPTLF
AHDTIKAIAAKYNKTPAEVL
LRWAAQRGIAVIPKSNLPER
LVQNRSFNTFDLTKEDFEEI
AKLDIGLRFNDPWDWDNIPI
FV

Figure 29. SEQ ID NO:44

SEQUENCE LISTING

<160> NUMBER OF SEQ ID NOS: 44

<210> SEQ ID NO 1
<211> LENGTH: 33
<212> TYPE: DNA
<213> ORGANISM: Pichia stipitis

```
<400> SEQUENCE: 1
gtgtgtgtca tatgccttct attaagttga act                          33

<210> SEQ ID NO 2
<211> LENGTH: 34
<212> TYPE: DNA
<213> ORGANISM: Pichia stipitis

<400> SEQUENCE: 2
gtgtggatcc ttagacgaag ataggaatct tgtc                         34

<210> SEQ ID NO 3
<211> LENGTH: 31
<212> TYPE: DNA
<213> ORGANISM: Escherichia coli

<400> SEQUENCE: 3
gtgtgaattc gatggctatc cctgcatttg g                            31

<210> SEQ ID NO 4
<211> LENGTH: 30
<212> TYPE: DNA
<213> ORGANISM: Escherichia coli

<400> SEQUENCE: 4
cacaggatcc ctaatcccat tcaggagcca                              30

<210> SEQ ID NO 5
<211> LENGTH: 32
<212> TYPE: DNA
<213> ORGANISM: Candida tenuis

<400> SEQUENCE: 5
gagagaattc gatgagcgca agtatcccag ac                           32

<210> SEQ ID NO 6
<211> LENGTH: 34
<212> TYPE: DNA
<213> ORGANISM: Candida tenuis

<400> SEQUENCE: 6
gagaggatcc ttaaacgaag attcgaatgt tgtc                         34

<210> SEQ ID NO 7
<211> LENGTH: 31
<212> TYPE: DNA
<213> ORGANISM: Trichoderma reesei

<400> SEQUENCE: 7
gtgtgaattc gatgtcgcct tccgcagtcg a                            31

<210> SEQ ID NO 8
<211> LENGTH: 34
<212> TYPE: DNA
<213> ORGANISM: Trichoderma reesei

<400> SEQUENCE: 8
gtgtggatcc tcaatccagg ctctgaatca tgac                         34

<210> SEQ ID NO 9
<211> LENGTH: 31
<212> TYPE: DNA
<213> ORGANISM: Trichoderma reesei
```

```
<400> SEQUENCE: 9
gtgtgaattc gatgcctcag cctgtcccca c                                    31

<210> SEQ ID NO 10
<211> LENGTH: 34
<212> TYPE: DNA
<213> ORGANISM: Trichoderma reesei

<400> SEQUENCE: 10
gtgtggatcc ttatcgtgta gtgtaacctc cgtc                                 34

<210> SEQ ID NO 11
<211> LENGTH: 32
<212> TYPE: DNA
<213> ORGANISM: Trichoderma reesei

<400> SEQUENCE: 11
gtgtgaattc gatggcgact caaacgatca ac                                   32

<210> SEQ ID NO 12
<211> LENGTH: 30
<212> TYPE: DNA
<213> ORGANISM: Trichoderma reesei

<400> SEQUENCE: 12
cacaggatcc ttacaccttc tcgttgggcc                                      30

<210> SEQ ID NO 13
<211> LENGTH: 34
<212> TYPE: DNA
<213> ORGANISM: Escherichia coli

<400> SEQUENCE: 13
tataagctta aggaggatcc attatggagt tcaa                                 34

<210> SEQ ID NO 14
<211> LENGTH: 34
<212> TYPE: DNA
<213> ORGANISM: Escherichia coli

<400> SEQUENCE: 14
tcgaagctta gatctccatg gttatttgtc gaac                                 34

<210> SEQ ID NO 15
<211> LENGTH: 44
<212> TYPE: DNA
<213> ORGANISM: Trichoderma reesei

<400> SEQUENCE: 15
tgctctagat aaggaggata taaatgcct cagcctgtcc ccac                       44

<210> SEQ ID NO 16
<211> LENGTH: 44
<212> TYPE: DNA
<213> ORGANISM: Trichoderma reesei

<400> SEQUENCE: 16
tgctctagat aaggaggata taaatgcct cagcctgtcc ccac                       44

<210> SEQ ID NO 17
<211> LENGTH: 45
<212> TYPE: DNA
<213> ORGANISM: Trichoderma reesei
```

```
<400> SEQUENCE: 17
tcggatccta aggaggatat ataatgtcgc cttccgcagt cgatg          45

<210> SEQ ID NO 18
<211> LENGTH: 33
<212> TYPE: DNA
<213> ORGANISM: Trichoderma reesei

<400> SEQUENCE: 18
agctctagat caatccaggc tctgaatcat gac                       33

<210> SEQ ID NO 19
<211> LENGTH: 20
<212> TYPE: DNA
<213> ORGANISM: Gluconobacter oxydans

<400> SEQUENCE: 19
cagcgatgaa ttcgaagaag                                      20

<210> SEQ ID NO 20
<211> LENGTH: 28
<212> TYPE: DNA
<213> ORGANISM: Gluconobacter oxydans

<400> SEQUENCE: 20
agcggatcct taaccgccag caatcggc                             28

<210> SEQ ID NO 21
<211> LENGTH: 60
<212> TYPE: DNA
<213> ORGANISM: Escherichia coli

<400> SEQUENCE: 21
ccaatattac gacatcatcc atcacccgcg gcattacctg gtgtaggctg gagctgcttc    60

<210> SEQ ID NO 22
<211> LENGTH: 60
<212> TYPE: DNA
<213> ORGANISM: Escherichia coli

<400> SEQUENCE: 22
taccgataac cgggccaacg gactgcacag ttagccgtta catatgaata tcctccttag    60

<210> SEQ ID NO 23
<211> LENGTH: 28
<212> TYPE: DNA
<213> ORGANISM: Escherichia coli

<400> SEQUENCE: 23
agcgaattca tgacgcaata ctggctgg                             28

<210> SEQ ID NO 24
<211> LENGTH: 32
<212> TYPE: DNA
<213> ORGANISM: Escherichia coli

<400> SEQUENCE: 24
atcggatcct tataatgtgt gctccttaat gc                        32

<210> SEQ ID NO 25
<211> LENGTH: 31
<212> TYPE: DNA
<213> ORGANISM: Escherichia coli
```

```
<400> SEQUENCE: 25
tctagatcta atatgttgtc caaacaaatc c                              31

<210> SEQ ID NO 26
<211> LENGTH: 29
<212> TYPE: DNA
<213> ORGANISM: Escherichia coli

<400> SEQUENCE: 26
gcaccatggt tacttctgcc cgtaataag                                 29

<210> SEQ ID NO 27
<211> LENGTH: 29
<212> TYPE: DNA
<213> ORGANISM: Ambrosiozyma monospora

<400> SEQUENCE: 27
gcgaattcga tgactgacta cattccaac                                 29

<210> SEQ ID NO 28
<211> LENGTH: 27
<212> TYPE: DNA
<213> ORGANISM: Ambrosiozyma monospora

<400> SEQUENCE: 28
gagggatccc taccaagaag tgaaacc                                   27

<210> SEQ ID NO 29
<211> LENGTH: 42
<212> TYPE: DNA
<213> ORGANISM: Ambrosiozyma monospora

<400> SEQUENCE: 29
gcggatccat aaaggaggat atataatgac tgactacatt cc                  42

<210> SEQ ID NO 30
<211> LENGTH: 35
<212> TYPE: DNA
<213> ORGANISM: Ambrosiozyma monospora

<400> SEQUENCE: 30
gctctagact accaagaagt gaaaccacca tcaac                          35

<210> SEQ ID NO 31
<211> LENGTH: 25
<212> TYPE: DNA
<213> ORGANISM: Pichia stipitis

<400> SEQUENCE: 31
gcggatcccg acatcataac ggttc                                     25

<210> SEQ ID NO 32
<211> LENGTH: 32
<212> TYPE: DNA
<213> ORGANISM: Pichia stipitis

<400> SEQUENCE: 32
gcggatcctt agacgaagat aggaatcttg tc                             32

<210> SEQ ID NO 33
<211> LENGTH: 30
<212> TYPE: DNA
<213> ORGANISM: Klebsiella pneumoniae
```

```
<400> SEQUENCE: 33
gcggaattcg atgaagcact ctgtctcctc                                   30

<210> SEQ ID NO 34
<211> LENGTH: 27
<212> TYPE: DNA
<213> ORGANISM: Klebsiella pneumoniae

<400> SEQUENCE: 34
cgggatcctc agagatccac gctgttc                                      27

<210> SEQ ID NO 35
<211> LENGTH: 42
<212> TYPE: DNA
<213> ORGANISM: Klebsiella pneumoniae

<400> SEQUENCE: 35
gcggatccta aggaggatat attatgtccg ttaataacaa ac                     42

<210> SEQ ID NO 36
<211> LENGTH: 27
<212> TYPE: DNA
<213> ORGANISM: Klebsiella pneumoniae

<400> SEQUENCE: 36
gctctagatt aagactctgc cgcgttg                                      27

<210> SEQ ID NO 37
<211> LENGTH: 28
<212> TYPE: DNA
<213> ORGANISM: Ambrosiozyma monospora

<400> SEQUENCE: 37
gcctctagac gacatcataa cggttctg                                     28

<210> SEQ ID NO 38
<211> LENGTH: 24
<212> TYPE: DNA
<213> ORGANISM: Escherichia coli

<400> SEQUENCE: 38
ttcagatcta acgatggcga ttgc                                         24

<210> SEQ ID NO 39
<211> LENGTH: 30
<212> TYPE: DNA
<213> ORGANISM: Escherichia coli

<400> SEQUENCE: 39
gcaccatggt tatagagtcg caacggcctg                                   30

<210> SEQ ID NO 40
<211> LENGTH: 25
<212> TYPE: DNA
<213> ORGANISM: Escherichia coli

<400> SEQUENCE: 40
cgaactagtt aacttttacg caagt                                        25

<210> SEQ ID NO 41
<211> LENGTH: 22
<212> TYPE: DNA
<213> ORGANISM: Escherichia coli
```

-continued

```
<400> SEQUENCE: 41
ggctgaaaat cttctctcat cc                                              22

<210> SEQ ID NO 42
<211> LENGTH: 22
<212> TYPE: DNA
<213> ORGANISM: Escherichia coli

<400> SEQUENCE: 42
ggctgaaaat cttctctcat cc                                              22

<210> SEQ ID NO 43
<211> LENGTH: 318
<212> TYPE: PRT
<213> ORGANISM: Pichia stipitis

<400> SEQUENCE: 43

Met Pro Ser Ile Lys Leu Asn Ser Gly Tyr Asp Met Pro Ala Val Gly
 1               5                  10                  15

Phe Gly Cys Trp Lys Val Asp Val Asp Thr Cys Ser Glu Gln Ile Tyr
                20                  25                  30

Arg Ala Ile Lys Thr Gly Tyr Arg Leu Phe Asp Gly Ala Glu Asp Tyr
            35                  40                  45

Ala Asn Glu Lys Leu Val Gly Ala Gly Val Lys Lys Ala Ile Asp Glu
        50                  55                  60

Gly Ile Val Lys Arg Glu Asp Leu Phe Leu Thr Ser Lys Leu Trp Asn
 65                  70                  75                  80

Asn Tyr His His Pro Asp Asn Val Glu Lys Ala Leu Asn Arg Thr Leu
                 85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Pro Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Leu Asp Leu
        275                 280                 285
```

-continued

Asp Glu Gln Asp Phe Ala Asp Ile Ala Lys Leu Asp Ile Asn Leu Arg
        290                 295                 300

Phe Asn Asp Pro Trp Asp Trp Asp Lys Ile Pro Ile Phe Val
305                 310                 315

<210> SEQ ID NO 44
<211> LENGTH: 322
<212> TYPE: PRT
<213> ORGANISM: Candida tenuis

<400> SEQUENCE: 44

Met Ser Ala Ser Ile Pro Asp Ile Lys Leu Ser Ser Gly His Leu Met
1               5                   10                  15

Pro Ser Ile Gly Phe Gly Cys Trp Lys Leu Ala Asn Ala Thr Ala Ser
            20                  25                  30

Glu Gln Val Tyr Gln Ala Ile Lys Ala Gly Tyr Arg Leu Phe Asp Gly
        35                  40                  45

Ala Glu Asp Tyr Gly Asn Glu Lys Glu Val Gly Asp Gly Val Lys Arg
50                  55                  60

Ala Ile Asp Glu Gly Leu Val Lys Arg Glu Glu Ile Phe Leu Thr Ser
65                  70                  75                  80

Lys Leu Trp Asn Asn Tyr His Asp Pro Lys Asn Val Glu Thr Ala Leu
                85                  90                  95

Asn Lys Thr Leu Ala Asp Leu Lys Val Asp Tyr Val Asp Leu Phe Leu
            100                 105                 110

Ile His Phe Pro Ile Ala Phe Lys Phe Val Pro Ile Glu Glu Lys Tyr
        115                 120                 125

Pro Pro Gly Phe Tyr Cys Gly Asp Gly Asp Asn Phe Val Tyr Glu Asp
130                 135                 140

Val Pro Ile Leu Glu Thr Trp Lys Ala Leu Glu Lys Leu Val Ala Ala
145                 150                 155                 160

Gly Lys Ile Lys Ser Ile Gly Val Ser Asn Phe Pro Gly Ala Leu Leu
                165                 170                 175

Leu Asp Leu Leu Arg Gly Ala Thr Ile Lys Pro Ala Val Leu Gln Val
            180                 185                 190

Glu His His Pro Tyr Leu Gln Gln Pro Lys Leu Ile Glu Phe Ala Gln
        195                 200                 205

Lys Ala Gly Val Thr Ile Thr Ala Tyr Ser Ser Phe Gly Pro Gln Ser
210                 215                 220

Phe Val Glu Met Asn Gln Gly Arg Ala Leu Asn Thr Pro Thr Leu Phe
225                 230                 235                 240

Ala His Asp Thr Ile Lys Ala Ile Ala Ala Lys Tyr Asn Lys Thr Pro
                245                 250                 255

Ala Glu Val Leu Leu Arg Trp Ala Ala Gln Arg Gly Ile Ala Val Ile
            260                 265                 270

Pro Lys Ser Asn Leu Pro Glu Arg Leu Val Gln Asn Arg Ser Phe Asn
        275                 280                 285

Thr Phe Asp Leu Thr Lys Glu Asp Phe Glu Glu Ile Ala Lys Leu Asp
290                 295                 300

Ile Gly Leu Arg Phe Asn Asp Pro Trp Asp Trp Asp Asn Ile Pro Ile
305                 310                 315                 320

Phe Val

METHODS FOR PRODUCTION OF XYLITOL IN MICROORGANISMS

PRIORITY

This application claims priority to U.S. application Ser. No. 11/133,025, filed May 19, 2005. This application also claims the benefit of U.S. Provision Application Ser. Nos. 60/572,588, filed May 19, 2004; 60/620,173, filed Oct. 18, 2004; and 60/572,438, filed May 19, 2004, all of which are incorporated by reference herein in their entirety.

FIELD OF THE INVENTION

The invention is in the field of constructing effective biosynthetic routes to xylitol production that do not require pure D-xylose for synthesis and that can utilize inexpensive substrates such as hemicellulose hydrolysates.

BACKGROUND OF THE INVENTION

Xylitol is currently produced by chemical hydrogenation of xylose purified from xylan hydrolysates. The use of microorganisms to produce xylitol and other polyols from inexpensive starting materials such as corn and other agricultural byproduct and waste streams has long been thought to be able to significantly reduce production costs for these polyols as compared to chemical hydrogenation. Such a process would reduce the need for purified xylose, produce purer, easier to separate product, and be adaptable to a wide variety of raw materials from different geographic locations.

Despite a significant amount of work, development of a commercially feasible microbial production process has remained elusive for a number of reasons. To date, even with the advent of genetically engineered yeast strains, the volumetric productivity of the strains developed do not reach the levels necessary for a commercially viable process.

Xylitol is currently produced from plant materials—specifically hemicellulose hydrolysates. Different plant sources contain different percentages of cellulose, hemicellulose, and lignin making most of them unsuitable for xylitol production. Because of purity issues, only the hydrolysate from birch trees is used for xylitol production. Birch tree hydrolysate is obtained as a byproduct of the paper and pulping industry, where lignins and cellulosic components have been removed. Hydrolysis of other xylan-rich materials, such as trees, straws, corncobs, oat hulls under alkaline conditions also yields hemicellulose hydrolysate, however these hydrolysates contain many competing substrates. One of these substrates, L-arabinose is a particular problem to xylitol production because it can be converted to L-arabitol, which is practically impossible to separate from xylitol in a cost effective way.

D-xylose in the hydrolysate is converted to xylitol by catalytic reduction. This method utilizes highly specialized and expensive equipment for the high pressure (up to 50 atm) and temperature (80-140° C.) requirements as well as the use of Raney-Nickel catalyst that can introduce nickel into the final product. There have been several processes of this type described previously, for example U.S. Pat. Nos. 3,784,408, 4,066,711, 4,075,406, 4,008,285, and 3,586,537. In addition, the xylose used for the chemical reduction must be substantially purified from lignin and other cellulosic components of the hemicellulose hydrolysate to avoid production of extensive by-products during the reaction.

The availability of the purified birch tree hydrolysate starting material severely limits the xylitol industry today. If a specific, efficient reduction process could be developed that could convert xylose and arabinose to xylitol, but not reduce any other impurities that were present in a starting mixture, then a highly cost competitive process could be developed that would allow significant expansion of the xylitol market.

Many of the prior art methods of producing xylitol use purified D-xylose as a starting material and will also generally convert L-arabinose to L-arabitol (and other sugars to their respective reduced sugar polyol). While there has been a significant amount of work on the development of an organism to convert D-xylose to xylitol, none of the prior art approaches have been commercially effective. There are several reasons for this. First, D-xylose utilization is often naturally inhibited by the presence of glucose that is used as a preferred carbon source for many organisms. Second, none of the enzymes involved have been optimized to the point of being cost effective. Finally, D-xylose in its pure form is expensive. Prior art methods do not address the need for alternative starting materials. Instead they require relatively pure D-xylose. Agricultural waste streams are considered to be the most cost-effective source of xylose. These waste streams are generally mixed with a variety of other hemicellulosic sugars (L-arabinose, galactose, mannose, and glucose), which all affect xylitol production by the microbes in question. See, Walthers et al. (2001). "Model compound studies: influence of aeration and hemicellulosic sugars on xylitol production by *Candida tropicalis*." Appl Biochem Biotechnol 91-93:423-35. However, if an organism can be engineered to utilize more than one of the sugars in the waste stream, it would make the process much more cost effective.

In addition to xylose, L-arabinose is an abundant sugar found in hemicellulose ranging from 5% to 20% depending on the source. Co-conversion of L-arabinose to xylitol or cell biomass would allow a greater variety of starting materials to be used (birch has very low arabinose content and thus does not lead to production of L-arabitol during the chemical hydrogenation). Therefore, methods of converting xylose and arabinose to xylitol, converting xylose and arabinose to xylitol while the arabinose remains unconverted, and converting xylose to xylitol and arabinose to biomass would be desirable.

A variety of approaches have been reported in the literature for the biological production of xylitol. While some basic research has been performed, development of an effective bioprocess for the production of xylitol has been elusive. Many of the systems described below suffer from problems such as poor strain performance, low volumetric productivity, and too broad of a substrate range. Of these, yeasts, primarily *Candida*, have been shown to be the best producers of xylitol from pure D-xylose. See, Hahn-Hagerdal, et al., Biochemistry and physiology of xylose fermentation by yeasts. Enzyme Microb. Technol., 1994. 16:933-943; Jeffries & Kurtzman, Strain selection, taxonomy, and genetics of xylose-fermenting yeasts. Enzyme Microb. Technol., 1994. 16:922-932; Kern, et al., Induction of aldose reductase and xylitol dehydrogenase activities in *Candida tenuis* CBS 4435. FEMS Microbiol Lett, 1997. 149(1):31-7; Saha & Bothast, Production of xylitol by *Candida peltata*. J Ind Microbiol Biotechnol, 1999. 22(6):633-636; Saha & Bothast, Microbial production of xylitol, in Fuels and Chemicals from Biomass, Saha, Editor. 1997, American Chemical Society. p. 307-319. These include *Candida* strains *C. guilliermondii, C. tropicalis, C. peltata, C. milleri, C. shehatae, C. boidinii,* and *C. parapsilosis. C. guillermondii* is one of the most studied organisms and has been shown to have a yield of up-to 75% (g/g) xylitol from a 300 g/l fermentation mixture of xylose. See, Saha & Bothast, *Production of xylitol by Candida peltata*. J Ind Microbiol Biotechnol, 1999. 22(6):633-636. C. tropicalis has also been shown to be a relatively high producer with a cell recycling system producing an 82% yield with a volumetric productivity of 5 g $L^{-1}$ $h^{-1}$ and a substrate concentration of 750 g/l. All of these studies however, were carried out using purified D-xylose as substrate.

Bolak Co., Ltd, of Korea describes a two-substrate fermentation with *C. tropicalis* ATCC 13803 using glucose for cell growth and xylose for xylitol production. The optimized fed-batch fermentation resulted in 187 g $L^{-1}$ xylitol concentration, 75% g/g xylitol/xylose yield and 3.9 g xylitol $L^{-1}$ $H^{-1}$ volumetric productivity. See, Kim et al., *Optimization of fed-batch fermentation for xylitol production by Candida tropicalis*. J Ind Microbiol Biotechnol, 2002. 29(1):16-9. The range of xylose concentrations in the medium ranged from 100 to 200 g $L^{-1}$ total xylose plus xylitol concentration for maximum xylitol production rate and xylitol yield. Increasing the concentrations of xylose and xylitol beyond this decreased the rate and yield of xylitol production and the specific cell growth rate, and the authors speculate that this was probably due to the increase in osmotic stress. Bolak disclosed this approach to xylitol production. See e.g., U.S. Pat. No. 5,998,181; U.S. Pat. No. 5,686,277. They describe a method of production using a novel strain of *Candida tropicalis* KCCM 10122 with a volumetric productivity in 3 to 5 L reactions ranging from 3.0 to 7.0 g xylitol $L^{-1}$ $H^{-1}$, depending on reaction conditions. They also describe a strain, *Candida parapsilosis* DCCM-10088, which can transform xylose to xylitol with a maximum volumetric productivity of 4.7 g xylitol $L^{-1}$ $H^{-1}$, again in bench scale fermentation ranging from 3 to 5 liters in size. While *C. tropicalis* has had moderate success in achieving relatively large levels of xylitol production than the other strains, it suffers from the fact that it is an opportunistic pathogen, and therefore is not suitable for food production and the enzyme also makes L-arabitol from L-arabinose.

One promising approach that has only been moderately explored is the creation of recombinant strains capable of producing xylitol. Xyrofin has disclosed a method involving the cloning of a xylose reductase gene from certain yeasts and transferring the gene into a *Saccharomyces cerevisiae*. See, U.S. Pat. No. 5,866,382. The resulting recombinant yeast is capable of reducing xylose to xylitol both in vivo and in vitro. An isolated enzyme system combining xylitol reductase with formate dehydrogenase to recycle the NADH cofactor during the reaction has been described. In this instance, the enzymatic synthesis of xylitol from xylose was carried out in a fed-batch bioreactor to produce 2.8 g/l xylitol over a 20 hour period yielding a volumetric productivity of about 0.4 g $l^{-1}$ $H^{-1}$. See, Neuhauser et al., *A pH-controlled fed-batch process can overcome inhibition by formate in NADH-dependent enzymatic reductions using formate dehydrogenase-catalyzed coenzyme regeneration*. Biotechnol Bioeng, 1998. 60(3):277-82. The use of this on a large scale using crude substrate has yet to be demonstrated and poses several technical hurdles.

Several methods for producing xylitol from xylose-rich lignocellulosic hydrolyzates through fermentative processes have been described. Xyrofin discloses a method for the production of substantially pure xylitol from an aqueous xylose solution. See, U.S. Pat. No. 5,081,026; U.S. Pat. No. 5,998, 607. This solution may also contain hexoses such as glucose. The process uses a yeast strain to convert free xylose to xylitol while the free hexoses are converted to ethanol. The yeast cells are removed from the fermentation by filtration, centrifugation or other suitable methods, and ethanol is removed by evaporation or distillation. Chromatographic separation is used to for final purification. The process is not commercially viable because it requires low arabinose wood hydrolyzate to prevent L-arabitol formation and the total yield was (95 g $l^{-1}$) and volumetric productivity is low (1.5 g $l^{-1}$ $H^{-1}$). Xyrofin also discloses a method for xylitol synthesis using a recombinant yeast (*Zygosaccharomyces rouxii*) to convert D-arabitol to xylitol. See, U.S. Pat. No. 5,631,150. The recombinant yeast contained genes encoding D-arbinitol dehydrogenase (E.C. 1.1.1.11) and xylitol dehydrogenase (E.C. 1.1.1.9), making them capable of producing xylitol when grown on carbon sources other than D-xylulose or D-xylose. The total yield (15 g $l^{-1}$) and volumetric productivity (0.175 g $l^{-1}$ $H^{-1}$) coupled with the use of D-arabitol as starting material make this route highly unlikely to succeed. Additionally, a 2-step fermentation of glucose to D-arabitol followed by fermentation of D-arabitol to xylitol has also been described. See, U.S. Pat. No. 5,631,150; U.S. Pat. No. 6,303,353; U.S. Pat. No. 6,340,582. However, a two-step fermentation is not economically feasible.

Another method of making xylitol using yeasts with modified xylitol metabolism has been described. See, U.S. Pat. No. 6,271,007. The yeast is capable of reducing xylose and using xylose as the sole carbon source. The yeast have been genetically modified to be incapable or deficient in their expression of xylitol dehydrogenase and/or xylulose kinase activity, resulting in an accumulation of xylitol in the medium. A major problem with this method is that a major proportion of the D-xylose is consumed for growth rather than being converted to the desired product, xylitol.

A process describing the production of xylitol from D-xylulose by immobilized and washed cells of *Mycobacterium smegmatis* has been described. See, Izumori & Tuzaki, *Production of Xylitol from D-Xylulose br Mycobacterium smegmatis*. J. Ferm. Tech., 1988. 66(1):33-36. Modest titers of ~15 g $l^{-1}$ $H^{-1}$ were obtained with a 70% conversion efficiency of D-xylulose into xylitol. Also disclosed was the conversion of D-xylose into xylitol by using a combination of commercially available, immobilized xylose isomerase and *M. smegmatis* cells containing xylitol dehydrogenase activity. It was found that xylitol inhibition of the xylose isomerase caused the incomplete conversion of D-xylose into xylitol. This process does not teach how one could relieve the inhibition of the xylose isomerase by xylitol or how one would engineer a single strain to convert D-xylose into xylitol.

Ajinomoto has several patents/patent applications concerning the biological production of xylitol. In U.S. Pat. No. 6,340,582, they claim a method for producing xylitol with a microorganism containing D-arbinitol dehydrogenase activity and D-xylulose dehydrogenase activity. This allows the organisms to convert D-arabitol to D-xylulose and the D-xylulose to xylitol, with an added carbon source for growth. Sugiyama further develops this method in U.S. Pat. No. 6,303,353 with a list of specific species and genera that are capable of performing this transforming, including *Gluconobacter* and *Acetobacter* species. This work is furthered by the disclosure of the purified and isolated genes for two kinds of xylitol dehydrogenase from *Gluconobacter oxydans* and the DNA and amino acid sequences, for use in producing xylitol from D-xylulose. See, U.S. Pat. Publ. 2001/0034049; U.S. Pat. No. 6,242,228. In US Appl. Publ. No. 2003/0148482 they further claim a microorganism engineered to contain a xylitol dehydrogenase, that has an ability to supply reducing power with D-xylulose to produce xylitol, particularly in a microorganism that has an ability to convert D-arbinitol into D-xylulose.

Ajinomoto has also described methods of producing xylitol from glucose. Takeuchi et al. in U.S. Pat. No. 6,221,634 describes a method for producing either xylitol or D-xylulose from *Gluconobacter*, *Acetobacter* or *Frateuria* species from glucose. However, yields of xylitol were less than 1%. Mihara et al. further claim specific osmotic stress resistant *Gluconobacter* and *Acetobacter* strains for the production of xylitol and xylulose from the fermentation of glucose. See, U.S. Pat. No. 6,335,177. They report a 3% yield from a 20% glucose fermentation broth. In U.S. Pat. Appl. No. 2002/0061561, Mihara et al. claim further discovered strains, also with yields of only a few percent. See, U.S. Pat. No. 6,335,177.

Cerestar has disclosed a process of producing xylitol from a hexose such as glucose in two steps. See, U.S. Pat. No. 6,458,570. The first step is the fermentative conversion of a hexose to a pentitol, for example, glucose to arabitol, and the second step is the catalytic chemical isomerisation of the pentitol to xylitol.

Bley et al. disclose a method for the biotechnological production of xylitol using microorganisms that can metabolize xylose to xylitol. See, WO03/097848. The method comprises the following steps: a) microorganisms are modified such that oxidation of NADH by enzymes other than the xylose reductase is reduced or excluded; b) the microorganisms are cultivated in a substrate containing xylose and 10-40 grams per liter of sulphite salt (e.g. calcium hydrogen sulphite, natrium sulphite, potassium sulphite); c) the microorganisms are cultivated in an aerobic growth phase and an oxygen-limited xylitol production phase; and d) the xylitol is enriched and recovered from the substrate.

Londesborough et al. have disclosed a genetically modified fungus containing L-arabitol 4-dehydrogenase and L-xylulose xylulose reductase. See, U.S. Pat. Appl. Publ. No. 2003/0186402. This application is aimed at producing useful products from biomass containing L-arabinose, which is a major constituent of plant material but does not disclose the use of D-xylose/L-arabinose mixtures for the synthesis of xylitol in procaryotes. Verho et al. also describe and alternative L-xylulose reductase from *Ambrosiozyma monospora* that utilizes NADH as co-factor. See, Verho et al., *New Enzyme for an in vivo and in vitro Utililization of Carbohydrates*. 2004, Valtion Teknillinen Tutki-muskeskus. p. 15.

Researchers at Danisco have developed several xylitol bioprocesses. Heikkila et al. describes a process wherein purified L-xylose is utilized as intermediate. See, U.S. Pat. Appl. Publ. No. 2003/0097029. The application also covers methods of production of L-xylose. This process is not feasible because L-xylose is a rare sugar and is considerably more valuable than the final product. A method for simultaneously producing xylitol as a co-product during fermentative ethanol production, utilizing hydrolyzed lignocellulose-containing material is disclosed in U.S. Pat. Appl. Publ. No. 2003/0235881. This process consists of fermenting the free hexoses to ethanol while the xylose is converted to xylitol with a single yeast strain. The yields, however, of both ethanol and xylitol were relatively poor and require pure D-xylose as a substrate. Danisco has also developed a multiple processes for the preparation of xylitol, all of them utilizing ribulose. See, U.S. Pat. Appl. Publ. No. 2003/0125588. These processes include different conversion reactions, such as reduction, epimerization and/or isomerisation. Xylitol is also produced in the fermentation of glucose in one embodiment. The process can also use ribulose and xylulose as starting material, followed by reduction, epimerization and isomerisation to xylitol. Again the starting substrates D-xylulose and ribulose are more valuable than the final product.

Ojamo et al. shows a method for the production of xylitol involving a pair of microorganisms one having xylanolytic activity, and another capable of converting a pentose sugar to xylitol, or a single microorganism capable of both reactions. See, U.S. Pat. Appl. Publ. No. 2004/0014185. In one embodiment of the invention, two microorganisms are used for the production of xylitol, one microorganism possessing xylanolytic activity and the other possessing the enzymatic activity needed for conversion of a pentose sugar, such as D-xylose and L-arabinose, preferably D-xylose, to xylitol. This method requires a complicated two-organism system and produces mixtures of xylitol and L-arabitol, which need extra purification and recycle steps to improve the xylitol yield. It does not teach simple, single organism methods that can use D-xylose/L-arabinose mixtures to synthesize pure xylitol. Finally, Miasnikov et al. have developed multiple methods for the production of xylitol, five-carbon aldo- and keto-sugars and sugar alcohols by fermentation in recombinant hosts. See, U.S. Pat. Appl. Publ. No. 2003/0068791. These recombinant hosts have been engineered to redirect pentose phosphate pathway intermediates via ribulose-5-P, xylulose-5-P and xylitol-5-P into the production of xylitol, D-arbinitol, D-arabinose, D-xylose, ribitol, D-ribose, D-ribulose, D-xylose, and/or D-xylulose. Methods of manufacturing are disclosed that use such hosts, but the productivity is low.

While clearly there has been a significant amount of work on the development of an organism to convert xylose to xylitol, none of these have resulted in an effective production organism or a commercialized process. The yeast methods described above all require relatively pure xylose as a starting material, since the organisms described will also convert L-arabinose to L-arabitol (and other sugars to their respective reduced sugar pentitol). This results in difficult-to-remove by-products which can only be separated by costly separation methods. Purified xylose is also prohibitively expensive for use in a bioprocess and cannot compete with the current chemical hydrogenation. Several of the processes above consist of more than one fermentation step, which is again, cost-prohibitive. The reported production rate of some of the strains is low, as in the Ajinomoto patents. Above all, none of the enzymes or strains involved has been engineered to be cost effective. If the turnover rate of one or more enzyme can be improved, then the production level would increase. Further, none of the approaches have addressed the problems associated with the use of agricultural hydrolyzates to produce xylitol. Agricultural waste streams are considered to be the most cost-effective source of D-xylose. These waste streams are generally mixed with a variety of other hemicellulosic sugars (arabinose, galactose, mannose, and glucose), which all affect xylitol production by the microbes in question. See, Walthers et al., Model compound studies: influence of aeration and hemicellulosic sugars on xylitol production by Candida tropicalis. Appl Biochem Biotechnol, 2001. 91-93:423-35.

Hence there is an opportunity for a high-specificity bioprocess that is both economical and safe and can utilize alternative starting materials. Table 1 outlines several potential agricultural residues that would be suitable as feedstocks if such a process was available. The instant invention addresses these problems and allows the engineering of an efficient bioprocess for making xylitol.

SUMMARY OF THE INVENTION

One embodiment of the invention provides a recombinant bacterium that expresses proteins comprising xylose reductase, L-arabitol dehydrogenase or ribitol dehydrogenase, or both, and L-xylulose reductase activities, wherein the recombinant bacterium can produce an end-product of xylitol from substrates comprising: D-xylose; or L-arabinose; or L-arabinose and D-xylose; or L-arabinose, D-xylose and other sugars; and wherein no substantial amount of L-arabitol is produced as an end-product. The substrate can be a xylan, hydrolysate or a hemicellulose hydrolysate. The recombinant bacterium can further express a ribitol transporter protein. The bacterium can be *Escherichia coli*. The recombinant bacterium can be non-pathogenic. The bacterium can have an inactive ptsG gene or a missing ptsG gene. The recombinant bacterium can produce L-arabitol or L-xylulose or both as intermediates to the xylitol end-product. The recombinant bacterium can comprise one or more recombinant nucleic acid sequences encoding aldose reductase, L-xylose reductase, ribitol dehydrogenase, ribitol transporter protein, L-arabitol dehydrogenase, and L-xylulose reductase. The nucleic acid sequence encoding xylose reductase can be a *Pichia stipitis* nucleic acid sequence or a yafB or yajO nucleic acid sequence from *E. coli*. The nucleic acid sequence encoding ribitol dehydrogenase can be a *Klebsiella pneumoniae* or *Klebsiella aerogenes* nucleic acid sequence. The nucleic acid sequence encoding L-xylulose reductase can be an *Ambrosioyma monospora* nucleic acid sequence. The nucleic acid sequence encoding L-arabitol dehydrogenase can be a *Trichoderma reesei* nucleic acid sequence. The nucleic acid sequence encoding L-xylose reductase can be a *T. reesei* nucleic acid sequence.

Another embodiment of the invention provides a method for producing a xylitol end-product comprising fermenting a substrate comprising D-xylose; or L-arabinose; or L-arabinose and D-xylose; or L-arabinose, D-xylose and other sugars with a recombinant bacterium comprising xylose reductase, L-arabitol dehydrogenase, and L-xylulose reductase activities, wherein the recombinant bacterium can produce an end-product of xylitol from substrates comprising: D-xylose; or L-arabinose; or L-arabinose and D-xylose; or L-arabinose, D-xylose and other sugars; and wherein no substantial amount of L-arabitol is produced as an end-product. L-arabitol, or L-xylulose or both can be produced as an intermediate to the xylitol end-product. The method does not require separation of L-arabitol from the xylitol end-product.

Yet another embodiment of the invention provides a method for producing L-xylulose comprising fermenting a substrate comprising D-xylose; or L-arabinose; or L-arabinose and D-xylose; or L-arabinose, D-xylose and other sugars with a recombinant bacterium comprising xylose reductase, L-arabitol dehydrogenase, and L-xylulose reductase activities, wherein the recombinant bacterium can produce an end-product of xylitol from substrates comprising: D-xylose; or L-arabinose; or L-arabinose and D-xylose; or L-arabinose, D-xylose and other sugars; and wherein no substantial amount of L-arabitol is produced as an end-product. L-xylulose is collected before it is converted to xylitol.

Still another embodiment of the invention provides a method of producing xylitol from a substrate comprising D-xylose; or L-arabinose; or L-arabinose and D-xylose; or L-arabinose, D-xylose and other sugars. The method comprises contacting the substrate with one or more isolated bacteria that comprise xylose reductase activity, L-arabitol dehydrogenase activity or ribitol dehydrogenase activity or both, and L-xylulose reductase activity, wherein the substrate is converted to an end-product of xylitol and wherein substantially no L-arabitol is produced as an end-product. The one or more bacteria can also comprise ribitol transporter activity.

Even another embodiment of the invention provides a process for producing xylitol from a substrate comprising D-xylose; or L-arabinose; or L-arabinose and D-xylose; or L-arabinose, D-xylose and other sugars. The method comprises contacting the substrate with xylose reductase, L-arabitol dehydrogenase or ribitol dehydrogenase or both, and L-xylulose reductase, wherein the substrate is converted to an endproduct of xylitol and wherein substantially no L-arabitol is produced as an end-product. L-arabitol or L-xylulose or both can be produced as intermediate products. The substrate can be further contacted with ribitol transporter protein.

Yet another embodiment of the invention provides an isolated microorganism comprising xylose specific reductase activity, wherein the xylose specific reductase activity does not convert L-arabinose to L-arabitol. The microorganism can produce an end-product of xylitol from a substrate comprising D-xylose; or L-arabinose; or L-arabinose and D-xylose; or L-arabinose, D-xylose and other sugars. The microorganism can produce no substantial amount of L-arabitol as an end-product. The substrate can be a xylan hydrolysate or hemicellulose hydrolysate. The microorganism can be *E. coli*. The microorganism can have an inactive ptsG gene or a missing ptsG gene. The microorganism can be non-pathogenic. The microorganism can be a bacteria, fungus or yeast. The xylose specific reductase can be encoded by a nucleic acid comprising SEQ ID NO:43.

Another embodiment of the invention provides a method for producing xylitol comprising fermenting a substrate comprising D-xylose; or L-arabinose; or L-arabinose and D-xylose; or L-arabinose, D-xylose and other sugars; with an isolated microorganism comprising xylose specific reductase activity, wherein the xylose specific reductase activity does not convert L-arabinose to L-arabitol. The method does not require separation of L-arabitol from xylitol.

Yet another embodiment of the invention provides a purified xylose specific reductase comprising SEQ ID NO:43. Another embodiment of the invention provides a purified *P. stipitis* xylose reductase comprising a Ser233Pro mutation and a Phe286Leu mutation.

Still another embodiment of the invention provides a process for producing xylitol comprising contacting a substrate comprising D-xylose; or L-arabinose; or L-arabinose and D-xylose; or L-arabinose, D-xylose and other sugars; with a xylose-specific reductase. The xylose-specific reductase can comprise SEQ ID NO:43.

Even another embodiment of the invention provides a recombinant *E. coli* that comprises a nucleic acid sequence encoding xylitol dehydrogenase, wherein the *E. coli* produces substantially no xylose isomerase. The *E. coli* can have an inactive or missing PtsG gene.

Still another embodiment of the invention provides a method of screening for xylose reductase activity. The method comprises transforming a recombinant *E. coli* that comprises a nucleic acid sequence encoding xylitol dehydrogenase, and which produces substantially no xylose isomerase with a nucleic acid molecule encoding a putative xylose reductase to produce a transformant; and adding the transformant to D-xylose minimal media, wherein, if the transformant comprises an expressed nucleic acid encoding a xylose reductase the transformant will grow in the D-xylose minimal media.

Another embodiment of the invention provides a recombinant *E. coli* comprising L-xylulose kinase activity, L-xylulose 5-phosphate epimerase activity, and L-ribulose 5-phosphate 4-epimerase activity. The *E. coli* strain can be strain K12. Another embodiment of the invention provides a recombinant *E. coli* strain comprising a deleted or inactive yiaJ gene. The strain can be *E. coli* K 12.

Even another embodiment of the invention provides a method of screening for L-arabitol dehydrogenase activity or ribitol dehydrogenase activity. The method comprises transforming a recombinant *E. coli* comprising L-xylulose kinase activity, L-xylulose 5-phosphate epimerase activity, and L-ribulose 5-phosphate 4-epimerase activity or a recombinant *E. coli* strain comprising a deleted or inactive yiaJ gene with a nucleic acid molecule encoding a putative L-arabinitol dehydrogenase or ribitol dehydrogenase to produce a transformant, and adding the transformant to L-arabinitol media, wherein if the transformant comprises an expressed nucleic acid encoding a L-arabinitol dehydrogenase, the transformant will grow in the L-arabinitol media.

Still another embodiment of the invention provides an isolated xylose reductase that is active at 37° C. The xylose reductase can retain 90% or more of its activity at 37° C. when compared to its activity at 30° C. The xylose reductase can comprise an amino acid sequence of SEQ ID NO:44. The xylose reductase can comprise a *C. tenuis* xylose reductase that comprises a Gly32Ser mutation and an Asn138Asp mutation.

Yet another embodiment of the invention provides a method for screening for bacteria that cannot utilize L-arabinose. The method comprises transforming bacteria that do not have xylose isomerase activity or an araBAD operon and that have xylitol dehydrogenase activity and L-ribulokinase activity, with a nucleic acid encoding a xylose reductase, wherein if the xylose reductase is a xylose-specific reductase the transformed bacteria cannot utilize L-arabinose and will grow on media comprising L-arabinose and D-xylose, and wherein if the xylose reductase is not a xylose-specific reductase, the transformed bacteria can utilize L-arabinose and will not grow on media comprising L-arabinose and D-xylose.

Even another embodiment of the invention provides an isolated microorganism comprising a recombinant operon comprising a nucleic acid encoding a xylitol dehydrogenase and a nucleic acid encoding a xylose isomerase.

Another embodiment of the invention provides a method of converting D-xylose to xylitol comprising fermenting a substrate comprising D-xylose with an isolated microorganism comprising a recombinant operon comprising a nucleic acid encoding a xylitol dehydrogenase and a nucleic acid encoding a xylose isomerase. D-xylulose can be produced as an intermediate to the xylitol. Greater than 50% of the D-xylose can be converted to xylitol. The microorganism can be a bacterium, such as *E. coli*, a fungus, or a yeast.

Still another embodiment is the selection of a xylose isomerase that is resistant to xylitol and shows enhanced xylitol synthesis when combined in a strain carrying a xylitol dehydrogenase that can not utilize D-xylose. Further, this can be optimally by using a bacterial, fungal or yeast host that has been relived of glucose repression so as all of the sugars in hemicellulose hydrolysate can be utilized during xylitol synthesis.

Another embodiment of the invention provides a purified *E. coli* xylose isomerase (xylA) wherein the amino acid sequence comprises the following mutations:
(a) F9L, L213Q, F283Y, K311R, H420N;
(b) F9L, Q11K, L213Q, F283Y, K311R, H420N;
(c) F9L, Q11K, S20L, L213Q, F283Y, K311R, H420N; or
(d) F9L, Q11K, S20L, L213Q, F283Y, K311R, H420N, H439Q.

Even another embodiment of the invention provides a recombinant microorganism comprising a mutated *E. coli* xylose isomerase coding sequence, wherein the microorganism can grow in the presence of about 1% or more of xylitol.

Therefore, the invention provides compositions and methods for converting xylose and arabinose to xylitol, converting xylose to xylitol while any arabinose present remains unconverted, and converting xylose to xylitol and arabinose to biomass.

BRIEF DESCRIPTION OF THE DRAWINGS

FIG. 1 shows a pathway for xylitol synthesis from, for example, hemicellulose.

FIG. 2 shows the properties of a xylose reductase screening strain.

FIG. 3 shows the properties of a L-Arabitol 4-dehydrogenase screening strain.

FIG. 4 shows the properties of a D-xylose-specific reductase screening strain.

FIG. 5 shows a pathway for production of pure xylitol using hemicellulose substrate.

FIG. 6 shows a pathway for the production of xylitol from D-xylose.

FIG. 7 shows *P. stipitis* xylose reductase cloned into vector pTTQ18.

FIG. 8 shows *E. coli* yafB (xylose reductase) cloned into vector pTTQ18.

FIG. 9 shows *Candida tenuis* XR gene cloned into pTTQ18.

FIG. 10 shows *Trichoderma reesei* L-arabitol 4-dehydrogenase gene cloned into pTTQ18.

FIG. 11 shows *Trichoderma reesei* L-xylulose reductase gene cloned into pTTQ18.

FIG. 12 shows *Trichoderma reesei* xylitol dehydrogenase gene cloned into pTTQ18.

FIG. 13 shows construction of the L-arabitol 4-dehydrogenase/L-xylulose reductase operon.

FIG. 14 shows construction of the XR/LAD1 operon.

FIG. 15 shows construction of the yafB/LAD 1 operon.

FIG. 16 shows construction of an XR/LAD1/LXR operon.

FIG. 17 shows construction of the yafB/LAD1/LXR operon.

FIG. 18 shows *Gluconobacter oxydans* xylitol dehydrogenase (xdh) gene cloned into pTTQ18.

FIG. 19 shows construction of a constitutive L-xylulose degradation pathway in expression vector pTrp338.

FIG. 20 shows *A. monospora* L-xylulose reductase cloned into vector pTTQ18.

FIG. 21 shows Lad1/Alx1 operon cloned into vector pTTQ18.

FIG. 22 shows XR/Lad1/Alx1 operon cloned into vector pTTQ18.

FIG. 23 shows *K. pneumoniae* ribitol dehydrogenase cloned into vector pTTQ18.

FIG. 24 shows RbtD/RbtT operon cloned into vector pTTQ18.

FIG. 25 shows RbtD/RbtT/Alx1 operon cloned into vector pTTQ18.

FIG. 26 shows construction of the xylitol dehydrogenase/L-ribulokinase (xdh/araB) operon.

FIG. 27 shows construction of xylitol dehydrogenase/xylose isomerase (xdh/xylA) operon plasmids pZUC35 and pZUC36.

FIG. 28 shows SEQ ID NO:43.

FIG. 29 shows SEQ ID NO:44.

DETAILED DESCRIPTION OF THE INVENTION

This invention relates to the development of processes, including whole-cell microbial processes, using enzyme systems capable of converting the following:
1) Substrates comprising D-xylose and/or L-arabinose (present in many xylan hydrolysates) mixtures to xylitol;

2) Substrates comprising D-xylose and L-arabinose mixtures wherein the L-arabinose is not converted to L-arabitol.

Xylitol Synthesis from L-Arabinose and D-Xylose

One embodiment of the invention provides a pathway that will produce xylitol from substrate sources comprising both L-arabinose and D-xylose. An example of a pathway for this co-conversion is outlined in FIG. 1. One or more xylose reductases (XR) convert L-arabinose and D-xylose to L-arabitol and xylitol, respectively. One or more L-arabitol dehydrogenases (LAD) or ribitol dehydrogenase (RbtD) convert L-arabitol to L-xylulose. One or more xylulose dehydrogenases (LXR) convert L-xylulose to an end-product of xylitol. Therefore, substantially no L-arabitol is present as an end-product. While some researchers have described a 2-step fermentation of glucose to D-arabitol (not L- as described in the instant approach) followed by fermentation of D-arabitol to xylitol, this two-step process is inherently expensive. See, U.S. Pat. No. 5,631,150; U.S. Pat. No. 6,303,353.

No significant studies at generating a single high-efficiency engineered microbial strain or process for the co-conversion of D-xylose and L-arabinose have been carried out prior to the instant invention.

In one embodiment of the invention the co-conversion of D-xylose and L-arabinose to xylitol occurs by a single recombinant or isolated microorganism. A microorganism can be a bacterium, yeast or fungi. In one embodiment of the invention the host is an *E. coli* strain, such as strain K12. In another embodiment of the invention the microorganism comprises a deleted or inactive PtsG gene. Deleted means that the coding sequence for PtsG is eliminated from the microorganism. Inactive means that the activity of the protein encoded by the gene has less than about 25%, 10%, 5%, or 1% of the wild-type protein. Alternatively, inactive means that the expression of the gene is reduced by about 75%, 90%, 95%, 99% or more as compared to the wild-type gene. In another embodiment of the invention two or more recombinant microorganisms can be used in the co-conversion of D-xylose and L-arabinose to xylitol. Each of the microorganisms can be capable of converting L-arabinose to L-arabitol and D-xylose to xylitol, L-arabitol to L-xylulose, and L-xylulose to xylitol. Alternatively, one or more microorganisms can perform one or more steps of this pathway, while one or more other microorganisms can perform one or more steps of the pathway wherein an end-product of xylitol is produced. Optionally, a mixture of microorganisms that can perform one or more steps of the pathway are used.

Substrates of the invention can comprise D-xylose; or L-arabinose; or L-arabinose and D-xylose; or L-arabinose, D-xylose and other sugars. Examples of substrates include xylan hydrolysate and hemicellulose hydrolysate. Agricultural residues that can be used include, for example, bagasse agricultural residue, corn cob agriculture residue, flax straw agricultural residue, wheat straw residue, oat hull agricultural residue, tree hydrolysate, or a combination thereof.

In one embodiment of the invention a recombinant microorganism possesses one or more xylose reductase, L-arabitol dehydrogenase, ribitol dehydrogenase, ribitol transporter, and L-xylulose reductase activities. These activities can be naturally present in the microorganism (i.e., wild-type) or can be recombinant activities (i.e., a heterologous nucleic acid sequence is added to the microorganism and is expressed by the microorganism). The recombinant microorganism can comprise one or more recombinant nucleic acid sequences encoding, for example, xylose reductase, L-arabitol dehydrogenase, ribitol dehydrogenase, ribitol transporter, and L-xylulose reductase. Methods of making recombinant microorganisms are well known in the art. See e.g., Sambrook et al., Molecular Cloning: A Laboratory Manual, Cold Spring Harbor Laboratory, New York (1989), Current Protocols in Molecular Biology, Ausebel et al. (eds), John Wiley and Sons, Inc. New York (2000). Furthermore, methods of constructing recombinant microorganisms are described in the Examples below.

Xylose reductases generally have broad substrate specificities and function on both D-xylose as well as L-arabinose. See, Hahn-Hagerdal et al. (1994). "Biochemistry and physiology of xylose fermentation by yeasts." Enzyme Microb. Technol. 16: 933-943; Richard et al. (2003). "Production of ethanol from L-arabinose by *Saccharomyces cerevisiae* containing a fungal L-arabinose pathway." FEM Yeast Res 3(2):185-9.

Many sources of xylose reductases are suitable for use. In one embodiment of the invention, a xylose reductase of *Pichia stipitis* is used because its DNA sequence is available, it can use both NADH and NADPH as enzyme cofactor and has good activity on both L-arabinose and D-xylose. Two putative xylose reductases from *E. coli* (yafB and yajO) could also used due to the ease with which they can be cloned and expressed in *E. coli*. XYL1 from *Candida tenuis* can also be used.

Any L-arabitol dehydrogenase or ribitol dehydrogenase (optionally in combination with ribitol transporter) active in a host of the invention to convert L-arabitol to L-xylulose can be used. For example, a lad1 nucleic acid sequence (L-arabitol 4-dehydrogenase) of *Trichoderma reesei* (an asexual clonal derivative of *Hypocrea jecorina*) can be used. See, Richard et al. (2001). "Cloning and expression of a fungal L-arabinitol 4-dehydrogenase gene." J Biol Chem 276(44): 40631-7. L-arabitol dehydrogenases have also been described in *Klebsiella pneumoniae* and *Erwinea* sp. See, Doten & Mortlock (1984). "Directed evolution of a second xylitol catabolic pathway in *Klebsiella pneumoniae*." J Bacteriol 159(2): 730-5; Doten & Mortlock (1985). "Characterization of xylitol-utilizing mutants of *Erwinia uredovora*." J Bacteriol 161(2): 529-33; Doten & Mortlock (1985). "Inducible xylitol dehydrogenases in enteric bacteria." J Bacteriol 162(2):845-8. Additionally, ribitol dehydrogenase (optionally in combination with ribitol transporter) from e.g., *K. pneumoniae* or *K. aerogenes* can be used.

Any L-xylulose reductase active in a host of the invention to convert L-xylulose to xylitol can be used. For example, a lxr1 nucleic acid sequence (L-xylulose reductase) from e.g., *T. reesei* or from *Ambrosiozyma monospora* can be used See, Richard et al. (2002). "The missing link in the fungal L-arabinose catabolic pathway, identification of the L-xylulose reductase gene." Biochemistry 41(20): 6432-7.

Recombinant nucleic acid sequences encoding xylose reductase, L-arabitol dehydrogenase, ribitol dehydrogenase, ribitol transporter, and/or L-xylulose reductase can be either inserted into the chromosome of the host microorganism or be extra-chromosomal under control of either a constitutive or inducible promoter. It would also be advantageous to deregulate specific sugar transport systems thus allowing the simultaneous transport sugars such as D-xylose and L-arabinose while using D-glucose as carbon and energy source. The enzymes can also be enhanced by directed evolution to create a host strain that could be used to create unique, commercially viable processes that will use agriculture waste streams to create a valuable product in a cost effective manner.

Xylitol is the desired end-product of the conversions of the invention. An end-product of a conversion reaction can be defined as a desired product that can accumulate in the growth medium of a producing culture or that can accumulate during a process with a minimal level of catabolism and that can be subsequently recovered.

From the starting substrate materials a recombinant or isolated microorganism of the invention can produce L-arabitol and L-xylulose as intermediate products. An intermediate product can be defined as a product generated from a starting substrate that requires further conversion into an end-product or that can be collected, processed, or removed separately from an end-product. The intermediate products can be collected before their ultimate conversion to xylitol if desired.

The invention provides methods for producing a xylitol end-product comprising fermenting a substrate comprising D-xylose; or L-arabinose; or L-arabinose and D-xylose; or L-arabinose, D-xylose and other sugars with one or more recombinant or isolated microorganisms of the invention. L-arabitol and L-xylulose can be produced as an intermediate to the xylitol end-product. In one embodiment of the invention, the methods do not require separation of L-arabitol from the xylitol end-product because substantially no L-arabitol is produced as an end-product.

One embodiment of the invention provides a process for converting D-xylose; or L-arabinose; or L-arabinose and D-xylose; or L-arabinose, D-xylose and other sugars to xylitol using one or more of xylose reductase, L-arabitol dehydrogenase, ribitol dehydrogenase, ribitol transporter, and L-xylulose reductase enzymes. The process does not have to be performed by a microbial host. For example, enzymes could be added directly to a substrate to convert the substrate to xylitol.

One embodiment of the invention provides a method for producing L-xylulose comprising fermenting a substrate comprising D-xylose; or L-arabinose; or L-arabinose and D-xylose; or L-arabinose, D-xylose and other sugars with one or more recombinant or isolated microorganisms of the invention, and collecting L-xylulose before it is converted to xylitol.

Xylitol Synthesis from L-Arabinose and D-Xylose: D-Xylose Specific Xylose Reductases In one embodiment of the invention substrates comprising D-xylose; or L-arabinose; or L-arabinose and D-xylose; or L-arabinose, D-xylose and other sugars are converted to xylitol using a D-xylose-specific xylose reductase that can convert D-xylose to xylitol but cannot convert L-arabinose to L-arabitol. Such a pathway would allow the use of inexpensive starting substrates (see e.g., Table 1). Furthermore, a recombinant microorganism host can be engineered to use the other sugars in this material as carbon and energy sources thus increasing the overall efficiency by simply deregulating the specific sugar degradation pathways. This disclosure represents the first report of D-xylose-specific xylose reductases. All of the xylose reductases disclosed to date exhibit activity on both D-xylose and L-arabinose.

One embodiment of the invention provides a process for converting substrates comprising D-xylose; or L-arabinose; or L-arabinose and D-xylose; or L-arabinose, D-xylose and other sugars to xylitol using a D-xylose-specific xylose reductase that can convert D-xylose to xylitol but cannot convert L-arabinose to L-arabitol. The process does not have to performed by a microbial host. For example, enzymes could be added directly to a substrate to convert the substrate to xylitol.

In one embodiment of the invention a xylose-specific reductase is a P. stipitis XR gene that has the following mutations: Ser233Pro and Phe286Leu. This mutant can be improved by directed evolution using iterative mutagenesis and screening for growth on media with increasing concentrations of L-arabinose.

One embodiment of the invention provides an isolated microorganism comprising xylose specific reductase activity, wherein the xylose specific reductase activity does not convert L-arabinose to L-arabitol. A microorganism or process of the invention can produce an end-product of xylitol from a substrate comprising D-xylose; or L-arabinose; or L-arabinose and D-xylose; or L-arabinose, D-xylose and other sugars. No substantial amount of L-arabitol is produced as an end-product. No substantial amount of L-arabitol is less than 10, 5, 2, or 1% L-arabitol. The substrate can be a xylan hydrolysate or hemicellulose hydrolysate. In one embodiment the substrate is an agricultural residue such as bagasse agricultural residue, corn cob agriculture residue, flax straw agricultural residue, wheat straw residue, oat hull agricultural residue, tree hydrolysate, or a combination thereof.

A microorganism can be a bacterium, such as *E. coli*, fungus or yeast. In one embodiment, the microorganism is non-pathogenic.

A xylose-specific reductase can be encoded by a nucleic acid comprising a *P. stipitis* xylose reductase (GenBank Acc. No. X59465) or a xylose reductase from another organism comprising a Ser233Pro mutation and a Phe286Leu mutation (SEQ ID NO:43) (FIG. 28).

The invention provides methods for producing xylitol comprising fermenting a substrate comprising D-xylose; or L-arabinose; or L-arabinose and D-xylose; or L-arabinose, D-xylose and other sugars with an isolated microorganism comprising xylose-specific reductase activity, wherein the xylose-specific reductase activity does not convert L-arabinose to L-arabitol. In one embodiment, the method does not require separation of L-arabitol from xylitol.

Xylitol Resistant Xylose Isomerases

To increase the tolerance of xylose isomerase to high levels of xylitol, an *E. coli* xylose isomerase (xylA) was mutagenisized. See, e.g., GenBank Accession Number K01996 and X04691. A microorganism with a xylose isomerase with 1, 2, 3, 4, 5, 6, 7, 8 or more of the following mutations has increased tolerance to xylitol: F9L, Q11K, S20L, L213Q, F283Y, K311R, H420N, H439Q. In particular, the following mutations can increase tolerance to xylitol:

(e) F9L, L213Q, F283Y, K311R, H420N;
(f) F9L, Q11K, L213Q, F283Y, K311R, H420N;
(g) F9L, Q11K, S20L, L213Q, F283Y, K311R, H420N; or
(h) F9L, Q11K, S20L, L213Q, F283Y, K311R, H420N, H439Q.

A microorganism with the mutated xylose isomerase can tolerate about 1%, 2%, 5%, 8%, 10%, 15% or more xylitol. Preferably, the xylose isomerase is purified. A purified protein is purified free of other components, such as other proteins, lipids, culture medium and polynucleotides. For example, the protein can be 50%, 75%, 90%, 95%, 96%, 97%, 98%, 99%, or 100% purified. Proteins of the invention can comprise other peptide sequences, such as labels, linkers, signal sequences, TMR stop transfer sequences, transmembrane domains, or ligands useful in protein purification such as glutathione-S-transferase, histidine tag, and staphylococcal protein A.

One embodiment of the invention provides a nucleic acid molecule encoding the mutant *E. coli* xylose isomerase described above. An isolated nucleic acid is a molecule that is not immediately contiguous with one or both of the 5' and 3' flanking genomic sequences that it is naturally associated with. An isolated polynucleotide can be, for example, a recombinant DNA or RNA molecule of any length, provided that the nucleic acid sequences naturally found immediately flanking the recombinant DNA or RNA molecule in a naturally-occurring genome is removed or absent. Isolated nucleic acid molecules can be naturally-occurring or non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide.

Another embodiment of the invention provides a recombinant microorganism comprising a mutated *E. coli* xylose isomerase coding sequence, wherein the microorganism can grow in the presence of about 1% or more of xylitol.

Other Approaches to the Production of Xylitol

Another approach to the production of xylitol is to convert any L-arabitol formed into a readily metabolized substrate. This could be achieved by adding an L-arabinose to L-xylulose pathway to the host strain (FIG. 5) thus effectively removing any L-arabitol formed.

Another approach would be to use a biosynthetic pathway that does not use a xylose reductase but an alternative enzyme system that does not form L-arabitol from L-arabinose. Such a route is outlined in FIG. 6, it utilizes a xylose isomerase coupled with xylitol dehydrogenase, and this route will form xylitol via a D-xylulose intermediate.

Screening Strains and Methods

The invention also provides screening methods that can be combined with directed evolution to select D-xylose-specific reductases. The screening method is outlined in FIG. 4 and takes advantage of the observation that phosphorylated sugars are toxic to, for example, *E. coli* if allowed to accumulate. See, Scangos & Reiner (1979). "A unique pattern of toxic synthesis in pentitol catabolism: implications for evolution." J Mol Evol 12(3):189-95; Scangos & Reiner (1978). "Acquisition of ability to utilize Xylitol: disadvantages of a constitutive catabolic pathway in *Escherichia coli*." J Bacteriol 134(2):501-5. To take advantage of such a screen a kinase is required that can phosphorylate L-arabitol but not xylitol; the L-ribulokinase of *E. coli* is such an enzyme. See, Lee et al. (2001). "Substrate specificity and kinetic mechanism of *Escherichia coli* ribulokinase." Arch Biochem Biophys, 396 (2):219-24.

The host strain can be auxotrophic for D-xylose and L-arabinose utilization and be able to grow on xylitol (carry an xdh gene). An xdh/araB operon plasmid can be constructed in which the genes are constitutively expressed in a strain that is an araBAD/xylA double mutant. Such a strain, carrying a xylose reductase and grown on a mixture of L-arabinose and D-xylose can grow by forming xylitol from D-xylose. However, the XR will also form L-arabitol that in turn will be converted to L-arabitol 5-phosphate which is lethal when accumulated inside the cell. This is a powerful screen for mutant xylitol reductases that cannot synthesize L-arabitol while simultaneously synthesizing xylitol.

Xylose Reductase Screening Strain. Screening strains for detection and enhancement of the individual enzymes are an important part of the invention. An outline for a xylose reductase screening strain is shown in FIG. 2. In one embodiment of the invention, an *E. coli* strain, such as K12, has a xylose isomerase deletion (xylAΔ) making it unable to grow on D-xylose. *E. coli* cannot synthesize or utilize xylitol as a carbon source and addition of a deregulated xylitol dehydrogenase gene into this host strain enables growth on xylitol because the XDH will convert xylitol to D-xylulose, which can then be utilized via intermediary metabolism. When the screening strain is transformed with a plasmid carrying a putative xylose reductase gene it can be used to screen for XR reductase activity. That is, active clones when grown on a D-xylose minimal medium will only grow if the D-xylose is converted to xylitol. These screening strains are very useful for cloning novel aldose reductases, preliminary screening of mutagenesis libraries, and can also be adapted into a high throughput plate screen for evolved reductases.

L-Arabitol 4-Dehydrogenase Screening Strain. *E. coli* K12 cannot efficiently utilize L-arabitol or L-xylulose as sole carbon and energy sources See, Badia et al. (1991). "L-lyxose metabolism employs the L-rhamnose pathway in mutant cells of *Escherichia coli* adapted to grow on L-lyxose." J Bacteriol 173(16):5144-50. It cannot utilize L-arabitol because it does not possess the required degradation pathway that is found in other enteric organisms. See, Reiner (1975). "Genes for ribitol and D-arabitol catabolism in *Escherichia coli*: their loci in C strains and absence in K-12 and B strains." J Bacteriol, 123(2):530. Conversely, while *E. coli* K12 carries all the genes required for L-xylulose utilization it does not use this substrate because the degradation genes are found in two separate cryptic operons. See, Ibanez et al. (2000). "Role of the yiaR and yiaS genes of *Escherichia coli* in metabolism of endogenously formed L-xylulose." J Bacteriol 182(16): 4625-7; Yew & Gerlt (2002). "Utilization of L-ascorbate by *Escherichia coli* K-12: assignments of functions to products of the yjf-sga and yia-sgb operons." J Bacteriol 184(1):302-6. FIG. 3 shows the logic behind this screen. A screening strain requires the deregulation of three genes lyxK (L-xylulose kinase), ulaE (L-xylulose 5-phosphate epimerase) and ulaF (L-ribulose 5-phosphate 4-epimerase). In one embodiment of the invention all the genes are cloned into a plasmid under control of a constitutive promoter. In another embodiment of the invention the yiaJ gene (repressor protein of the yia-sgb operon of *E. coli*) is deleted. Once deregulated, growth on L-xylulose is possible but not growth on L-arbinitol. This strain can then be used to screen for L-arbinitol 4-dehydrogenase activity because it confers the ability of growth on L-arbinitol on the screening strain. Such a strain would also be useful for preliminary screening of L-arbinitol 4-dehydrogenase mutagenesis libraries so null mutations could be easily eliminated.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Co-pending patent application U.S. Ser. No. 11/133,025, filed May 19, 2005, entitled "Microbial production of xylitol via a hexose phosphate and a pentose phosphate intermediate" is incorporated herein by reference in its entirety.

EXAMPLES

Example 1

Cloning and Preliminary Analysis of the *Pichia stipitis* Xylose Reductase Gene Expressed in *E. coli*

A *Pichia stipitis* XR was cloned using primers designed from the published sequence (GenBank Acc. # X59465) by reverse transcriptase-PCR (RT-PCR). *P. stipitis* was grown overnight on YM media containing 1% D-xylose (w/v). Total RNA was isolated using the NucleoSpin RNA II kit (Promega). The gene was amplified using specific primers (SEQ ID NO:1 and SEQ ID NO:2, Table 2) and the Access RT-PCR system (BD Biosciences, USA) with an Eppendorf Mastercycler PCR machine, using standard amplification parameters. The RT-PCR reaction yielded a single band by gel electrophoresis. The gene was restricted with KpnI and BamHI using standard conditions then ligated using a rapid DNA ligation kit (Takara v.2, Takara Miros Bio, USA) into the cloning and expression plasmid pTTQ18, restricted with the same enzymes to yield pZUC5 (FIG. 7). DNA sequencing (AGCT, Northbrook, Ill.) showed complete identity to the published sequence.

The *P. stipitis* XR expressed in *E. coli* was analyzed using a spectrophotometric assay. The assay monitors the conversion of D-xylose to xylitol by measuring the loss of a nicotinimide cofactor (NADH) at $A_{340}$. The host strain for this analysis was ZUC25/pZUC5, an *E. coli* W3110 xylAΔ strain (ZUC25) transformed with pZUC5. A single colony of ZUC25/pZUC5 was inoculated into 2 mL LB broth supplemented with ampicillin (200 mg/L). A control culture ZUC25/pTFQ18 (pZUC25 transformed with pTTQ18) was grown treated in the same way. The cultures were incubated overnight at 30° C. with shaking (200 RPM). A 1 mL aliquot of each culture was then diluted into 100 mL fresh LB media with ampicillin (200 mg/L) and incubation was continued (30° C., 200 RPM) until the $A_{660}$ was 0.1. Each culture was induced with 1 mM IPTG and culture was further incubated for an additional 3 hrs. Cells were harvested by centrifugation (2000×g's, 20 mins), and the media was decanted. The cells were stored at −20° C. until needed for prior to cell lysis.

The cells were lysed with 1 mL BugBuster protein extraction reagent (Novagen, USA) at 37° C. The bacterial cell debris was removed with centrifugation (12,000×g's, 10 mins). The cell lysate was then kept cold (4° C.) during the brief period before the activity assay was performed. For the assay, D-xylose (100 mM, Sigma, USA) and NADH (15 mg/mL, Calbiochem, USA) stock solutions were prepared in 100 mM PIPES buffer (Sigma). To perform the assay, 100 µL cell lysate was mixed with 1 mL D-xylose and 10 µL NADH stock solutions. Activity was measured by following the decrease in absorbance at 340 nm due to the reduction of NADH, readings were taken every minute for 10 mins. The lysate containing the induced *P. stipitis* XR showed a 9.6-fold increase in the NADH loss as compared to the negative control. This increase in rates is evidence for a functionally expressed *P. stipitis* XR enzyme in an *E. coli* host.

ZUC25/pZUC5 and the control strain ZUC25/pTTQ18 were also tested for their ability to convert D-xylose to xylitol by in vivo bioconversion. Each strain was inoculated from a single colony into 2 mL M9 minimal media supplemented with glycerol (0.2% v/v) and ampicillin (200 mg/L) and incubated overnight at 30° C. with shaking (200 RPM). After incubation, an aliquot of each was diluted 100-fold into 10 mL of fresh M9 minimal media contain glycerol (0.2% v/v) and ampicillin (200 mg/L) and continued incubation (30° C., 200 RPM) until the $A_{660}$ reached 0.1. The cultures were induced with isopropyl-β-D-thiogalactopyranoside (IPTG, 1 mM and D-xylose (1% w/v) and ampicillin (200 mg/L) were added. The cultures were incubated at 30° C. with shaking (200 RPM) and aliquots were removed at various time points after the IPTG induction. The samples were then analyzed by HPLC analysis using an Aminex HPX-87P column (BioRad, USA). After 24 hrs of induction, the *P. stipitis* XR displayed 10% conversion of D-xylose to xylitol thus proving that the enzyme was functionally expressed. As expected the control strain did not accumulate any xylitol. This confirmed the enzymatic data and proves that the *P. stipitis* XR is functionally expressed in *E. coli*.

Example 2

Cloning of the yafB Aldose Reductase from *E. coli* K12

The *Escherichia coli* aldose reductase (putative XR) gene was cloned using the annotated sequence of yafB (GenBank, Acc. # AE000129). The gene was cloned directly from the genomic DNA of *E. coli* K12 strain ER1793. The genomic DNA was isolated using a modified procedure of the Qiagen miniprep (Qiagen Inc., USA) kit using a 2 mL culture of ER1793 grown overnight in Lauria-Bertani (Miller) media (LB). The procedure differs from the standard procedure in the addition of a 5 min vortexing step of the DNA sample after addition of buffer 2. The modified procedure gave a large distribution of DNA fragment sizes as seen by agarose gel electrophoresis. The gene was amplified by PCR using specific primers (SEQ ID NO:3 and SEQ ID NO:4, Table 2) in an Eppendorf Mastercyler PCR machine from genomic DNA using a FailSafe PCR cloning kit (Epicentre, USA). This reaction yielded a single band when visualized by agarose gel electrophoresis. The amplified DNA fragment was restricted with EcoRI and BamHI using standard conditions then ligated using a rapid ligation kit (Takara v.2, Takara Miros Bio, USA) into the cloning and expression plasmid pTTQ18, restricted with the same enzymes to yield pZUC19 (FIG. 8). DNA sequencing (AGCT, Northbrook, Ill.) of the isolated clone showed complete identity to the published sequence.

Example 3

Cloning and Preliminary Analysis of the *Candida tenuis* Xylose Reductase Gene

The *Candida tenuis* XR was cloned using primers designed from the published sequence (GenBank Acc. # AF074484) by RT-PCR. *C. tenuis* was grown overnight on YM media containing 1% D-xylose (w/v). The total RNA was isolated using the NucleoSpin RNA II kit (Promega, USA). The gene was amplified using specific primers (SEQ ID NO:5 and SEQ ID NO:6, Table 2) and the Access RT-PCR system (BD Biosciences, USA) with an Eppendorf Mastercycler PCR machine using standard amplification parameters. The RT-PCR reaction yielded a single band by gel electrophoresis. The amplified fragment was restricted with EcoRI and BamHI using standard conditions then ligated using a rapid ligation kit (Takara v.2, Takara Miros Bio, USA) into the cloning and expression plasmid pTTQ18, restricted with the same enzymes to yield pZUC30 (FIG. 9). DNA sequencing (AGCT, Northbrook, Ill.) showed complete identity to the published sequence.

To test the enzymatic activity of the cloned C. tenuis XR in vivo, ZUC25 (E. coli W3110 xylAΔ) was transformed with pZUC30 by electroporation. The resultant strain, ZUC25/pZUC30 and control strain ZUC25/pTTQ18 (ZUC25 transformed pTTQ18) were tested for their ability to convert D-xylose to xylitol by in vivo bioconversion. Each strain was inoculated from a single colony into 2 mL M9 minimal media supplemented with glycerol (0.2% v/v) and ampicillin (200 mg/L) and incubated overnight at 30° C. with shaking (200 RPM). After incubation, an aliquot of each was diluted 100-fold into 10 mL of fresh M9 minimal media contain glycerol (0.2% v/v) and ampicillin (200 mg/L) and continued incubation (30° C., 200 RPM) until the $A_{660}$ reached 0.1. The cultures were induced with isopropyl-β-D-thiogalactopyranoside (IPTG, 1 mM and D-xylose (1% w/v) and ampicillin (200 mg/L) were added. The cultures were incubated at 30° C. with shaking (200 RPM) and aliquots were removed at various time points after the IPTG induction. The samples were then analyzed by HPLC analysis using an Aminex HPX-87P column (BioRad, USA). After 24 hrs post induction, the C. tenuis XR strain (ZUC25/pZUC30) displayed 15% conversion of D-xylose to xylitol thus proving that the enzyme was functionally expressed in E. coli. The control strain ZUC25/pTTQ18 did not accumulate any xylitol.

Example 4

Cloning and Preliminary Analysis of the
Trichoderma reesei L-Arabitol 4-Dehydrogenase
Gene (lad1)

The T. reesei L-arbinitol-4-dehydrogenase gene was cloned using primers designed from the published sequence (GenBank Acc. # AF355628) by RT-PCR. T. reesei was grown overnight on YM media containing 1% L-arabinose (w/v). Total RNA was isolated using the NucleoSpin RNA II kit (Promega, USA)). The gene was amplified using specific primers (SEQ ID NO:7 and SEQ ID NO:8, Table 2) and the Access RT-PCR system (BD Biosciences, USA) with an Eppendorf Mastercycler PCR machine, using standard amplification parameters. The RT-PCR reaction yielded a single band by gel electrophoresis. The gene was restricted with EcoRI and BamHI using standard conditions then ligated using a rapid DNA ligation kit (Takara v.2, Takara Miros Bio, USA) into the cloning and expression plasmid pTTQ18, restricted with the same enzymes to yield pZUC6 (FIG. 10). DNA sequencing (AGCT, Northbrook, Ill.) showed complete identity to the published sequence.

To test the activity of the cloned T. reesei LAD1 gene, plasmid pZUC6 was inserted into strain ZUC29 (E. coli E. coli BW255113/xlyΔ, Δ[araD-araB]567, xylAΔ, lacZ4787 (Δ)(::rrnB-3), lacIp-4000[lacIQ, rph-1, Δ(rhaD-rhaB)568) (pZUC29/pZUC6). The host strain, ZUC29 can not utilize L-arabitol and can therefore be used to screen for synthesis of L-xylulose from L-arabitol. A control strain, ZUC29 transformed with pTTQ18 was also made for comparison. Each strain was inoculated from a single colony into 2 mL M9 minimal media supplemented with glycerol (0.2% v/v) and ampicillin (200 mg/L) and incubated overnight at 30° C. with shaking (200 RPM). After incubation, an aliquot of each was diluted 100-fold into 10 mL of fresh M9 minimal media contain glycerol (0.2% v/v) and ampicillin (200 mg/L) and continued incubation (30° C., 200 RPM) until the $A_{660}$ reached 0.1. The cultures were induced with isopropyl-β-D-thiogalactopyranoside (IPTG, 1 mM and L-arabinose (1% w/v) and ampicillin (200 mg/L) were added. The cultures were incubated at 30° C. with shaking (200 RPM) and aliquots were removed at various time points after the IPTG induction. The samples were monitored for L-xylulose formation from L-arabitol, the reverse of the in vivo reaction by HPLC analysis using a Aminex HPX-87P column (BioRad, USA). After 24 hrs post induction, the T. reesei LAD1 strain (ZUC29/pZUC6) displayed a 2.7% conversion of L-arabitol to L-xylulose thus showing that the enzyme was functionally expressed in E. coli. As expected the control strain ZUC29/pTTQ18 did not accumulate any L-xylulose.

Example 5

Cloning and Preliminary Analysis of the
Trichoderma reesei L-xylulose Reductase Gene
(lxr1)

The T. reesei L-xylulose reductase gene was cloned using primers designed from the published sequence (GenBank Acc # AF375616) by RT-PCR. T. reesei was grown overnight on YM media containing 1% L-arabinose (w/v). The total RNA was isolated using the NucleoSpin RNA II kit (Promega, USA)). The gene was amplified using specific primers (SEQ ID NO:9 and SEQ ID NO:10, Table 2) and the Access RT-PCR system (BD Biosciences, USA) with an Eppendorf Mastercycler PCR machine, using standard amplification parameters. The RT-PCR reaction yielded a single band by gel electrophoresis. The gene was restricted with EcoRI and BamHI using standard conditions then ligated using a rapid DNA ligation kit (Takara v.2, Takara Miros Bio, USA) into the cloning and expression plasmid pTTQ18, restricted with the same enzymes to yield pZUC7 (FIG. 11). DNA sequencing (AGCT, Northbrook, Ill.) showed complete identity to the published sequence.

To test the activity of the cloned T. reesei LXR gene, plasmid pZUC7 was inserted into strain ZUC29 by electroporation. A control strain was constructed by electroporating ZUC29 with pTTQ18 expression vector. Each strain was inoculated from a single colony into 2 mL M9 minimal media supplemented with glycerol (0.2% v/v) and ampicillin (200 mg/L) and incubated overnight at 30° C. with shaking (200 RPM). After incubation, an aliquot of each was diluted 100-fold into 10 mL of fresh M9 minimal media contain glycerol (0.2% v/v) and ampicillin (200 mg/L) and continued incubation (30° C., 200 RPM) until the $A_{660}$ reached 0.1. The cultures were induced with isopropyl-β-D-thiogalactopyranoside (IPTG, 1 mM and xylitol (0.1% w/v) and ampicillin (200 mg/L) were added. The cultures were incubated at 30° C. with shaking (200 RPM) and aliquots were removed at various time points after the IPTG induction. The samples were monitored for L-xylulose formation from xylitol (the reverse of the in vivo reaction) by HPLC analysis using a Aminex HPX-87P column (BioRad, USA). After 46 hrs post induction, the T. reesei LAD1 strain (ZUC29/pZUC7) there was an 11% conversion of xylitol to L-xylulose thus showing that the enzyme was functionally expressed in *E. coli*. As expected the control strain ZUC29/pTTQ18 did not accumulate any L-xylulose.

Example 6

Cloning of the *Trichoderma reesei* Xylitol Dehydrogenase Gene

The *T. reesei* xylitol dehydrogenase gene was cloned using primers designed from the published sequence (GenBank Acc.# AF428150) by RT-PCR. *T. reesei* was grown overnight on YM media containing 1% D-xylose (w/v). Total RNA was isolated using the NucleoSpin RNA II kit (Promega, USA)). The gene was amplified using specific primers (SEQ ID NO:11 and SEQ ID NO:12) and the Access RT-PCR system (BD Biosciences, USA) with an Eppendorf Mastercycler PCR machine, using standard amplification parameters. The RT-PCR reaction yielded a single band by gel electrophoresis. The gene was restricted with EcoRI and BamHI using standard conditions then ligated using a rapid DNA ligation kit (Takara v.2, Takara Miros Bio, USA) into the cloning and expression plasmid pTTQ18, restricted with the same enzymes to yield pZUC31 (FIG. 12). DNA sequencing (AGCT, Northbrook, Ill.) showed complete identity to the published sequence.

Example 7

Construction of an L-Arabitol 4-Dehydrogenase/L-Xylulose Reductase Operon

The lad1/lxr1 operon was constructed in the following way: The lxr1 gene was replicated by PCR using a 5' forward primer (SEQ ID NO:15) and a 3' reverse primer (SEQ ID NO:16, Table 2) using an Advantage 2 PCR kit (BD Biosciences, USA) in an Eppendorf Mastercycler PCR machine, using standard conditions. The 5' forward primer has an XbaI restriction site and a consensus ribosome binding site (RBS) upstream of the lxr1 ATG start codon. The 3' reverse primer has a HindIII restriction site. The replicated fragment was restricted with XbaI and HindIII, and ligated into pZUC6 cut with the same restriction enzymes. The resultant plasmid was named pZUC18 (FIG. 13).

The throughput of this operon could be improved by mutagenesis and screening of this operon in an *E. coli* strain expressing a xdh gene. When plated with L-arbinitol as a sole carbon source only clones able to convert L-arbinitol to xylitol will grow. Further enhancements could be detected using a high throughput crossfeeding strain in an analogous way using plates containing L-arabitol. For fine tuning the genes involved in L-xylulose metabolism such as but not limited to lyxK, ulaE and ulaF could be removed.

Example 8

Construction of a Xylose Reductase/L-Arabitol 4-Dehydrogenase Operons (XR/LAD1 and yafB/LAD1)

Two XR/LAD1 operons were constructed using the *E. coli* yafB and the *P. stipitis* XYL1 xylose reductases in combination with the lad1 gene from *T. reesei*. The lad1 gene was replicated by PCR using a 5' forward primer (SEQ ID NO: 17) and a 3' reverse primer (SEQ ID NO: 18, Table 2) using an Advantage 2 PCR kit (BD Biosciences, USA) in an Eppendorf Mastercycler PCR machine, using standard conditions. The 5' forward primer contained an BamHI restriction site and a consensus RBS upstream of the lad1 ATG start codon. The 3' reverse primer carried a XbaI restriction site. The replicated fragment was restricted with BamHI and XbaI, and ligated into pZUC5 and pZUC19 cut with the same restriction enzymes. The resultant plasmids named pZUC20 (*P. stipitis* XR/LAD1) and pZUC21 (*E. coli* yafB/LAD1) can be seen in FIGS. 14 and 15.

Example 9

Construction of the Xylose Reductase./L-Arabitol 4-Dehydrogenase/L-Xylulose Reductase Operons The construction of the *P. stipitis* XR/LAD1/LXR1 and operon was achieved by replacing the 200 bp HindIII-PstI fragment of pZUC20 with the 1004 bp HindIII-PstI fragment of pZUC18, to create plasmid pZUC24 (FIG. 16). The yafB/LAD1/LXR1 was similarly constructed by replacing the 200 bp HindIII-PstI fragment of pZUC21 with the 1004 bp HindIII-PstI fragment of pZUC18, to create plasmid pZUC25 (FIG. 17).

Example 10

Cloning of the *Gluconobacter oxydans* D-Xylose Dehydrogenase Gene and its Use in D-Xylose Reductase Screening Strains The xylitol dehydrogenase gene was cloned directly from the genomic DNA of *Gluconobacter oxydans* strain NRRL B-72 using the published sequence (Sugiyama et al., 2003. Biosci Biotechnol Biochem 67:584) by PCR. Primers SEQ ID NO:19 and SEQ ID NO:20 (Table 2) were used to amplify the gene sequence. The amplified fragment was cleaved with restriction enzymes EcoRI and BamHI followed by ligation into expression vector pTrp338 cut with the same enzymes, to form plasmid pZUC15 (FIG. 18).

Deletion of the xlyA gene from *E. coli* K12 was carried out using the published RED deletion protocol. Datsenko & Wanner. 2000. Proc. Natl. Acad. Sci. USA 97, 6640-6645. The primers for the deletion were SEQ ID NO:21 and SEQ ID NO:22 (Table 2). This protocol only works well in strains that cannot metabolize L-arabinose so the deletion was initially made in BW25113 (supplied with the RED deletion kit) and then transferred to *E. coli* AB707 and W3110 by P1 transduction by selection for the inserted chloramphenicol acetyltransferase gene (cat) (Short course in Bacterial Genetics: A Laboratory Manual and Handbook for *Escherichia coli* and Related Bacteria, Jeffrey H. Miller, Cold Spring Harbor Laboratory; $1^{st}$ Ed., (Jan. 15, 1992). The antibiotic gene was then removed by FLP-mediated excision following the published protocol. The resultant $Cm^s$ xylAΔ strains were named ZUC24 (AB707; xylAΔΔ) and ZUC25 (W3110; xylAΔΔ, λIN[rrnD-rrnE]1, rph-1). The BW25113/xylAΔ strain was similarly cured of the cat gene and the resultant strain was named ZUC29.

ZUC24 and ZUC25 were transformed with plasmid pZUC15 by electroporation and the resultant strains were named ZUC26 and ZUC27 respectively. The phenotypic characteristics of these strains are shown in Table 3. Strains ZUC26 and ZUC27 can be used as a selection hosts for XR activity (cloned on a compatible plasmid) because strains carrying active XR's will be able to synthesize xylitol, which in turn will be converted to D-xylulose by the XDH and thus allow growth on D-xylose as sole carbon source. The utility of strain ZUC26 as a XR screening strain is shown in Table 4.

The results show that while pZUC19 conferred growth on D-xylose at both 30° C. and 37° C., pZUC5 was only active at 30° C. These results confirm the synthesis of xylitol from both of these reductases.

An alternative screening strain, ZUC49 was also constructed by transformation of ZUC25 with the *T. reesei* xdh clone pZUC31 (FIG. 13). The phenotype and genotype of this strain are shown Table 3. ZUC49 was transformed with pZUC30 (*C. tenuis* XR) and tested for growth on D-xylose, the results (Table 4) showed that growth occurred at 30° C. but not at 37° C.

Example 11

L-Arabitol 4-Dehydrogenase Screening Strain

The genes for the deregulated L-xylulose pathway were obtained from *E. coli* using PCR. It was constructed in two stages (FIG. 19), firstly the L-xylulose kinase (lyxK) was isolated using PCR using primers SEQ ID NO:23 and SEQ ID NO:24. The fragment was cleaved with EcoRI and BamHI and ligated into pTrp338 cut with the same enzymes to form pZUC4. The two remaining genes ulaE and ulaF were replicated as a natural operon using primer SEQ ID NO:25 and SEQ ID NO:26. The fragment was cleaved with BglII and NcoI then ligated into pZUC4 cleaved with BamHI and NcoI to form pZUC8. When transformed with pZUC6 (LAD1 clone) this plasmid conferred growth on L-arabitol whereas the host carrying pTTQ18 does not.

Example 12

Cloning and Analysis of the *Ambrosiozyma monospora* L-Xylulose Reductase Gene (Alx1)

The *A. monospora* L-xylulose reductase gene was cloned using primers designed from the published sequence (GenBank Acc.# AJ583159) by RT-PCR. *A. monospora* was grown overnight on YM media containing 2% L-arabinose (w/v). Total RNA was isolated using the RNeasy kit (Qiagen, USA). The gene was amplified using specific primers (SEQ ID NO:27 and SEQ ID NO:28) and the One-Step RT-PCR kit (Qiagen, USA) with a DNA Engine Peltier Thermal Cycler PCR machine (MJ Research, USA), using standard amplification parameters. The RT-PCR reaction yielded a single band by gel electrophoresis. The gene was restricted with EcoRI and BamHI using standard conditions then ligated using the Quick Ligation kit (New England Biolabs, USA) into the cloning and expression plasmid pTTQ18, restricted with the same enzymes to yield pATX101 (FIG. 20). DNA sequencing using the BigDyeTerminator v3.1 Cycle Sequencing kit (Applied Biosystems, USA) and the ABI PRISM 3100 Genetic Analyzer (Applied Biosystems) showed complete identity to the published sequence.

To test the activity of the cloned *A. monospora* alx1 gene, plasmid pATX101 was inserted into strain ZUC99 (lyxKΔ, Δ(araD-araB)567, lacZ4787(Δ)(::rrnB-3), lacIp-4000(lacIQ),λ-, rph-1, Δ(rhaD-rhaB)568, hsdR514) by electroporation (ZUC99/pATX101). A control strain, ZUC99 transformed with pTTQ18 was also made for comparison. Each strain was inoculated from a single colony into 3 mL LB media supplemented with ampicillin (200 mg/L) and incubated overnight at 30° C. with shaking (250 RPM). After incubation, an aliquot of each was diluted 100-fold into 20 mL of fresh LB media contain xylitol (1% w/v) and ampicillin (200 mg/L) and incubated (30° C., 250 RPM) for 2 hrs. The cultures were induced with isopropyl-β-D-thiogalactopyranoside (IPTG, 1 mM). The cultures were incubated at 30° C. with shaking (250 RPM) and aliquots were removed at various time points after the IPTG induction. The samples were monitored for L-xylulose formation from xylitol, the reverse of the in vivo reaction by HPLC analysis using an Aminex HPX-87P column (BioRad, USA). After 24 hrs post induction, the Alx1 strain (ZUC99/pATX101) displayed a 12% conversion of xylitol to L-xylulose thus showing that the enzyme was functionally expressed in *E. coli*. As expected the control strain ZUC99/pTTQ18 did not accumulate any L-xylulose.

Example 13

Construction and Analysis of an L-Arabitol 4-Dehydrogenase/L-Xylulose Reductase Operon (Lad1/Alx1)

The Lad1/Alx1 operon was constructed in the following way: The alx1 gene cloned in plasmid pATX101 was replicated by PCR using a 5' forward primer (SEQ ID NO:29) and a 3' reverse primer (SEQ ID NO:30) using a Taq DNA polymerase (Qiagen, USA) in a DNA Engine Peltier Thermal Cycler PCR machine (MJ Research, USA), using standard conditions. The 5' forward primer has a BamHI restriction site and a consensus ribosome binding site (RBS) upstream of the Alx1 ATG start codon. The 3' reverse primer has an XbaI restriction site. The replicated fragment was restricted with BamHI and XbaI, and ligated into pZUC6 cut with the same restriction enzymes. The resultant plasmid was named pATX106 (FIG. 21).

To test the activity of the Lad1/Alx1 operon, plasmid pATX106 was inserted into strain ZUC99 by electroporation (ZUC99/pATX106). The strain was inoculated from a single colony into 3 mL LB media supplemented with ampicillin (200 mg/L) and incubated overnight at 30° C. with shaking (250 RPM). After incubation, an aliquot of the culture was diluted 100-fold into 20 mL of fresh LB media contain L-arabitol (1% w/v) and ampicillin (200 mg/L) and incubated (30° C., 250 RPM) for 2 hrs. To induce the operon, isopropyl-β-D-thiogalactopyranoside (IPTG, 1 mM) was added. The culture which was not induced with IPTG was used as a negative control. The cultures were incubated at 30° C. with shaking (250 RPM) and aliquots were removed at various time points after the IPTG induction. The samples were monitored for xylitol formation from L-arabitol by HPLC analysis using an Aminex HPX-87P column (BioRad, USA). After 25 hrs post induction, the Lad1/Alx1 operon strain (ZUC99/pATX106) displayed a 6% conversion of L-arabitol to xylitol thus showing that the operon was functionally expressed in *E. coli* (Table 5). As expected the control culture did not accumulate any L-xylulose and xylitol (Table 5).

Example 14

Construction and Analysis of a Xylose Reductase/L-Arabitol 4-Dehydrogenase/L-Xylulose Reductase Operon (XR/Lad1/Alx1)

An XR/Lad1/Alx1 operon was constructed using the *P. stipitis* xylose reductase gene, the *T. reesei* L-arabitol 4-dehydrogenase gene and the *A. monospora* L-xylulose reductase gene. The XR gene cloned in plasmid pZUC20 was replicated by PCR using a 5' forward primer (SEQ ID NO:31) and a 3' reverse primer (SEQ ID NO:32) using a Taq DNA polymerase (Qiagen, USA) in a DNA Engine Peltier Thermal Cycler PCR machine (MJ Research, USA), using standard conditions.

The 5' forward primer has a nucleotide sequence annealing to an upstream region of the tac promoter in a pTTQ18 plasmid. Both of the 5' forward and 3' reverse primers have a BamHI restriction site. The replicated fragment was restricted with BamHI, and ligated into pATX106 cut with the same restriction enzyme and dephosphorylated with the Antarctic phosphatase (New England Biolabs, USA). The resultant plasmid was named pATX112 (FIG. 22).

To test the activity of the XR/Lad1/Alx1 operon, plasmid pATX112 was inserted into strain ZUC99 by electroporation (ZUC99/pATX112). The strain was inoculated from a single colony into 3 mL LB media supplemented with ampicillin (200 mg/L) and incubated overnight at 30° C. with shaking (250 RPM). After incubation, an aliquot of the culture was diluted 100-fold into 20 mL of fresh LB media contain L-arabinose (1% w/v) and ampicillin (200 mg/L) and incubated (30° C., 250 RPM) for 2 hrs. The culture was induced with isopropyl-β-D-thiogalactopyranoside (IPTG, 1 mM). The culture was incubated at 30° C. with shaking (250 RPM) and aliquots were removed at various time points after the IPTG induction. The samples were monitored for xylitol formation from L-arabinose by HPLC analysis using an Aminex HPX-87P column (BioRad, USA). After 24 hrs post induction, the XR/Lad1/Alx1operon strain (ZUC99/pATX112) displayed a 2% conversion of L-arabinose to xylitol, showing that the recombinant bacterium acquires the ability to produce xylitol from L-arabinose (Table 6).

Example 15

Cloning and Analysis of the *Klebsiella pneumoniae* Ribitol Dehydrogenase Gene (RbtD)

The *K. pnuemoniae* ribitol dehydrogenase gene was cloned using primers designed from the published sequence of the *K. aerogenes* ribitol dehydrogenase gene (GenBank Acc.# M25606) by PCR. A genomic DNA of *K. pneumoniae* was obtained from the ATCC culture collection. The gene was amplified using specific primers (SEQ ID NO:33 and SEQ ID NO:34) and a Taq DNA polymerase (Qiagen, USA) in a DNA Engine Peltier Thermal Cycler PCR machine (MJ Research, USA), using standard amplification parameters. The PCR reaction yielded a single band by gel electrophoresis. The gene was restricted with EcoRI and BamHI using standard conditions then ligated using the Quick Ligation kit (New England Biolabs, USA) into the cloning and expression plasmid pTTQ18, restricted with the same enzymes to yield pATX114 (FIG. 23). DNA sequence of the *K. pnuemoniae* ribitol dehydrogenase gene was analyzed using the BigDyeTerminator v3.1 Cycle Sequencing kit (Applied Biosystems, USA) and the ABI PRISM 3100 Genetic Analyzer (Applied Biosystems). The deduced amino acid sequences between the ribitol dehydrogenase genes from *K. aergogenes* (GenBank Acc.# M25606) and *K. pnuemoniae* are identical, although DNA sequences differ by 4 nucleotides.

The *K. pneumoniae* RbtD expressed in *E. coli* was analyzed using a spectrophotometric assay. The assay monitors the oxidation of L-arabitol to L-xylulose by measuring the change in absorbance at 340 nm, which occurs as a nicotinamide cofactor NAD is reduced to NADH. Plasmid pATX114 was inserted into strain ZUC99 by electroporation (ZUC99/pATX114). A single colony of the strain was inoculated into 3 mL LB broth supplemented with ampicillin (200 mg/L). A control culture ZUC99/pTTQ18 was grown treated in the same way. The cultures were incubated overnight at 30° C. with shaking (250 RPM). An aliquot of each culture was then diluted 100-fold into 3 mL fresh LB media with ampicillin (200 mg/L) and incubation was continued (37° C., 250 RPM) for 2 hrs. Each culture was induced with 1 mM IPTG and culture was further incubated for an additional 6 hrs. Cells were harvested from 500 µL aliquot of each culture by centrifugation (14,000×g, 10 mins), and the media was decanted. The cells were stored at −20° C. until needed for prior to cell lysis.

The cells were lysed with 50 µL BugBuster protein extraction reagent (Novagen, USA) at room temperature. The bacterial cell debris was removed with centrifugation (14,000×g, 20 mins). The cell lysate was then kept on ice during the brief period before the activity assay was performed. To perform the enzyme reaction, 10 µL cell lysate was mixed with 990 µl reaction mixture (100 mM Tris-Cl (pH9.0), 0.5 mM MgCl$_2$, 2 mM NAD and 100 mM L-arabitol) in a quartz cuvette at 30° C. Activity was measured by following the increase in absorbance at 340 nm, using a spectrophotometer (model 8453, Agilent, USA). Protein amount in the lysate was determined using the DC Protein Assay kit (BioRad, USA), using bovine serum albumin for standard curve construction. One unit was defined as the amount of enzyme that caused the reduction of 1.0 µmol NAD to NADH per min. The lysate containing the induced *K. pneumoniae* RbtD showed 0.65 unit/mg protein. The lysate from the control strain did not show any activity.

ZUC99/pATX114 was also tested for their ability to convert L-arabitol to L-xylulose by in vivo bioconversion. The strain was inoculated from a single colony into 3 mL LB media supplemented with ampicillin (200 mg/L) and incubated overnight at 30° C. with shaking (250 RPM). After incubation, an aliquot of the culture was diluted 100-fold into 3 mL of fresh LB media contain L-arabitol (1% w/v) and ampicillin (200 mg/L) and incubated (37° C., 250 RPM) for 2 hrs. The culture was induced with isopropyl-β-D-thiogalactopyranoside (IPTG, 1 mM). The culture was incubated at 37° C. with shaking (250 RPM) and aliquots were removed at various time points after the IPTG induction. The samples were monitored for L-xylulose formation from L-arabitol by HPLC analysis using an Aminex HPX-87P column (BioRad, USA). After 24 hrs post induction, the RbtD strain (ZUC99/pATX114) displayed a 19% conversion of L-arabitol to L-xylulose (Table 7).

These results clearly show that the ribitol dehydrogenase RbtD is functionally expressed in *E. coli* and can convert L-arabitol to L-xylulose.

Example 16

Construction and Analysis of a Ribitol Dehydrogenase/Ribitol Transporter Operon (RbtD/RbtT)

The RbtD/RbtT operon was constructed in the following way: The *K. pneumoniae* ribitol transporter RbtT gene was isolated by PCR using primers designed from the published sequence (GenBank Acc.# AF045244). A genomic DNA of *K. pneumoniae* was obtained from the ATCC culture collection. The gene was amplified using specific primers (SEQ ID NO:35 and SEQ ID NO:36) and the PfuUltra Hotstart DNA polymerase (Stratagene, USA) in a DNA Engine Peltier Thermal Cycler PCR machine (MJ Research, USA), using standard amplification parameters. The 5' forward primer has a BamHI restriction site and a consensus ribosome binding site (RBS) upstream of the RbtT ATG start codon. The 3' reverse primer has an XbaI restriction site. The replicated fragment was restricted with BamHI and XbaI, and ligated into pATX114 cut with the same restriction enzymes. The resultant plasmid was named pATX115 (FIG. 24).

To test the activity of the RbtD/RbtT operon, plasmid pATX115 was inserted into strain ZUC99 by electroporation (ZUC99/pATX115). The strain was inoculated from a single colony into 3 mL LB media supplemented with ampicillin (200 mg/L) and incubated overnight at 30° C. with shaking (250 RPM). After incubation, an aliquot of the culture was diluted 100-fold into 3 mL of fresh LB media contain L-arabitol (1% w/v) and ampicillin (200 mg/L) and incubated (37° C., 250 RPM) for 2 hrs. The culture was induced with isopropyl-β-D-thiogalactopyranoside (IPTG, 1 mM). The culture was incubated at 37° C. with shaking (250 RPM) and aliquots were removed at various time points after the IPTG induction. The samples were monitored for L-xylulose formation from L-arabitol by HPLC analysis using an Aminex HPX-87P column (BioRad, USA). After 24 hrs post induction, the RbtD/RbtT operon strain (ZUC99/pATX115) displayed a 57% conversion of L-arabitol to L-xylulose showing that the ribitol transporter RbtT improved the in vivo bioconversion of L-arabitol to L-xylulose (Table 7).

Example 17

Construction and Analysis of a Ribitol Dehydrogenase/Ribitol Transporter/L-Xylulose Reductase Operon (RbtD/RbtT/Alx1)

The RbtD/RbtT/Alx1 operon was constructed in the following way: The Alx1 gene in pATX101 was replicated by PCR using a 5' forward primer (SEQ ID NO:37) and a 3' reverse primer (SEQ ID NO:30) using the PfuUltra Hotstart DNA polymerase (Stratagene, USA) in a DNA Engine Peltier Thermal Cycler PCR machine (MJ Research, USA), using standard conditions. The 5' forward primer has a nucleotide sequence annealing to an upstream region of the tac promoter in a pTTQ18 plasmid. Both of the 5' forward and 3' reverse primers have an XbaI restriction site. The replicated fragment was restricted with XbaI, and ligated into pATX115 cut with the same restriction enzyme and dephosphorylated with the Antarctic phosphatase (New England Biolabs, USA). The resultant plasmid was named pATX118 (FIG. 25).

To test the activity of the RbtD/RbtT/Alx1 operon, plasmid pATX118 was inserted into strain ZUC99 by electroporation (ZUC99/pATX118). The strain was inoculated from a single colony into 3 mL LB media supplemented with ampicillin (200 mg/L) and incubated overnight at 30° C. with shaking (250 RPM). After incubation, an aliquot of the culture was diluted 100-fold into 20 mL of fresh LB media contain L-arabitol (1% w/v) and ampicillin (200 mg/L) and incubated (30° C., 250 RPM) for 2 hrs. The culture was induced with isopropyl-β-D-thiogalactopyranoside (IPTG, 1 mM). The culture was incubated at 30° C. with shaking (250 RPM) and aliquots were removed at various time points after the IPTG induction. The samples were monitored for xylitol formation from L-arabitol by HPLC analysis using an Aminex HPX-87P column (BioRad, USA). The RbtD/RbtT/Alx1 operon strain (ZUC99/pATX118) exhibited 23% and 39% conversions of L-arabitol to xylitol after 25 hrs and 49 hrs post induction, respectively (Table 8).

Example 18

Construction of a Screening Strain for Selecting D-Xylose Reductases that are Specific for D-Xylose Reduction The xylA, araBADΔ host strain required for the screen (ZUC29) was constructed as described in example 10. A xdh/araB operon was constructed by as shown in FIG. 26. The araB gene was amplified by PCR using primers SEQ ID NO:38 and SEQ ID NO:39 (Table 2) using E. coli K12 chromosomal DNA as a template. The fragment was digested with BglII/NcoI and ligated into plasmid pZUC15 cleaved with BamHI/NcoI to yield pZUC22. ZUC29 was transformed with pZUC22 to complete the screening strain and was named ZUC41. This strain when transformed with pZUC5 (P. stipitis XR clone) cannot grow on D-xylose/L-arabinose mixtures (Table 9) due to L-arabitol 5-phosphate toxicity and as such can be used to screen for D-xylose specific xylose reductases. This could be achieved by subjecting a cloned XR gene to one or multiple rounds of mutagenesis followed by selection on plates containing D-xylose and L-arabinose. Only mutants that can convert D-xylose to xylitol but not L-arabinose to L-arabitol will be able to grow.

Example 19

Selection of C. tenuis XR Mutants Functional at 37° C. Using XR Screening Strain pZUC49

The C. tenuis XR gene was mutated using the GeneMorph II error-prone PCR kit following the manufacturers protocol (Stratagene, USA). Gene libraries were screened in strain ZUC49 (see Example 10), selection was for growth on M9 minimal medium plates containing D-xylose as sole carbon source at 37° C. A mutant, which could now grow at 37° C. was isolated and shown to confer growth at 37° C. when reintroduced to ZUC49 by electroporation, whereas the w.t. clone pZUC30 did not. Sequencing of the mutated gene showed two changes from the w.t. gene, glycine 32 was changed to a serine (Gly32Ser) and asparagine 138 was changed to an aspartate (Asn138Asp) (SEQ ID NO:44) (FIG. 29).

Example 20

Selection of a D-Xylose Specific XR Reductase

The P. stipitis XR gene was mutated using the GeneMorph II error-prone PCR kit following the manufacturers protocol (Stratagene, USA). Gene libraries were screened in strain ZUC41 (see Example 18), selection was for growth on M9 minimal medium containing 0.2% D-xylose and the minimal amount of L-arabinose that was found to be inhibitory, which was 0.001%. A plasmid linked mutant was obtained that conferred enhanced growth in the presence of 0.001% L-arabinose was obtained. Sequencing of the mutated XR gene showed two mutations, Ser233Pro and Phe286Leu. This mutant has the potential to be improved by directed evolution using iterative mutagenesis and screening for growth on media with increasing concentrations of L-arabinose.

Example 21

Construction of a Xylitol Dehydrogenase Xylose Isomerase (xdh/xylA) Operon and Its Use in Synthesizing Xylitol from D-xylose Via a D-xylulose Intermediate An xdh/xylA operon was constructed as shown in FIG. 27. The xylA fragment was generated by PCR using primers SEQ ED NO:13 and SEQ ID NO:14, using E. coli K12 chromosomal DNA as a template. The fragment was digested with BamHI/NcoI and ligated into pZUC31 restricted with the same enzymes and two independent clones were isolated. The resultant plasmids were named pZUC35 and pZUC36.

To test for synthesis of xylitol using D-xylose as starting substrate (see FIG. 6 for rationale) a host that cannot utilize D-xylose or D-xylulose is favored, e.g. a xylAB mutant. ZUC22 (*E. coli* K12 prototroph AB707, xylAΔ::cam) is such a mutant. In this strain the xylA gene has been replaced with a chloramphenicol (cam) resistance gene, the cam gene has a polar effect on the xylB (D-xylulose kinase) gene downstream of xylA. As such this strain cannot utilize either D-xylose or D-xylulose. ZUC22 was transformed with pZUC35 and pZUC36 by electroporation to form strain ZUC53 and ZUC54. A control strain consisting of ZUC22 transformed with expression vector pTrp338 was also constructed and named ZUC52.

The conversion of D-xylose to xylitol was tested in the following way; 100 ml of M9 minimal medium was made up containing 0.25% glycerol and 0.361% D-xylose, 25 ml aliquots were dispensed into three sterile 100 ml baffle flasks. The flasks were inoculated with 0.25 ml an overnight culture of ZUC52, 53 and 54 grown in LB medium plus 40 ug/ml kanamycin. The flasks were incubated for 24 hr at 37° C. with shaking (250 rpm). Samples were taken after 24 hr then analyzed by HPLC analysis using an Aminex HPX-87P column (BioRad, USA). The results show, that both ZUC53 and ZUC54 exhibited a 65% and 68% conversion of D-xylose to xylitol, whereas the control strain had only a 0.002% conversion (Table 10). This result is unexpected because xylitol dehydrogenase is a catabolic enzyme and is favored in the conversion of xylitol to D-xylulose. One would therefore expect the reaction to reach equilibrium between xylitol, D-xylose and D-xylulose, which it clearly does not.

Example 22

Selection of Sugar Transport Host ZUC72 for Xylitol Synthesis from Hemicellulose It has previously been shown that *E. coli* strains carrying a ptsG mutation are relieved of catabolite repression and that such strains can simultaneously grow on a wide range of sugars in the presence of glucose. See, Kimata et al. (1997). "cAMP receptor protein-cAMP plays a crucial role in glucose-lactose diauxie by activating the major glucose transporter gene in *Escherichia coli*." Proc Natl Acad Sci, 94(24): 12914-12919; Nichols & Dien et al. (2001). "Use of catabolite repression mutants for fermentation of sugar mixtures to ethanol." Appl Microbiol Biotechnol, 56(1-2):120-5.

Such a strain would have a two fold benefit for xylitol synthesis from hemicellulose hydrolysate as one can easily construct a strain that does not grow on D-xylose (the precuror to xylitol) but transports it efficiently while being able to co-utilize glucose and other sugars found in the hemicellulose hydrolyzate. Such a strain was constructed as follows:
1. A phage P1 ptsG tranducing lysate was obtained by growing P1 on *E. coli* strain ND15 (Nichols, Dien et al. 2001) using standard techniques (Short course in Bacterial Genetics: A Laboratory Manual and Handbook for *Escherichia coli* and Related Bacteria, Jeffrey H. Miller, Cold Spring Harbor Laboratory; 1$^{st}$ Ed., (Jan. 15, 1992). The ptsG mutation is closely linked to the tetracycline resistance (tet$^R$) gene of transposon Tn10.
2. *E. coli* AB707 (prototroph) was transduced to tet$^R$ and ptsG mutants were identified as blue colonies when plated on medium containing glucose, lactose and the chromogenic substrate X-gal, the strain was named ZUC56.
3. ZUC56 was transduced to Kan$^R$ using phage P1 grown on BW25113 xylB::kan to yield ZUC58.
4. ZUC58 was passaged several times in M9 glucose minimal medium plus kanamycin (50 mg/L) to select for enhanced glucose utilizers. The fastest growing variant was isolated, purified and named ZUC70.

The kanamycin gene was excised from ZUC70 using FLP mediated excision to yield ZUC72. Datsenko & Wanner (2000). "One-step inactivation of chromosomal genes in *Escherichia coli* K-12 using PCR products." Proceedings of the National Academy of Sciences of the United States of America, 97(12): 6640-6645. ZUC72 can grow efficiently on L-arabinose and glucose simultaneously but cannot utilize D-xylose (Table 11).

Example 23

Mutagenesis and Selection of Xylitol Resistant Xylose Isomerases

The GeneMorph II kit (Stratagene) was used to generate error-prone PCR library following the standard procedure to generate approximately 1-10 mutations per 1000 base pairs. The *E. coli* xylose isomerase gene (xylA) was initially cloned into the pTRP338-H3 expression plasmid using BamHI/NcoI restriction sites. DNA primers SEQ ID NO: 40 and SEQ ID NO: 41 (Table 2), were used to amplify the xylA gene using a GeneMorph II kit. The randomly mutated gene was the digested with restriction enzymes and ligated into freshly prepared pTRP338-H3 plasmid. This library was initially transformed into EC100 cells (Epicentre), plated onto rich growth media containing kanamycin (50 mg/L), and incubated overnight at 37° C. The resulting transformants were then scraped form from the plates and resuspended in fresh L-broth. The cells were pelleted by centrifugation, and the plasmid library was extracted using a HiSpeed midiprep plasmid isolation kit (Qiagen). This extra step in preparing this plasmid library was necessary to create a high concentration of plasmid DNA that was more suitable for transformation into the *E. coli* selection strain (ZUC29). Selection strain ZUC29 was then transformed with the mutated plasmid library using standard electroporation procedures. After phenotypic expression of the plasmid encoded kanamycin resistance gene, the cells were washed with 1×M9 salts to remove any residual rich growth media. The cells were then resuspended in 1×M9 salts and plated onto minimal M9 media containing kanamycin (50 mg/L), 0.2% D-xylose (w/v), and up to 10% xylitol (w/v). The plates were incubated at 37° C. until colonies appeared, usually 2-3 days.

The fast growing colonies were picked and restreaked onto fresh selection media plates and incubated at 37° C. The restreaking step is necessary to remove contaminating slower growing colonies from the original selection plate. Plasmid DNA was extracted from fast growing isolates from the second selection. ZUC29 was then transformed with the putative xylitol resistant candidates and screened again for growth on D-xylose/xylitol selection plates. Plasmids that transferred the xylitol resistant phenotype (XTL$^R$) were DNA sequenced (ACGT, Inc.) and compared to the w.t. DNA sequence, the differences in the translation of the mutants versus the w.t. sequence was then determined (Table 12). This cycle was repeated twice using the best isolate from each round of mutagenesis as the parent for the next round to produce mutant #3 that could grow in the presence of 3% xylitol.

Mutant #3 was further mutagenized using the XL1-RED mutagenesis kit (Stratagene). Mutant #8 was further mutagenized by error prone pcr (GeneMorph II, Stratagene)

and a mutant was selected that was able to grow in the presence of 10% xylitol (Table 12), the gene had one additional mutation H439Q. Finally, the mutated xylA was cloned behind the xdh gene of pZUC31 using a BamHI/NcoI digest to form pZUC52 prior to fermentation testing (similar construction as shown in FIG. 21).

Example 24

Fermentation of W.T. xylA and Mutant xylA10% Using 5% D-Xylose as Substrate

ZUC72 was transformed with pZUC36 (FIG. 21) and pZUC52 to yield strains ZUC73 and ZUC112 respectively. The strains were tested for the conversion of D-xylose to xylitol in 1 L BIOSTATOB fermenters (B. Braun) under the following conditions:

| Growth Medium | g/L |
|---|---|
| Tryptone | 10 |
| Yeast extract | 5 |
| Potassium phosphate, dibasic | 3 |
| Potassium phosphate monobasic | 2 |
| Sodium chloride | 5 |
| Magnesium sulfate | 1 |
| Water to 925 ml | |

The vessels were sterilized with the above media in situ, D-xylose (70 g in 175 ml) and D-glucose (60 g in 150 ml) was sterilized separately. Preinoculation, 100 ml of D-xylose and 20 ml of D-glucose feed was added to the vessel. The fermenters were inoculated with 50 ml of an overnight starter culture grown in LB at 37° C. and run under the following conditions:

| Temperature | 37° C. |
|---|---|
| pH | 7.0 (NAOH control) |
| Air | 2 LPM (2 VVM) |
| Feed | D-xylose: 75 ml, 6-22 hr |
| | D-glucose: 130 ml, 8-46 hr |
| Agitation | 1200 |

Samples were taken at regular time intervals and analyzed by HPLC. The results show that the xylitol resistant xylose isomerase (XI$^{10\%}$) produced 3.3% xylitol after 30 hr as compared to the w.t. XI which produced only 1.8% in the same amount of time. This represents a 54% increase in xylitol titer of the fermentation.

Example 25

Synthesis of Xylitol by ZUC112 Using 10% Under High D-Xylose Conditions

Fermentations were run as follows:

| | |
|---|---|
| Bacto Tryptone | 10 g |
| Bacto Yeast extract | 5 g |
| Potassium phosphate, dibasic | 3 g |
| Potassium phosphate monobasic | 1.5 g |
| Sodium chloride | 5 g |
| Magnesium sulfate·7H2O | 1 g |
| Cognis BioSpumex 36K antifoam | ~4 drops |
| Water to 750 mL | |

The vessels were sterilized with the above media in situ, D-xylose (100 g) and D-glucose (10 g) was sterilized in 170 ml water separately and added prior to inoculation of the vessel. A D-xylose (100 g), D-glucose feed (60 g) was dissolved in 270 ml water, sterilized and used to feed the fermentation to keep the D-xylose concentration ~8%. The fermenters were inoculated with 50 ml of an overnight starter culture grown in LB at 37° C. and run under the following conditions:

| Temperature | 37° C. |
|---|---|
| pH | 7.0 (NaOH control) |
| Air | 2 LPM (2 VVM) |
| Feed | D-xylose/D-glucose: 277 ml, 13-33 hr |
| Agitation | 1200 |
| Volume after inoculation | 970 ml |
| Final Volume (70 hr) | 1105 ml |

Under high xylose conditions a maximum of 7.2% xylitol (72 g/L) was synthesized from 200 g of D-xylose or 79.5 g total when allowing for dilution due to feeding (final volume 1105 ml).

TABLE 1

Examples of Various Sugars in Agricultural Residues (% dry weight)

| Residue | D-Xylose (%) | L-Arabinose (%) | D-Glucose (%) |
|---|---|---|---|
| Bagasse | 60 | 15 | 25 |
| Corn Cobs | 65 | 10 | 25 |
| Flax Straw | 65 | 13 | 1 |
| Wheatstraw | 58 | 9 | 28 |

TABLE 2

List of DNA PCR primers.

| Enzyme | Organism | Forward Primer | Reverse Primer |
|---|---|---|---|
| XR | P. stipitis | SEQ ID NO: 1 GTGTGTGTCATATGCCTTCTA TTAAGTTGAACT | SEQ ID NO: 2 GTGTGGATCCTTAGACGAAG ATAGGAATCTTGTC |
| XR | E. coli K12 | SEQ ID NO: 3 GTGTGAATTCGATGGCTATCC CTGCATTTGG | SEQ ID NO: 4 CACAGGATCCCTAATCCCATT CAGGAGCCA |
| XR | C. tenuis | SEQ ID NO: 5 GAGAGAATTCGATGAGCGCA AGTATCCCAGAC | SEQ ID NO: 6 GAGAGGATCCTTAAACGAAG ATTCGAATGTTGTC |

TABLE 2-continued

List of DNA PCR primers.

| Enzyme | Organism | Forward Primer | Reverse Primer |
|---|---|---|---|
| LAD1 | T. reesei | SEQ ID NO: 7<br>GTGTGAATTCGATGTCGCCTT<br>CCGCAGTCGA | SEQ ID NO: 8<br>GTGTGGATCCTCAATCCAGGC<br>TCTGAATCATGAC |
| LXR | T. reesei | SEQ ID NO: 9<br>GTGTGAATTCGATGCCTCAGC<br>CTGTCCCCAC | SEQ ID NO: 10<br>GTGTGGATCCTTATCGTGTAG<br>TGTAACCTCCGTC |
| XDH | T. reesei | SEQ ID NO: 11<br>GTGTGAATTCGATGGCGACTC<br>AAACGATCAAC | SEQ ID NO: 12<br>CACAGGATCCTTACACCTTCT<br>CGTTGGGCC |
| XylA | E. coli K12 | SEQ ID NO: 13<br>TATAAGCTTAAGGAGGATCC<br>ATTATGGAGTTCAA | SEQ ID NO: 14<br>TCGAAGCTTAGATCTCCATGG<br>TTATTTGTCGAAC |
| LXR1 | T reesei | SEQ ID NO: 15<br>TGCTCTAGATAAGGAGGATA<br>ATAAATGCCTCAGCCTGTCCC<br>CAC | SEQ ID NO: 16<br>TGCTCTAGATAAGGAGGATA<br>ATAAATGCCTCAGCCTGTCCC<br>CAC |
| LAD1 | T. reesei | SEQ ID NO: 17<br>TCGGATCCTAAGGAGGATAT<br>ATAATGTCGCCTTCCGCAGTC<br>GATG | SEQ ID NO: 18<br>AGCTCTAGATCAATCCAGGCT<br>CTGAATCATGAC |
| XDH | G. oxydans | SEQ ID NO: 19<br>CAGCGATGAATTCGAAGAAG | SEQ ID NO: 20<br>AGCGGATCCTTAACCGCCAGC<br>AATCGGC |
| XylA<br>RED<br>deletion | E. coli K12 | SEQ ID NO: 21<br>CCAATATTACGACATCATCCA<br>TCACCCGCGGCATTACCTGGT<br>GTAGGCTGGAGCTGCTTC | SEQ ID NO: 22<br>TACCGATAACCGGGCCAACG<br>GACTGCACAGTTAGCCGTTAC<br>ATATGAATATCCTCCTTAG |
| LyxK | E. coli | SEQ ID NO: 23<br>AGCGAATTCATGACGC<br>AATACTGGCTGG | SEQ ID NO: 24<br>ATCGGATCCTATAATGTGTG<br>CTCCTTAATGC |
| UlaE/F | E. coli | SEQ ID NO: 25<br>TCTAGATCTAATATGTTGTCC<br>AAACAAATCC | SEQ ID NO: 26<br>GCACCATGGTTACTTCTGCCC<br>GTAATAAG |
| ALX1 | A. monospora | SEQ ID NO: 27<br>GCGAATTCGATGACTGACT<br>ACATTCCAAC | SEQ ID NO: 28<br>GAGGGATCCCTACCAAGA<br>AGTGAAACC |
| ALX1 | A. monospora | SEQ ID NO: 29<br>GCGGATCCATAAAGGAGG<br>ATATATAATGACTGACTAC<br>ATTCC | SEQ ID NO: 30<br>GCTCTAGACTACCAAGAA<br>GTGAAACCACCATCAAC |
| XR | P. stipitis | SEQ ID NO: 31<br>GCGGATCCCGACATCATAA<br>CGGTTC | SEQ ID NO: 32<br>GCGGATCCTTAGACGAAG<br>ATAGGAATCTTGTC |
| RBTD | K. pneumoniae | SEQ ID NO: 33<br>GCGGAATTCGATGAAGCA<br>CTCTGTCTCCTC | SEQ ID NO: 34<br>CGGGATCCTCAGAGATCCA<br>CGCTGTTC |
| RBTT | K. pneumoniae | SEQ ID NO: 35<br>GCGGATCCTAAGGAGGAT<br>ATATTATGTCCGTTAATAA<br>CAAA C | SEQ ID NO: 36<br>GCTCTAGATTAAGACTCTG<br>CCGCGTTG |
| ALX1 | A. monospora | SEQ ID NO: 37<br>GCCTCTAGACGACATCATA<br>ACGGTTCTG | SEQ ID NO: 30<br>GCTCTAGACTACCAAGAA<br>GTGAAACCACCATCAAC |
| AraB | E. coli | SEQ ID NO: 38<br>TTCAGATCTAACGATGGCGAT<br>TGC | SEQ ID NO: 39<br>GCACCATGGTTATAGAGTCGC<br>AACGGCCTG |
| pTRP200-<br>seq-forw<br>primer | | SEQ ID NO: 40<br>CGAACTAGTTAACTTTTACGC<br>AAGT | |

TABLE 2-continued

List of DNA PCR primers.

| Enzyme | Organism | Forward Primer | Reverse Primer |
|---|---|---|---|
| pTRP338-seq-rev primer | | | SEQ ID:41 GGCTGAAAATCTTCTCTCATCC |

TABLE 3

Growth Phenotypes of XR Screening Strains.

| Strain | Plasmid/ Gene | Genotype | Growth at 30° C. and 37° C. | | |
|---|---|---|---|---|---|
| | | | D-Glu | D-Xylose | Xylitol |
| ZUC24 | | xylAΔ | Yes | No | No |
| ZUC25 | | xylAΔ, λ-, IN[rrnD-rrnE]1, rph-1 | Yes | No | No |
| ZUC26 | pZUC15/xdh | xylAΔ | Yes | No | Yes |
| ZUC27 | pZUC15/xdh | xylAΔ, λ-, IN[rrnD-rrnE]1, rph-1 | Yes | No | Yes |
| ZUC49 | pZUC31/xdh | xylAΔ, λ-, IN[rrnD-rrnE]1, rph-1 | Yes | No | Yes |

TABLE 4

Utility of XR Screening Strains.

| Strain | Host Strain | Plasmid/Gene | Relevant Genotype | Growth at 30° C. | |
|---|---|---|---|---|---|
| | | | | D-Glu | D-Xylose |
| ZUC26 | ZUC24 | pZUC15/xdh | xylAΔ | Yes | No |
| ZUC31 | ZUC24 | pZUC15/xdh + pTTQ18 control | xylAΔ | Yes | No |
| ZUC32 | ZUC24 | pZUC15/xdh + pZU19/yafB | xylAΔ | Yes | Yes |
| ZUC27 | ZUC24 | pZUC15/xdh + pZUC5/XR | xylAΔ | Yes | Yes[1] |
| ZUC49 | ZUC25 | PZUC31/XR | xylAΔ | Yes | No |
| ZUC50 | ZUC49 | pZUC31/xdh + pZUC30/XR | xylAΔ | Yes | Yes[1] |

[1]No growth at 37° C., i.e. both xylose reductases temperature sensitive.

TABLE 5

Conversion of L-Arabitol to Xylitol via an L-Xylulose Intermediate.

| Strain | IPTG | L-Arabitol (g/L) | | L-Xylulose (g/L) | | Xylitol (g/L) | | % Con[1] |
|---|---|---|---|---|---|---|---|---|
| | | 0 hr | 25 hrs | 0 hr | 25 hrs | 0 hr | 25 hrs | |
| ZUC99/pATX106 | + | 10.4 | 8.73 ± 0.13 | 0 | 0.57 ± 0.05 | 0 | 0.64 ± 0.03 | 6.2 |
| ZUC99/pATX106 | − | 10.4 | 10.1 ± 0.01 | 0 | 0 | 0 | 0 | 0 |

[1]% conversion of L-arabitol to xylitol in 25 hrs.

TABLE 6

Conversion of L-Arabinose to Xylitol via an L-Arabitol and L-Xylulose Intermediates.

| Strain | L-Arabinose (g/L) | | L-Arabitol (g/L) | | L-Xylulose (g/L) | | Xylitol (g/L) | | % Con[1] |
|---|---|---|---|---|---|---|---|---|---|
| | 0 hr | 24 hrs | 0 hr | 24 hrs | 0 hr | 24 hrs | 0 hr | 24 hrs | |
| ZUC99/pATX112 | 9.96 | 5.57 ± 0.23 | 0 | 4.69 ± 0.32 | 0 | 0 | 0 | 0.17 ± 0.08 | 1.7 |

[1]% conversion of L-arabinose to xylitol in 24 hrs.

TABLE 7

Conversion of L-Arabitol to L-Xylulose using Ribitol Dehydrogenase with or without Ribitol Transporter.

| Strain | L-Arabitol (g/L) | | L-Xylulose (g/L) | | % Conversion[1] |
|---|---|---|---|---|---|
| | 0 hr | 24 hrs | 0 hr | 24 hrs | |
| ZUC99/pATX114 | 10.94 | 7.75 ± 0.09 | 0 | 2.09 ± 0.16 | 19 |
| ZUC99/pATX115 | 10.94 | 2.78 ± 0.19 | 0 | 6.28 ± 0.50 | 57 |

[1]% conversion of L-arabitol to L-xylulose in 24 hrs.

TABLE 8

Conversion of L-Arabitol to Xylitol using RbtD/RbtT/Alx1 Operon.

| Strain | L-Arabitol (g/L) | | | L-Xylulose (g/L) | | | Xylitol (g/L) | | | % Conversion[1] | |
|---|---|---|---|---|---|---|---|---|---|---|---|
| | 0 hr | 25 hrs | 49 hrs | 0 hr | 25 hrs | 49 hrs | 0 hr | 25 hrs | 49 hrs | 25 hrs | 49 hrs |
| ZUC99/pATX118 | 11.9 | 8.26 ± 0.64 | 3.01 ± 0.37 | 0 | 1.00 ± 0.07 | 3.46 ± 0.27 | 0 | 2.76 ± 0.14 | 4.58 ± 0.16 | 23 | 39 |

[1] % conversion of L-arabitol to xylitol in 25 hrs or 49 hrs.

TABLE 9

Toxicity of L-Arabinose in the Presence of Xylose Reductase Activity.

| | | | Growth at 30° C. | | |
|---|---|---|---|---|---|
| Strain/Plasmid | Relevant Genotype | Plasmid Genes | 0.2% Glucose[1] | 0.2% D-xylose[1] | 0.2% D-xylose + 0.2% L-ara[1] |
| ZUC29/pZUC22 + PZUC5 | Δ(araD-araB)567, xylAΔ | xdh, araB, xr | Yes | Yes | No[2] |
| ZUC29/pZUC5 | Δ(araD-araB)567, xylAΔ | xr | Yes | No[2] | No[2] |

[1] M9 minimal medium + 1 mM IPTG
[2] Growth was followed for up to 96 hr.

TABLE 10

Conversion of D-Xylose to Xylitol via a D-Xylulose Intermediate.

| Strain | Host/Plasmid | Glycerol | | D-Xylose | | D-Xylulose | | Xylitol | | % Con[1] |
|---|---|---|---|---|---|---|---|---|---|---|
| | | 0 hr | 24 hr | 0 hr | 24 hr | 0 hr | 24 hr | 0 hr | 24 hr | |
| ZUC52 | ZUC22/pTrp228 | 0.247 | 0 | 0.361 | 0.356 | 0 | 0.000 | 0 | 0.001 | 0.002 |
| ZUC53 | ZUC22/pZUC35 | 0.247 | 0 | 0.361 | 0.034 | 0 | 0.057 | 0 | 0.236 | 65.373 |
| ZUC54 | ZUC22/pZUC36 | 0.247 | 0 | 0.361 | 0.031 | 0 | 0.053 | 0 | 0.245 | 67.867 |

% conversion of D-xylose to xylitol in 24 hr.

TABLE 11

Utilization of Sugars by ZUC72

| Strain/Genotype | Time (hr) | D-Glucose | D-Xylose | L-Arabinose |
|---|---|---|---|---|
| AB707 | 0 | 0.071 | 0.160 | 0.118 |
| AB707 | 13 | 0.034 | 0.179 | 0.162 |
| AB707 | 24 | 0.000 | 0.048 | 0.000 |
| ZUC72 | 0 | 0.109 | 0.211 | 0.167 |
| ZUC72 | 13 | 0.076 | 0.197 | 0.116 |
| ZUC72 | 24 | 0.034 | 0.172 | 0.018 |

TABLE 12

Mutations found in xylitol resistant xylose isomerase mutants.

| Gene | Generated | Parent | Mutations | % XTL[R] |
|---|---|---|---|---|
| WT | N/A | | None | <0.5 |
| #1 | GeneMorph II | WT | F9L, L213Q, F283Y, K311R, H420N | 1 |
| #3 | GeneMorph II | #1 | F9L, Q11K, L213Q, F283Y, K311R, H420N | 3 |
| #8 | XL-1 Red | #3 | F9L, Q11K, S20L, L213Q, F283Y, K311R, H420N | 5 |
| #9 | GeneMorph II | #8 | F9L, Q11K, S20L, L213Q, F283Y, K311R, H420N, H439Q | 10 |

We claim:

1. A recombinant bacterium that expresses proteins comprising:
   (a) xylose specific reductase, wherein the xylose specific reductase is a *Pichia stipitis* reductase with Ser233Pro and Phe286Leu mutations;
   (b) L-arabitol dehydrogenase or ribitol dehydrogenase or both; and
   (c) L-xylulose reductase;
that have a biochemical activity that produces xylitol from substrates comprising D-xylose; or L-arabinose; or L-arabinose and D-xylose, such that the recombinant bacterium produces and accumulates xylitol, and accumulates no substantial amount of L-arabitol; wherein the xylose reductase protein, or L-arabitol dehydrogenase protein, or ribitol dehydrogenase protein, or L-xylulose reductase protein, or a combination thereof are expressed from a recombinant polynucleotide.

2. The recombinant bacterium of claim 1, wherein the recombinant bacterium produces and accumulates xylitol from substrates comprising a xylan hydrolysate or a hemicellulose hydrolysate.

3. The recombinant bacterium of claim 1, wherein the bacterium further expresses a ribitol transporter protein.

4. The recombinant bacterium of claim 1, wherein the bacterium is *Escherichia coli*.

5. The recombinant bacterium of claim 1, wherein the bacterium does not have a ptsG gene or has an inactive ptsG gene.

6. The recombinant bacterium of claim 1, wherein the recombinant bacterium produces L-arabitol as an intermediate to the xylitol end-product.

7. The recombinant bacterium of claim 1, wherein the recombinant bacterium produces L-xylulose as an intermediate to the xylitol end-product.

8. The recombinant bacterium of claim 1, wherein the recombinant bacterium comprises one or more recombinant polynucleotides encoding aldose reductase, L-xylose reductase, L-arabitol dehydrogenase, ribitol dehydrogenase, ribitol transporter, or L-xylulose reductase.

9. The recombinant bacterium of claim 8, wherein the recombinant polynucleotide encoding xylose reductase is a *Pichia stipitis* polynucleotide.

10. The recombinant bacterium of claim 8, wherein the recombinant polynucleotide encoding ribitol dehydrogenase is a *Klebsiella pneumoniae* or *Klebsiella aerogenes* polynucleotide.

11. The recombinant bacterium of claim 8, wherein the recombinant polynucleotide encoding L-xylulose reductase is an *Ambrosioyma monospora* polynucleotide.

12. The recombinant bacterium of claim 8, wherein the recombinant polynucleotide encoding L-xylose reductase comprises a yafB or yajO polynucleotide from *Escherichia coli*.

13. The recombinant bacterium of claim 7, wherein the recombinant polynucleotide encoding L-arabitol dehydrogenase is a *Trichoderma reesei* polynucleotide.

14. The recombinant bacterium of claim 8, wherein the recombinant polynucleotide encoding L-xylose reductase is a *T. reesei* polynucleotide.

15. A method for producing a xylitol end-product comprising fermenting a substrate comprising D-xylose; or L-arabinose; or L-arabinose and D-xylose; or L-arabinose, D-xylose and other sugars with the recombinant bacterium of claim 1.

16. The method of claim 15, wherein L-arabitol is produced as an intermediate to the xylitol end-product.

17. The method of claim 15, wherein L-xylulose in produced as an intermediate to the xylitol end-product.

18. The method of claim 15, wherein in the method does not require separation of L-arabitol from the xylitol end-product.

19. A method for producing L-xylulose comprising fermenting a substrate comprising D-xylose; or L-arabinose; or L-arabinose and D-xylose; or L-arabinose, D-xylose and other sugars with the recombinant bacterium of claim 1, and collecting L-xylulose before it is converted to xylitol.

20. A method of producing xylitol from a substrate comprising D-xylose; or L-arabinose; or L-arabinose and D-xylose; or L-arabinose, D-xylose and other sugars; comprising contacting the substrate with the isolated recombinant bacteria of claim 1,
   wherein the substrate is converted to an end-product of xylitol and wherein substantially no L-arabitol is produced as an end-product.

21. The method of claim 20, wherein the isolated recombinant bacteria comprise ribitol transporter activity.

22. An isolated recombinant microorganism that expresses a recombinant xylose specific reductase protein, wherein the xylose specific reductase protein is a *Pichia stipitis* reductase protein with Ser233Pro and Phe286Leu mutations.

23. The isolated recombinant microorganism of claim 22, wherein the microorganism can produce an end-product of xylitol from a substrate comprising D-xylose; or L-arabinose; or L-arabinose and D-xylose; or L-arabinose, D-xylose and other sugars.

24. The isolated recombinant microorganism of claim 22, wherein the microorganism produces no substantial amount of L-arabitol as an end-product.

25. The isolated recombinant microorganism of claim 22, wherein the microorganism does not substantially produce L-arabitol from a substrate of xylan hydrolysate or hemicellulose hydrolysate.

26. The isolated recombinant microorganism of claim 22, wherein the microorganism is *E. coli*.

27. The isolated recombinant microorganism of claim 22, wherein the microorganism does not have a ptsG gene or has an inactive ptsG gene.

28. The isolated recombinant microorganism of claim 22, wherein the recombinant microorganism is non-pathogenic.

29. The isolated recombinant microorganism of claim 22, wherein the microorganism is a bacteria, fungus or yeast.

30. The isolated recombinant microorganism of claim 22, wherein the xylose specific reductase protein has an amino acid sequence comprising SEQ ID NO:43.

31. A method for producing xylitol comprising fermenting a substrate comprising D-xylose; or L-arabinose; or L-arabinose and D-xylose; or L-arabinose, D-xylose and other sugars; or xylan hydrolysate; or hemicellulose hydrolysate with the isolated microorganism of claim 22.

32. The method of claim 31, wherein the method does not require separation of L-arabitol from xylitol.

33. A purified xylose specific reductase comprising SEQ ID NO:43.

34. A purified *P. stipitis* xylose reductase comprising a Ser233Pro mutation and a Phe286Leu mutation.

35. The recombinant bacterium of claim 1, wherein: the L-arabitol dehydrogenase protein and the L-xylulose reductase protein are expressed from a recombinant yeast polynucleotide.

* * * * *